United States Patent [19]

Borror

[11] 3,931,228
[45] Jan. 6, 1976

[54] PROCESS FOR PREPARING PHTHALIDE AND NAPHTHALIDE INDICATOR DYES

[75] Inventor: Alan L. Borror, Lexington, Mass.

[73] Assignee: Polaroid Corporation, Cambridge, Mass.

[22] Filed: Feb. 28, 1974

[21] Appl. No.: 446,716

Related U.S. Application Data

[63] Continuation-in-part of Ser. No. 108,662, Jan. 21, 1971, abandoned.

[52] U.S. Cl. .................. 260/326.12R; 260/287 CF; 260/287 XA; 260/309; 260/326.13 R; 260/326.14 R; 260/326.25; 260/326.27; 260/326.34; 260/343.2 R; 260/343.3; 260/343.4
[51] Int. Cl.² ............. C07D 209/10; C07D 209/12; C07D 209/14
[58] Field of Search .......... 260/326.14 R, 326.13 R, 260/326.12 R

[56] References Cited
UNITED STATES PATENTS
3,491,116  1/1970  Lin ........................... 260/326.14 R

*Primary Examiner*—Lewis Gotts
*Assistant Examiner*—S. P. Williams
*Attorney, Agent, or Firm*—Sybil A. Campbell

[57] ABSTRACT

This invention relates to a process of preparing phthalein indicator dyes including phthalides and naphthalides derived from certain hydroxy-substituted carbocyclic aryl compounds, such as phenols, and from certain N-heterocyclic aryl compounds, such as indoles, and to a process of preparing novel intermediates useful therein. According to the present invention, the selected carbocyclic compound, or the selected N-heterocyclic compound is reacted with phthalaldehydic or naphthalaldehydic acid to form the corresponding (na)phthalidyl adduct which is treated with an oxidizing agent to yield the subject intermediates. To prepare the indicator dye, the intermediate, i.e, the oxidation product thus obtained is then reacted with a carbocyclic or heterocyclic aryl compound to yield the corresponding indicator dye. The oxidation products comprising the novel intermediates of the present invention may be dehydro or hydrated (na)phthalidyl adducts.

31 Claims, No Drawings

PROCESS FOR PREPARING PHTHALIDE AND NAPHTHALIDE INDICATOR DYES

CROSS-REFERENCE TO RELATED APPLICATIONS

This application is in part a continuation of copending application Ser. No. 108,662 filed Jan. 21, 1971, now abandoned.

BACKGROUND OF THE INVENTION

1. Field of the Invention

This invention relates to a novel method of preparing indicator dyes, to novel intermediates useful in the preparation of the dyes and to the preparation of the intermediates.

2. Description of the Prior Art

Dyes which undergo a change in spectral absorption characteristics in response to a change in pH are well known in the art and are frequently referred to as indicator or pH-sensitive dyes. Typically, these dyes change from one color to another, from colored to colorless or from colorless to colored on the passage from acidity to alkalinity or the reverse and are commonly employed in analytical chemical procedures to measure changes in pH value. Among the indicator dyes most widely used in the group derived from phthaleins as exemplified by phenolphthalein, thymolphthalein, o-cresolphthalein and 1-naphtholphthalein.

Various methods are known in the art for preparing phthalein indicator dyes. In one of the more conventional procedures, phenols, such as thymol, o-cresol, and phenol itself are reacted with phthalic anhydride at elevated temperatures in the presence of a suitable catalyst such as zinc chloride or sulfuric acid to yield the corresponding symmetrical, i.e., di-phenol phthalein. Di-indole phthaleins also have been prepared by simple condensation usually in the presence of an acid catalyst and by other methods, such as, reacting magnesium indyl bromide with phthalyl chloride Another method of synthesizing indole phthaleins is disclosed in British Patents Nos. 1,160,940; 1,161,386; 1,161,387; and 1,162,771, which comprises reacting an indole with phthalic anhydride in the presence of a metal halide, e.g., aluminum chloride to yield a keto-acid intermediate which is subsequently reacted with a second aromatic compound, the same or different, in the presence of an acid condensing agent to yield the desired indole phthalein. Using this method both symmetrical and unsymmetrical compounds may be prepared by selecting respectively, as the second aromatic compound, an indole which is the same or an indole which is different from the starting indole initially reacted with the anhydride. Where it is desired to produce a mixed indole phthalein containing an indole radical and a second radical derived from a different aromatic compound such as carbazole or aniline the keto-acid intermediate may be formed by reaction of the indole, carbazole or other appropriate compound with phthalic anhydride followed by condensation of the intermediate with the second aromatic compound to yield the desired mixed indole indicator dye.

These prior methods of preparing phthaleins, though useful in synthesizing a large number of compounds, are accompanied by certain drawbacks. The simple condensation reactions and the Grignard reactions are not useful with all starting materials. Some phenols and indoles will not react under the condensation conditions conventionally employed. Moreover, these synthetic methods generally are limited to the production of symmetrical compounds, i.e., di-phthalides containing two indole or two phenol radicals that are identical. While the method of the aforementioned British patents is useful for producing symmetrical and unsymmetrical indole phthaleins and also mixed indole indicator dyes, the more sensitive indole derivatives, when used as starting materials, tend to decompose under the vigorous reaction conditions encountered in the presence of the aluminum chloride catalyst.

It is known from the work of Brubaker, et al., J. Amer. Chem. Soc., 49, 2279 (1927) that o-phthalaldehydic acid condenses with phenol and certain substituted phenols having a free par-position to yield the para-condensation products. These compounds were prepared by mixing equimolar proportions of phenol and phthalaldehydic acid and then adding a suitable condensing acid, such as sulfuric acid, while maintaining the reaction temperature below about 30°C.

As reported by Norland, et al., ibid, 82, 5143 (1960), phthalaldehydic acid and indoles will condense to yield phthalidylindoles and water then the two reactants are fused together at temperatures of 120° to > 200°C. If the 3-position of the indole is free, then 3-phthalidylindoles are formed. If the 3-position is blocked or if the 1- and 3-positions are blocked, then 1-phthalidylindoles and 2-phthalidylindoles are formed, respectively.

Rees, et al., J. Chem. Soc., pp. 680–687 (1965) observed that for reaction with phthalaldehydic acid the 3-substituted indoles and the 1,3-disubstituted indoles generally require the vigorous fusion conditions used by Norland et al., but found that indoles having a free 3-position will react with phthalaldehydic acid under milder conditions. Indole and its 2-phenyl, 2-methyl, 7-methyl and 1,2-dimethyl deriviatives were reported to react in hot benzene to yield the corresponding 3-phthalidyl indoles which results were attributed to intramolecular acid catalysis. In solution phthalaldehydic acid exists in the cyclic form, 3-hydroxyphthalide, which is in rapid equilibrium with the open-ring form, O-formylbenzoic acid. Presumably, the indole reacts with the aldehyde form and the carboxyl group ortho to the aldehyde group functions as an intramolecular acid catalyst. The authors observed that reactions with indole and 2-methyl indole also were catalyzed by an external acid catalyst, such as toluene-p-sulfonic acid, and also that a second mole of indole could be added to 3-phthalidylindole by opening the lactone ring with alkali and treating the resulting salt with a second mole of indole.

Rees et al. in further studies, ibid., pp. 687–91 (1965), reported that the condensation of phthalaldehydic acid could be extended to pyrroles and found that phthalaldehydic acid reacted with pyrrole and 2,5-dimethyl pyrrole in boiling benzene in the absence of an external catalyst to give high yields of 2-phthalidyl-pyrrole and 3-phthalidylpyrrole, respectively. In these reactions, it was observed that pyrrole tended to substitute in the 2-position when possible to yield the 2-phalidyl derivative. In a further extension of the reactions, the authors found that naphthaldehydic acid, though less reactive than phthalaldehydic acid, behaved in a similar manner and could be condensed with indole under fusion conditions to yield 3-naphthalidylindole.

It has now been found that certain phthalidyl-substituted phenols, naphthols, indoles and pyrroles and the corresponding naphthalidyl derivatives may be oxidized to yield novel intermediates which will condense readily with another mole of the same aromatic compound as used in the initial condensation reaction or a different aromatic compound, to yield a phthalide or naphthalide indicator dye.

SUMMARY OF THE INVENTION

It is, therefore, the primary object of the present invention to provide a novel method of synthesizing phthalein indicator dyes.

It is another object of the present invention to provide a method of synthesizing phthalide and naphthalide indicator dyes which may be symmetrical, unsymmetrical or mixed indicator dyes.

It is a further object of the present invention to provide novel intermediates useful in the preparation of such dyes and to provide a method for preparing the intermediates.

Other objects of this invention will in part be obvious and will in part appear hereinafter.

The invention accordingly comprises the process involving the several steps and the relation and order of one or more of such steps with respect to each of the others and the product possessing the features, properties and the relation or elements which are exemplified in the following detailed disclosure and the scope of the application of which will be indicated in the claims.

According to the present invention, there is provided a novel method of preparing phthalein indicator dyes that is generally applicable to the synthesis of phthalides and naphthalides of certain hydroxy-substituted carbocyclic aryl compounds, namely, phenols and benzphenols (i.e., 1-naphthols) and certain N-heterocyclic aryl compounds, namely, pyrrols and benzpyrroles (i.e., indoles). The present method comprises (1) reacting a hydroxy-substituted carbocyclic compound selected from a phenol and a 1-naphthol or an N-heterocyclic aryl compound selected from an indole and a pyrrole with phthalaldehydic or napthalaldehydic acid to form the corresponding (na)phthalidyl-substituted intermediate, (2) oxidizing the intermediate and (3) reacting the oxidation product with an aromatic compound selected from carbocyclic aryl and heterocyclic aryl to form the complete indicator dye. As used herein, the expression "(na)phthalidyl" is intended to denote either the corresponding phthalidyl- or naphthalidyl-substituted intermediate depending upon the selection of phthalaldehydic or naphthalaldehydic acid.

Since the reaction conditions are comparatively mild, the present invention allows greater latitude in the selection of starting materials. For example, the indole derivatives to be intially reacted with the acid are not limited to the more stable compounds but may include alkali and acid sensitive compounds as well. The present invention also allows greater latitude in the indicator dyes that may be produced. Novel intermediates are obtained as the oxidation product of step (2) which may be reacted with any of various aromatic compounds in step (3) to form a complete dye so that both symmetrical and unsymmetrical phthalides and naphthalides and also, mixed indicator dyes, such as phthalides and naphthalides containing, for example, one phenol radical and one indole radical, may be readily synthesized.

For a fuller understanding of the nature and objects of the present invention reference should be had to the following detailed description.

DESCRIPTION OF THE PREFERRED EMBODIMENTS

Specifically, the method of the present invention comprises:

1. reacting a compound selected from (a) a hydroxy-substituted carbocyclic aryl compound having a free position para to the hydroxy group selected from a phenol and a 1-naphthol and (b) and N-heterocyclic aryl compound having hydrogen substituted on the nitrogen atom selected from an indole having a free 3-position and a pyrrole having a free 2-position with a compound selected from phthalaldehydic and naphthalaldehydic acid to form a compound having the formula:

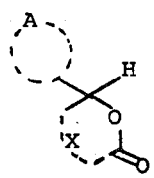

wherein A is selected from p-hydroxyphenyl, p-hydroxynaphthyl, indol-3-yl and pyrr-2-yl and X represents the carbon atoms necessary to complete a ring-closing moiety selected from phthalide and naphthalide;

2. converting the last-named compound by oxidation to a compound selected from

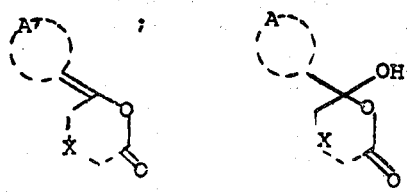

and mixtures thereof
wherein A' is selected from

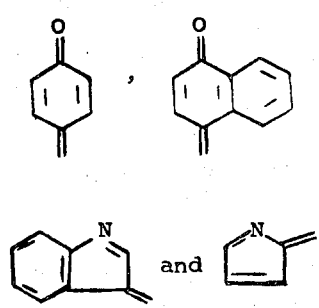

and A and X have the same meaning as above; and 3. reacting said last-named compound with an aromatic compound selected from a carbocyclic aryl compound and a heterocyclic aryl compound to form an indicator dye of the formula:

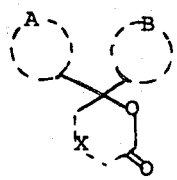

wherein B is selected from carbocyclic aryl and heterocyclic aryl and A and X have the same meaning as above.

The above reaction scheme is illustrated below ultimately comprises the B radical of the indicator dye and X represents the carbon atoms necessary to complete the phthalide or naphthalide moiety.

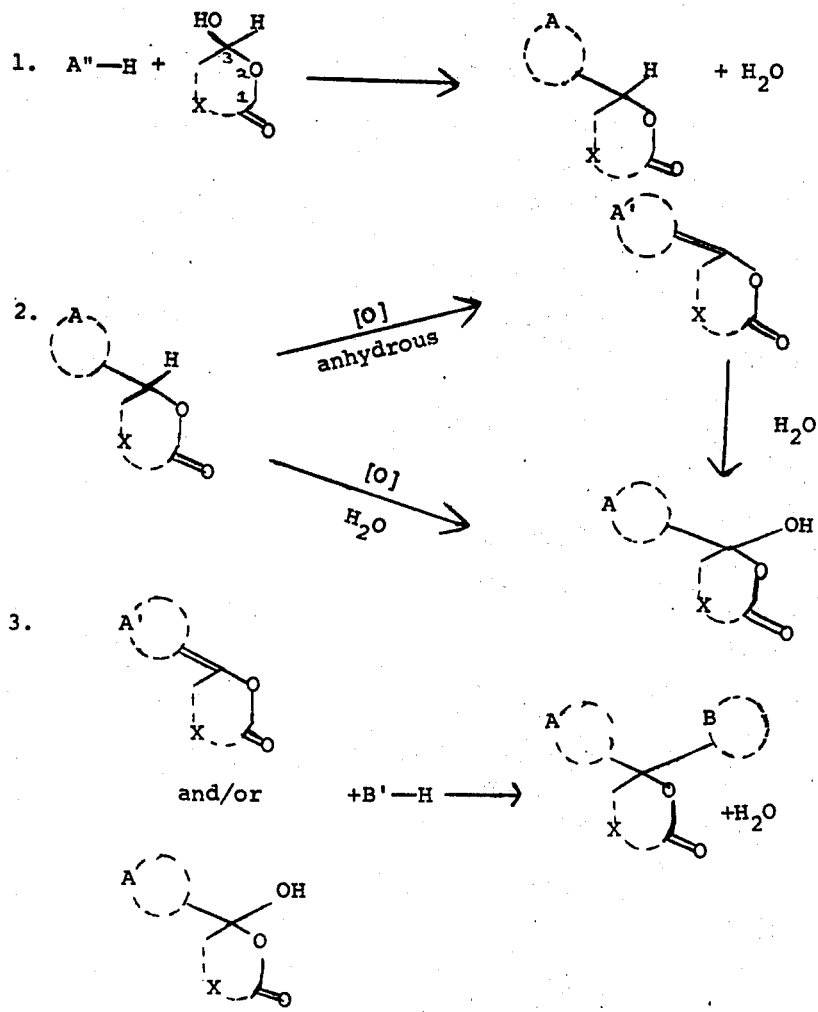

wherein A" represents the starting phenol, naphthol, indole or pyrrole which ultimately comprises the A radical of the indicator dye and B' represents the carbocyclic aryl or heterocyclic aryl compound which This reaction sequence is further illustrated below under the preferred anhydrous conditions using as specific reactants, indole and phthalaldehydic acid to produce 3,3-di-(indole-3-yl) phthalide.

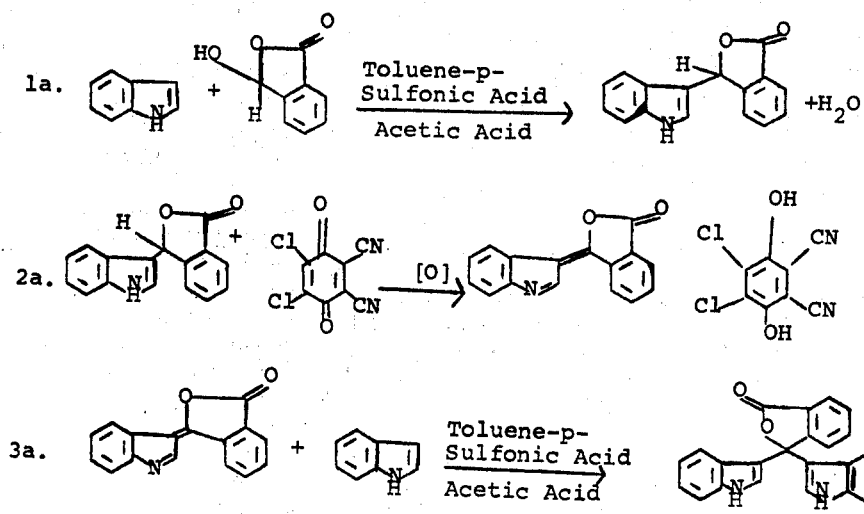

Typical of the indicator dyes that may be prepared according to the present invention are those represented by the following formula:

(I) 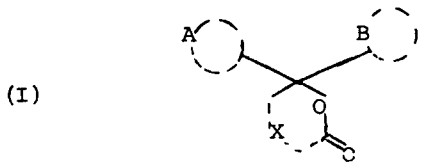

wherein A is a radical selected from p-hydroxyphenyl, p-hydroxynaphthyl, indol-3-yl and pyrr-2-yl, the N atoms of said indolyl and pyrryl radicals being subsituted with hydrogen; B is a radical selected from carbocyclic aryl and heterocyclic aryl; and X represents the carbon atoms necessary to complete a ring-closing moiety selected from phthalide and naphthalide.

In the above formula, the B radical may be carbocyclic aryl of the benzene or naphthalene series, preferably benzene or napthalane containing a para substituent, such as hydroxy, or it may be heterocyclic aryl containing O, N, S, P and combinations thereof, preferably N-heterocyclic aryl, such as indole, pyrrole or carbazole.

The A and/or B radical and/or the ring-closing moiety of the indicator dyes represented above may contain one or more substituents in addition to those specified as may be readily selected by those skilled in the art to achieve certain desired properties.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as, phenyl, 2-hydroxyphenyl, 2-hydroxy-4-dodecyloxyphenyl, and naphthyl; alkaryl, such as benzyl, phenethyl, phenylhexyl, p-octylphenyl, p-dodecylphenyl; alkoxy, such as, methoxy, ethoxy, butoxy, 1-ethoxy-2-(β-ethoxyethoxy), dodecyloxy and octadecyloxy; aryloxy, such as phenoxy, benzyloxy, naphthoxy; alkoxyalkyl, such as methoxyethyl, dodecyloxyethyl; halo such as, fluro, bromo, and chloro; trifluoraklyl, such as trifluoromethyl, mono-and bis-trifuloromethyl carbinol; sulfonamido (—NH—SO₂—R wherein R may be alkyl, aryl, alkaryl); sulfamoyl (—SO₂—NH—R wherein R may be alkyl, aryl, alkaryl); acyl and its derivatives

wherein R' may be hydrogen, alkyl, aryl, alkaryl); aminomethyl (—CH₂—NR'R'' wherein R' and R'' each may be hydrogen, alkyl, aryl, alkaryl); amino

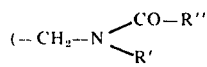

wherein R' and R'' each may be hydrogen, alkyl, aryl, alkaryl); sulfonyl (—SO₂—R wherein R may be alkyl, aryl, alkaryl); sulfo; cyano; nitro; amino including mono-and disubstituted amino, e.g., N-ethyl amino and N,N'-dimethylamino; carboxy; and hydroxyl.

In addition to the above, the substituent may comprise a fused ring bonded to adjacent atoms of the aromatic nucleus. For example, the indoles, pyrroles, phenols and 1-naphthols comprising one or both of the A and B radicals may contain as a substitutent a cycloaliphatic or an aromatic ring usually having 5 or 6 members, carbocyclic or heterocyclic and substituted or unsubstituted, bonded to adjacent carbon atoms of the basic compound, e.g.,

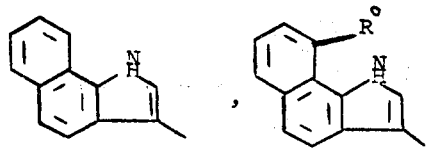

wherein R° is, e.g., —OH os —COOH

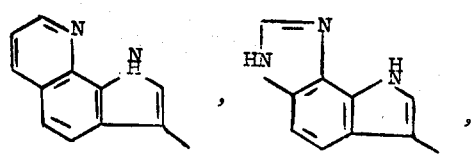

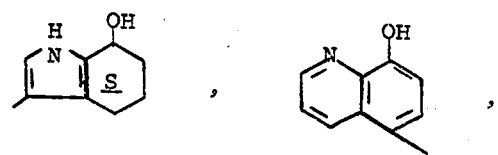

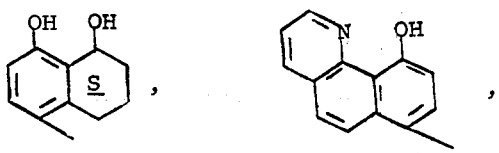

wherein R° is, e.g., —OH or —COOH.

As mentioned previously, the indicator dyes produced in accordance with the present invention may be symmetrical, i.e., di-phthalides or di-napthalides in which instance the B radical would be identical to the A radical, or they may be unsymmetrical or mixed indicators. When unsymmetrical, the B radical and B radical would be derived from the same aromatic compound such as, indole, but each radical would contain different substituents or the same substitutents in different positions or one radical would be substituted and the other unsubstituted. The term "mixed indicator" is intended to denote indicator dyes where the A radical and B radical are derived from different aromatic compounds, for example, one from indole and the other from phenol.

In a preferred embodiment, the method of synthesizing the subject oxidation products and the method of synthesizing indicator dyes therefrom comprises:

1. reacting in substantially equimolar proportions in an inert organic liquid solvent at a temperature between about 20°C. and 120°C., (a) a compound selected from (i) 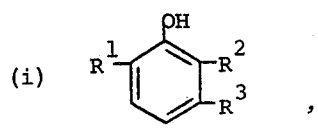

(ii) 

(iii) 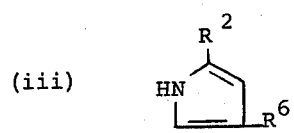

and (iv) 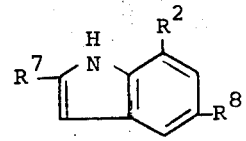

wherein R¹ is selected from hydrogen, alkoxy containing 1 to 3 carbon atoms and alkyl containing 1 to 3 carbon atoms; R² is selected from hydrogen, hydroxy, carboxy, sulfonamido, sulfamoyl, o-hydroxyphenyl, bis-trifluoromethylcarbinol, methoxy, alkyl containing 1 to 16 carbon atoms; R³ is selected from hydrogen, alkoxy containing 1 to 18 carbon atoms and alkyl containing 1 to 3 carbon atoms; R⁴ is selected from hydrogen, hydroxy and carboxy; R⁵ is selected from hydrogen and alkoxy containing 1 to 18 carbon atoms; R⁶ is selected from hydrogen, phenyl, alkyl containing 1 to 3 carbon atoms, and alkoxy containg 1 to 18 carbon atoms; R⁷ is selected from hydrogen, phenyl, o-hydroxyphenyl and alkyl containing 1 to 3 carbon atoms and R⁸ is selected from hydrogen, cyano, carboxy, halo, trifluoromethyl, sulfonyl and alkoxy containing 1 to 18 carbon atoms with (b) and aldehyric acid selected from phthalaldehydic acid, unsubstituted or substituted in one of the 4- or 7-positions with carboxy and napthalaldehydic acid, unsubstituted, to form the corresponding adduct having the formula:

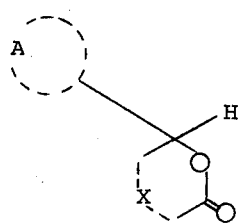

wherein A is a radical selected for p-hydroxyphenyl, p-hydroxynaphthyl, pyrr-2-yl and indol-3-yl corresponding to said (i), (ii) (iii) and (iv), respectively, and X represents the carbon atoms necessary to complete a ring-closing moiety selected from phthalide, unsubstituted or substituted in the 4- or 7-position with carboxy, and naphthalide, unsubstituted; and 2. reacting said adduct with a quinone selected from choranil, o-chloranil and 2,3-dichloro-5,6-dicyano-1,4-benzoquinone in a molar ratio of about 1.1 to 1.5 moles of quinone per 1.0 mole of adduct in an inert organic liquid solvent at a temperature between about 20°C. and 200°C. to form the corresponding oxidation product.

To prepare the indicator dye product, the oxidation product of step (2) is reacted with a compound selected from (i), (ii), (iii) and (v) as defined in (a) above in substantially equimolar proportions in an inert organic liquid solvent at a temperature between about 20°C. and 120°C. in the presence of an acid catalyst to form the corresponding 3,3-disubstituted phthalide or naphthalide.

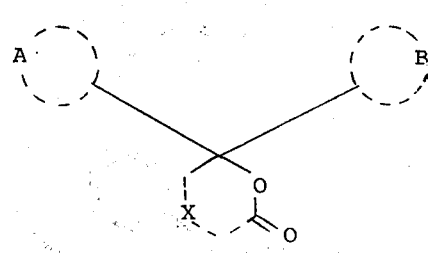

wherein A and B each is a radical selected from p-hydroxyphenyl, p-hydroxynaphthyl, pyrr-2-yl, and indol-3-yl corresponding to said (i), (ii), (iii) and (iv), respectively, and X represents the carbon atoms necessary to complete a ring-closing moiety selected from phthalide, unsubstituted or substituted in the 4- or 7-position with carboxy and naphthalide, unsubstituted.

In a particularly preferred embodiment, the process of the present invention are employed in the synthesis of phthalides and naphthalides wherein the radicals A and B of the dye product are both p-hydroxyphenyl, p-hydroxynaphthyl, etc., either symmetrical or unsymmetrical and especially such dyes and dye intermediates wherein the R² group(s) forms a 5-, 6- or 7-membered intramolecular hydrogen-bonded ring with the functional —OH of the p-hydroxycarbocyclic aryl radical of the —NH— of the N-heterocyclic aryl radical and which contains a heteroatom selected from O, N and S. Preferably, the heteroatom has attached to it a proton more acidic than the proton on the —OH or —NH— and ionizes in basic solution to a negative charge to form the intramolecular hydrogen bond with the adjacent —OH or —NH—. Examples of such groups found particularly useful in preparing high pKa indicator dyes are carboxy, hydroxy, or o-hydroxyphenyl, bis-trifluoromethyl carbinol, sulfonamido and sulfamoyl. Such phthalide and naphthalide indicator dyes include those where at least one of the R² groups of the di-phenol, di-naphthol, di-pyrrole and di-indole dyes is a hydrogen-bonding group, for example, di-phenol indicators wherein R² on one or both of the phenolic radicals is a hydrogen-bonding group; di-naphthol indicators wherein R² on one of the naphtholic radicals is a hydrogen-bonding group and R⁴ is hydrogen and on the second naphtholic radical, R² is hydrogen; di-pyrrole indicators wherein R² on one or both of the pyrr-2-yl radicals is a hydrogen-bonding group; and di-indole indicators wherein R² on one of the indol-3-yl radicals is a hydrogen-bonding group, and R⁷ is hydrogen and on the second indol-3-yl radical, R⁷ is hydrogen and R² is a hydrogen-bonding group and R⁸ is hydrogen, alkoxy or an electron-withdrawing group, i.e., a group having a positive sigma value as defined by Hammett's Equation, such as, carboxy, cyano, halo, sulfonyl and trifluoromethyl.
Examples of specific indicator dyes that may be prepared according to the present invention include:
(1) 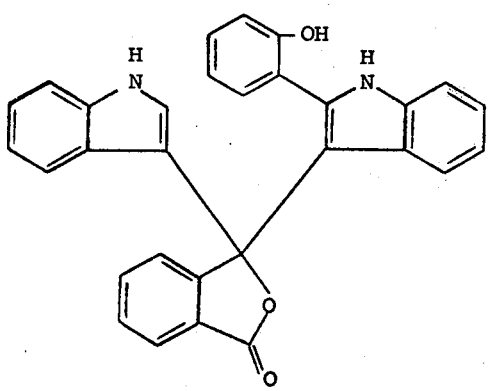
(2) 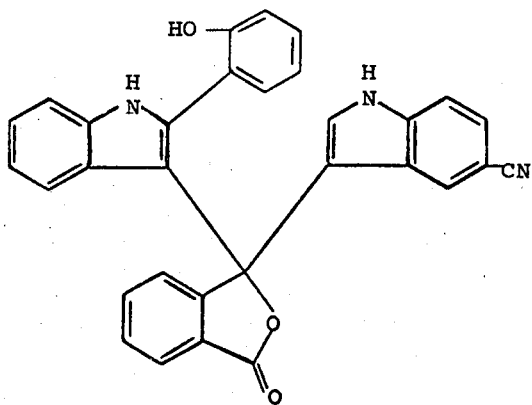
(3) 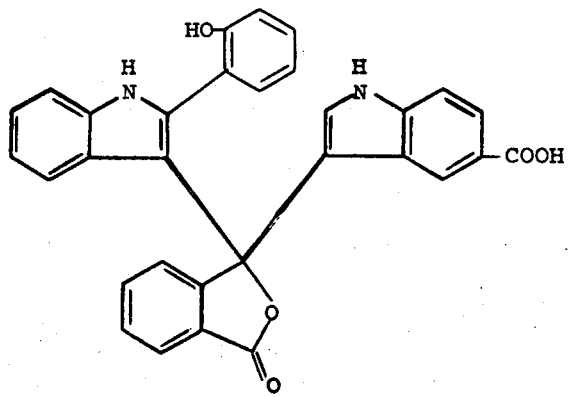
(4) 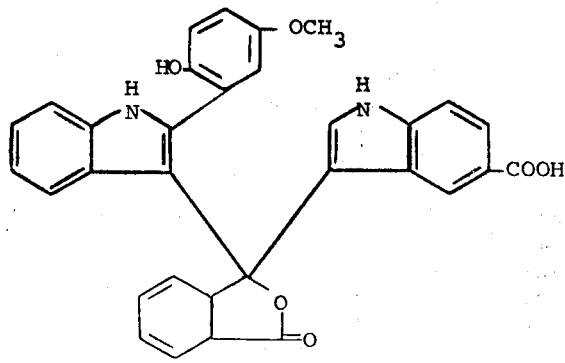

(5)
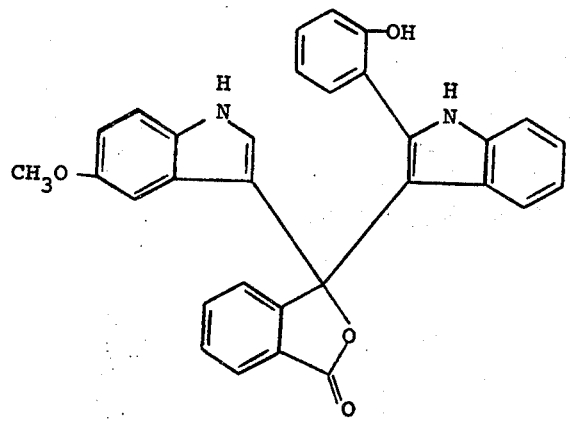
(6)
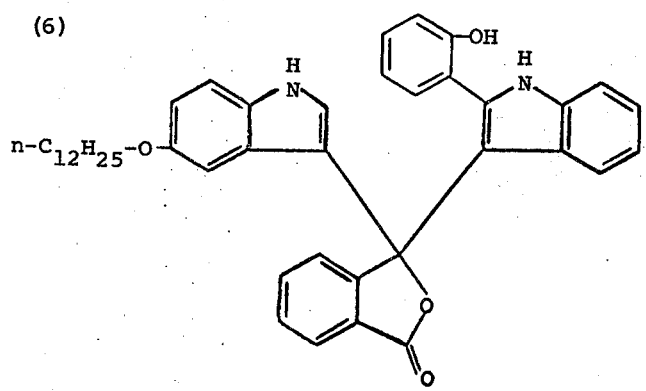
(7)
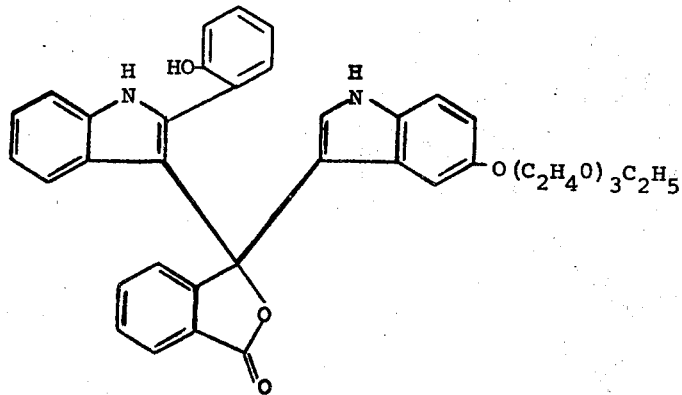
(8)
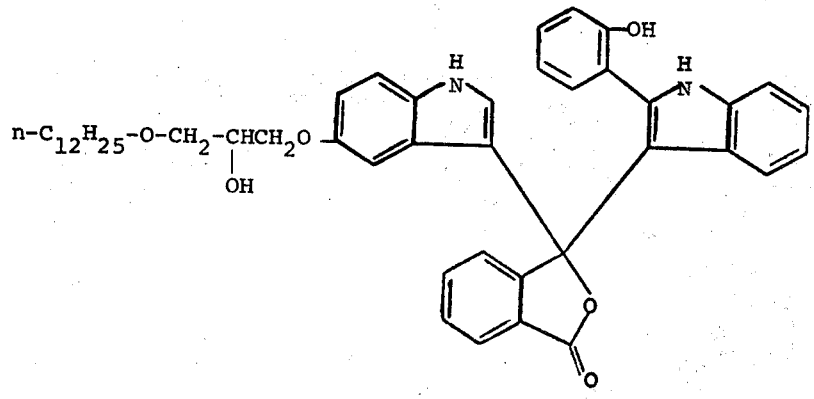

(9)
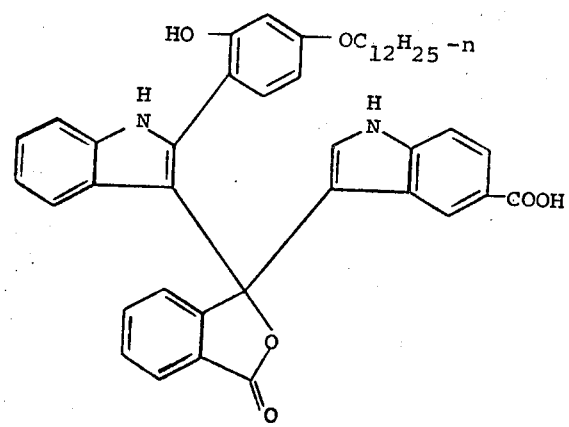
(10)
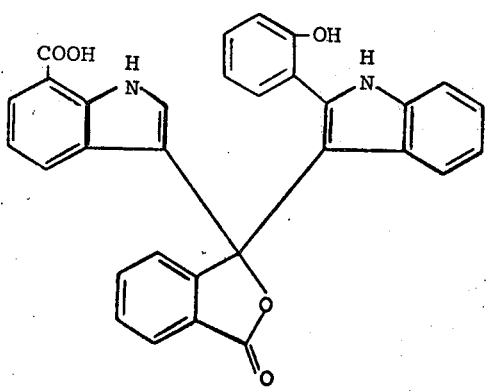
(11)
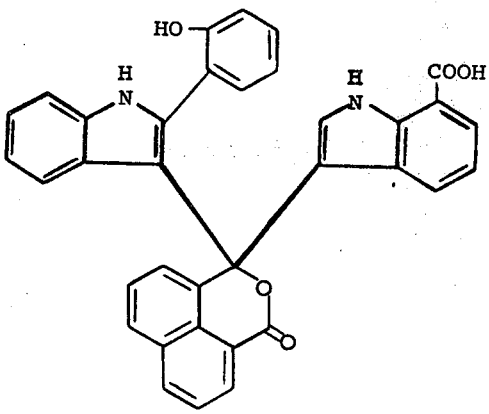
(12)
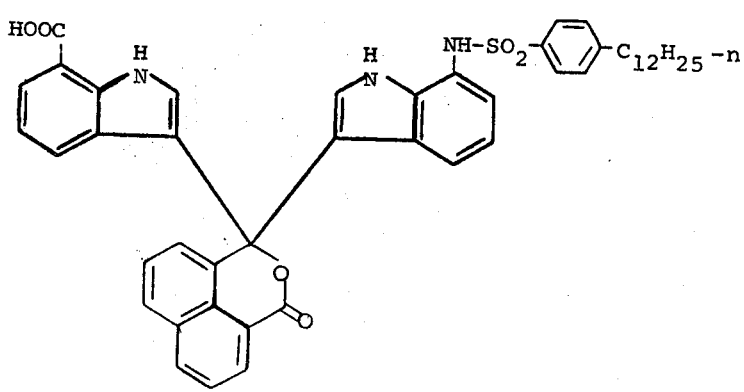

(13) 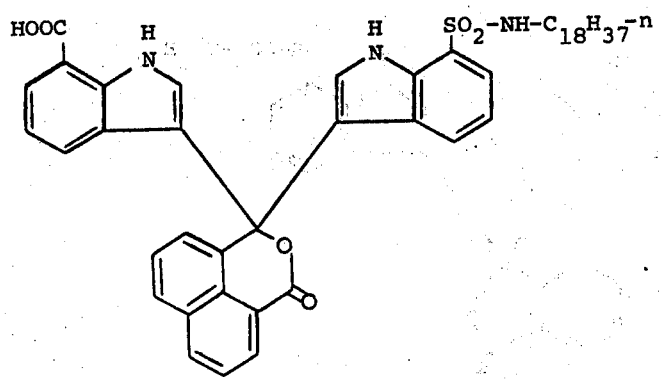
(14) 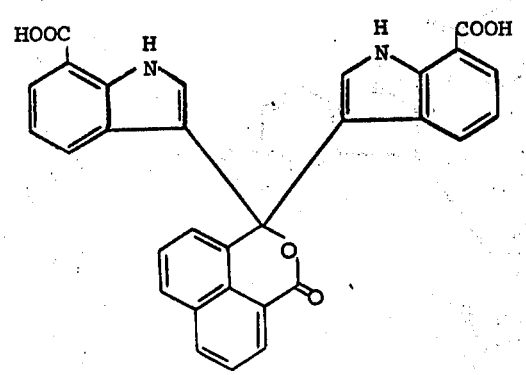
(15) 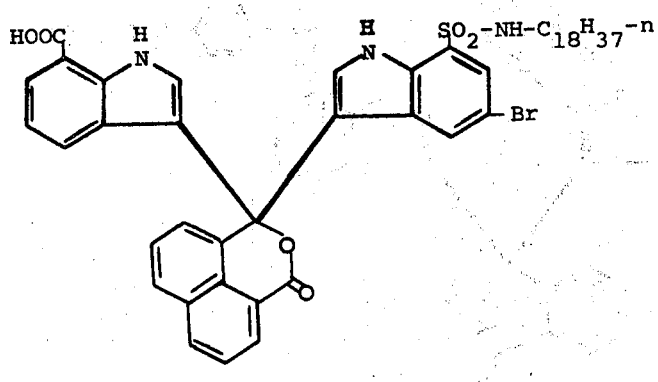
(16) 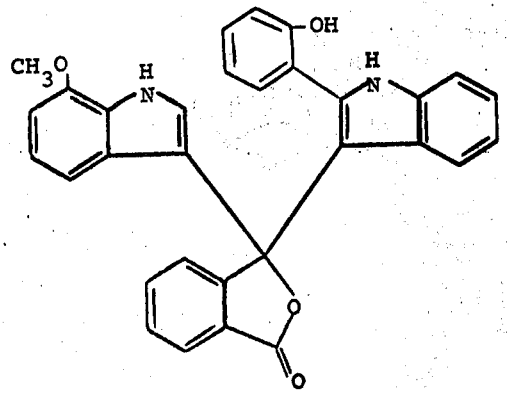

(17) 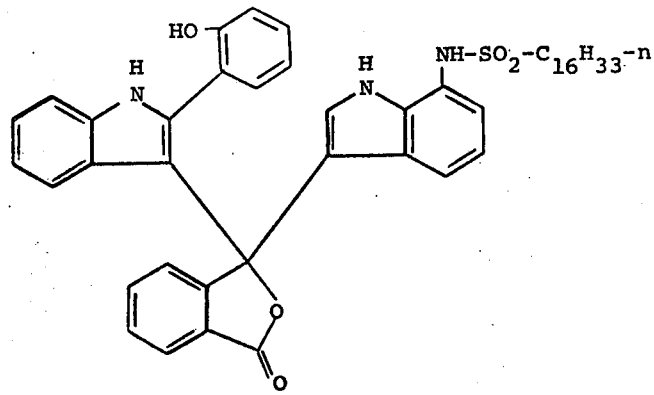
(18) 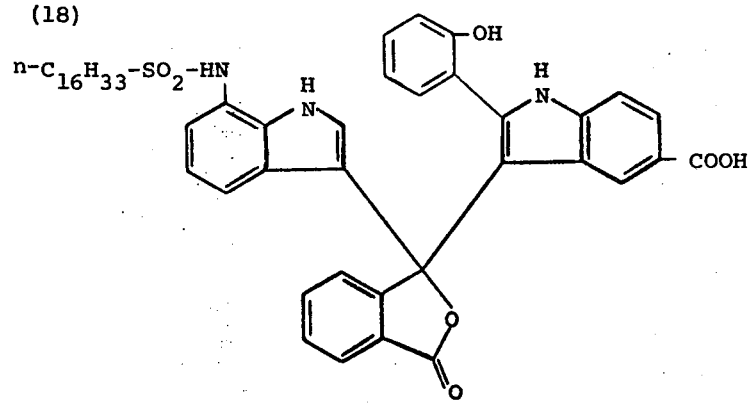
(19) 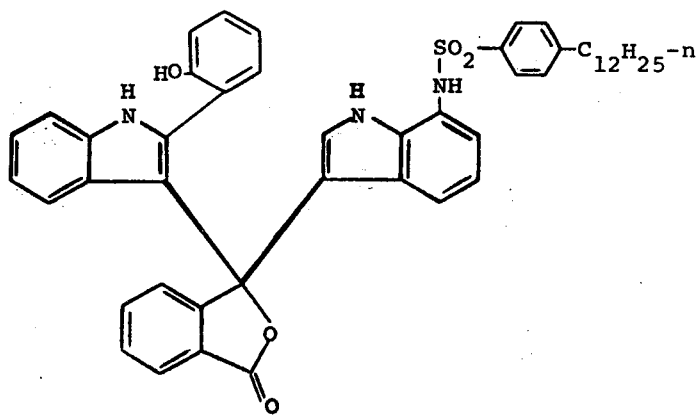
(20) 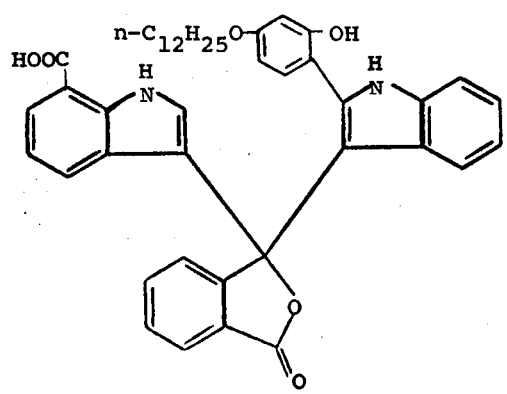

(21) 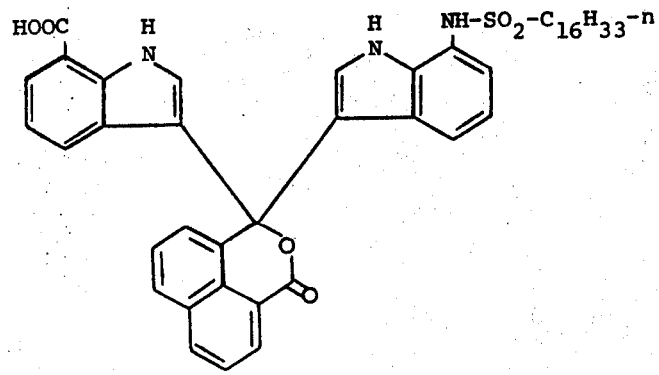
(22) 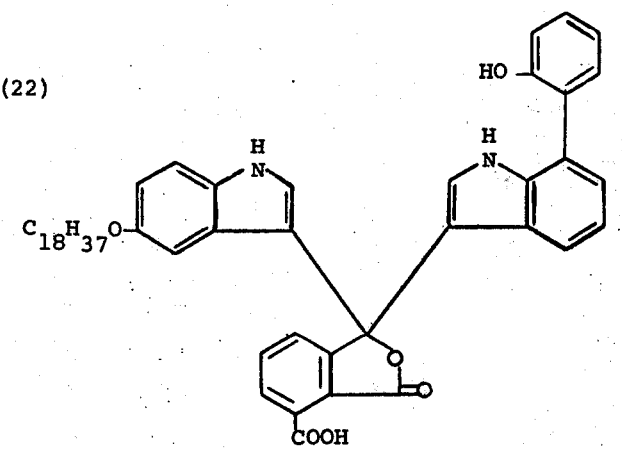
(23) 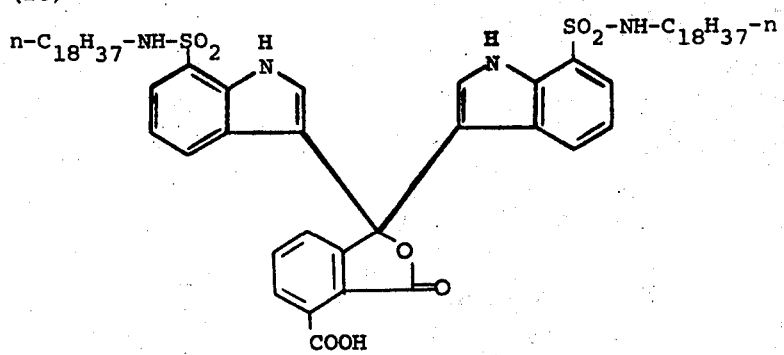
(24) 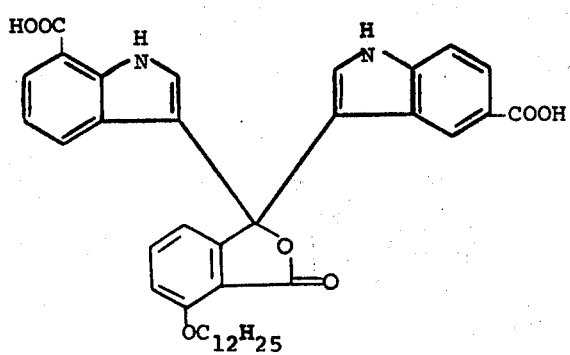

(25)
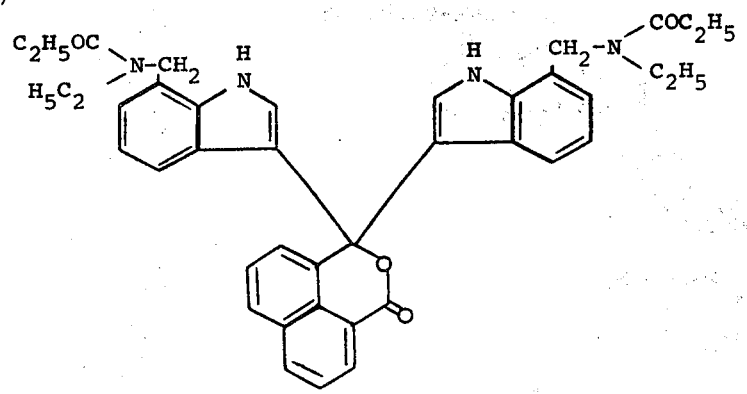
(26)
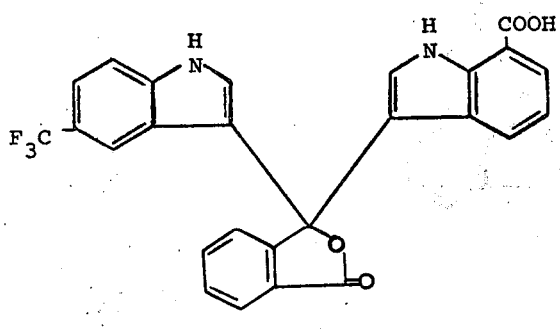
(27)
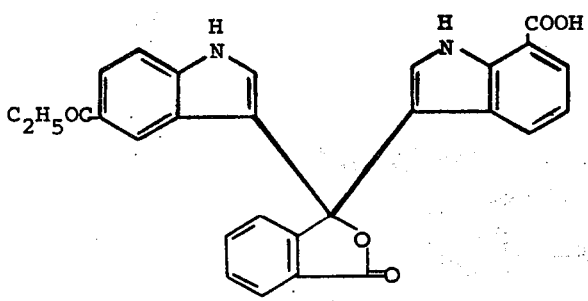
(28)
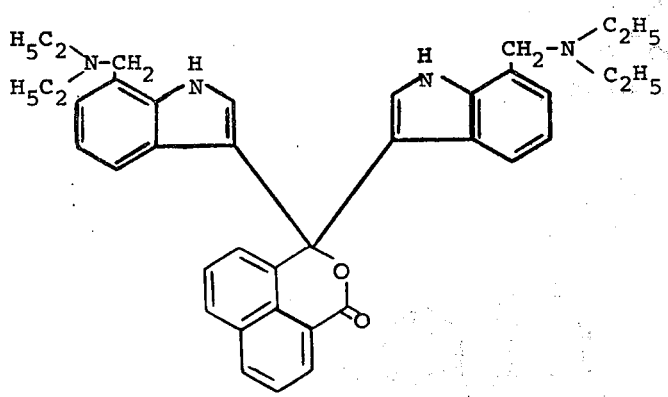
(29)
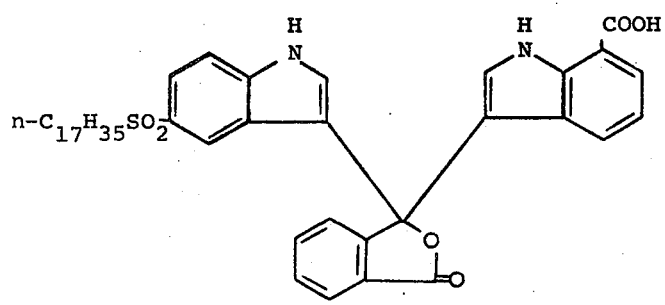

(30)
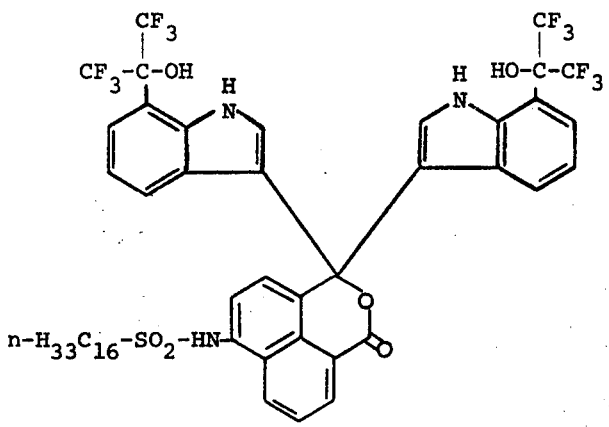
(31)
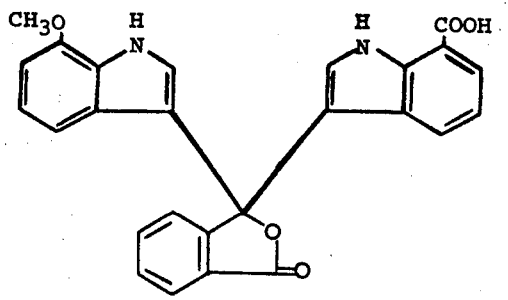
(32)
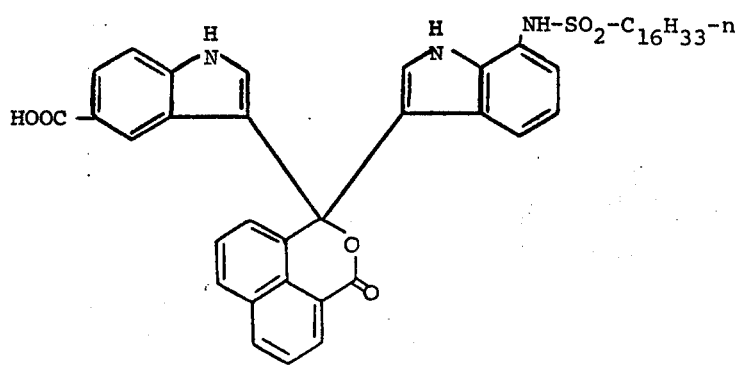
(33)
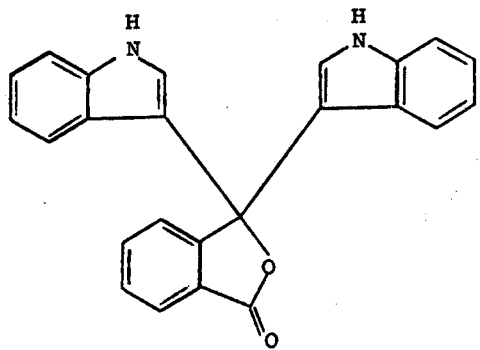

(34)
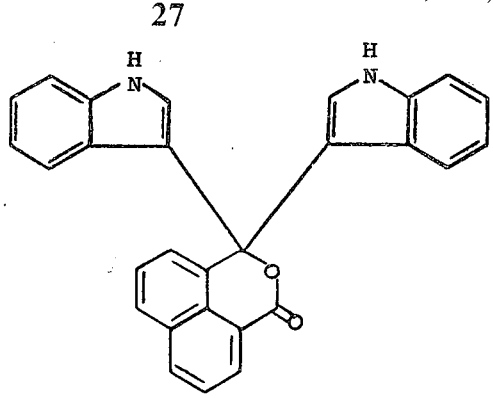
(35)
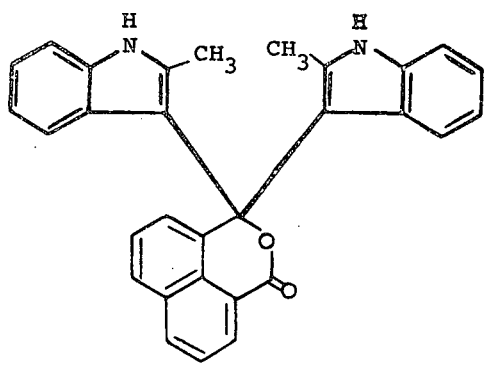
(36)
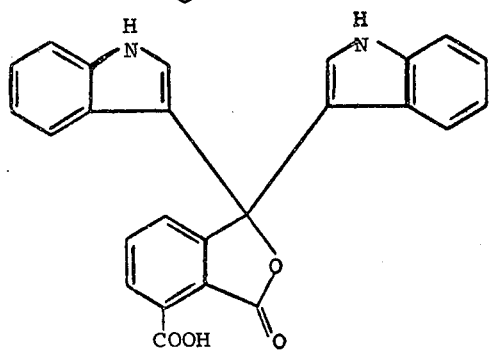
(37)
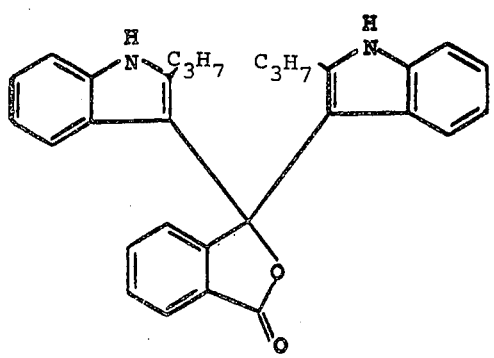
(38)
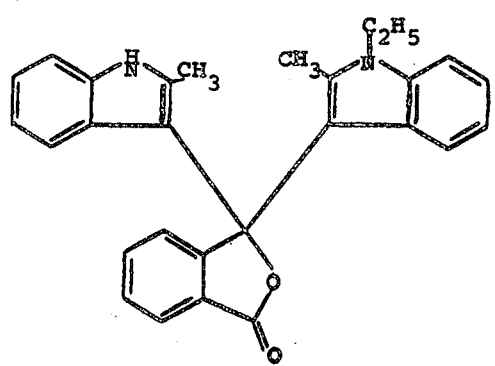

(39)
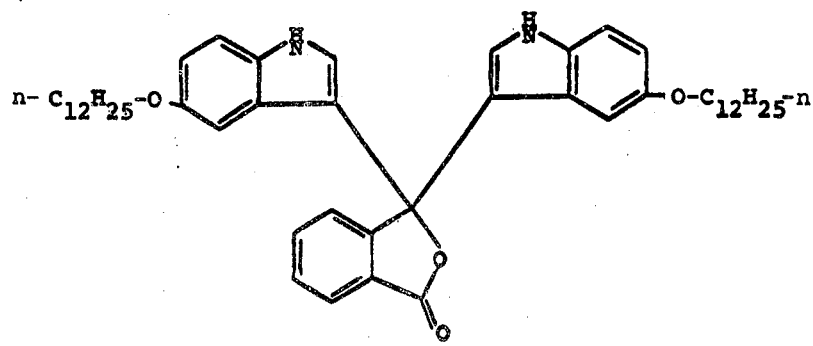
(40)
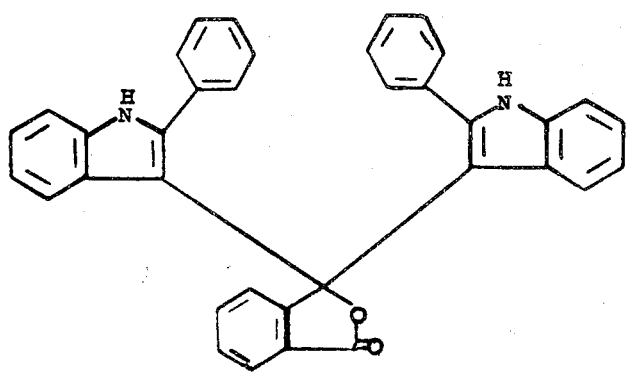
(41)
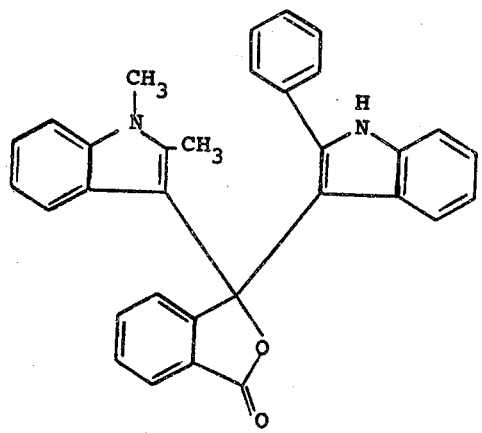
(42)
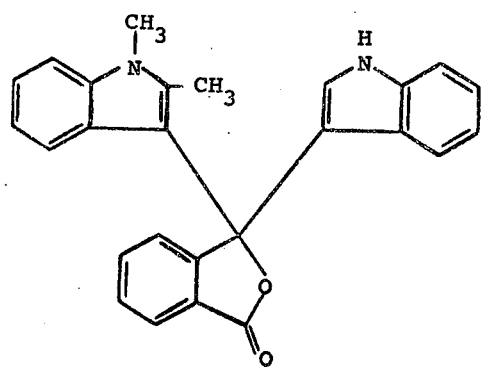

(43) 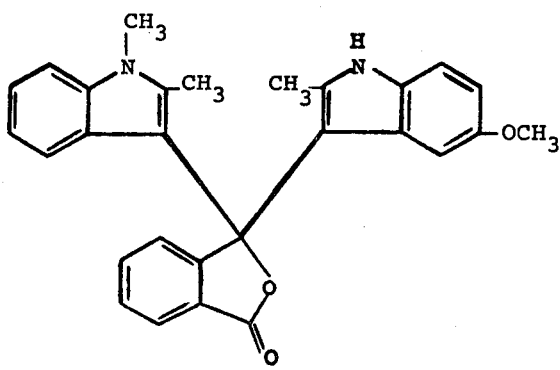
(44) 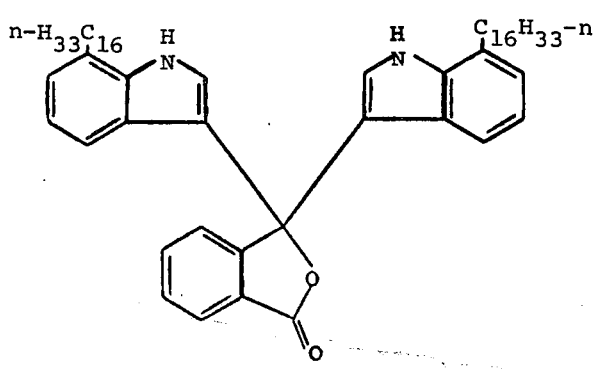
(45) 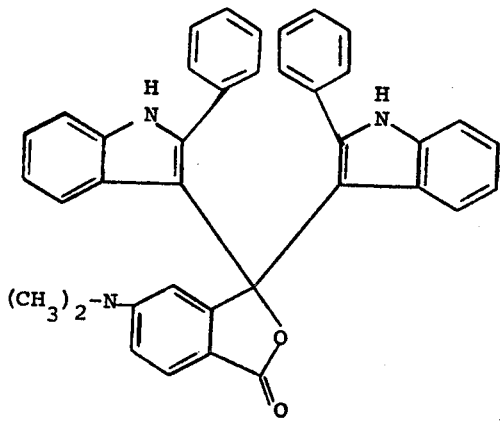
(46) 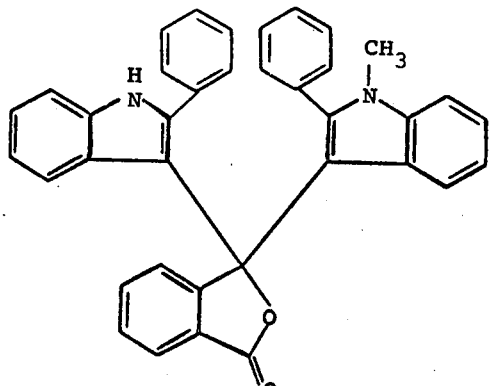
(47) 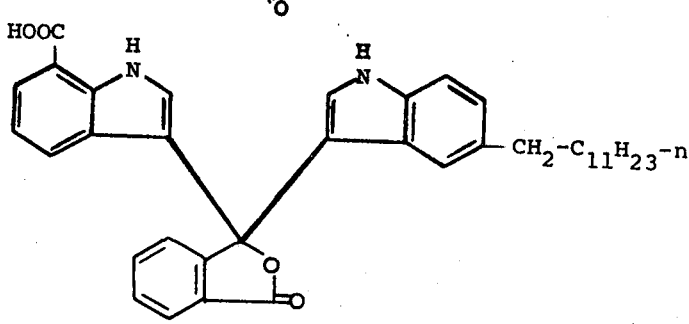

(48) 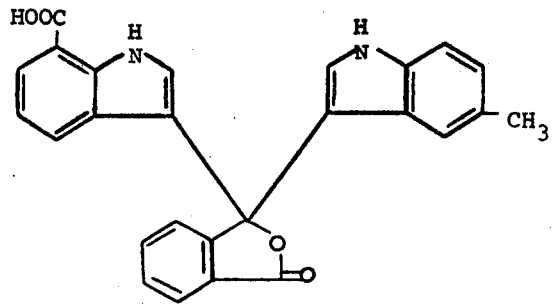
(49) 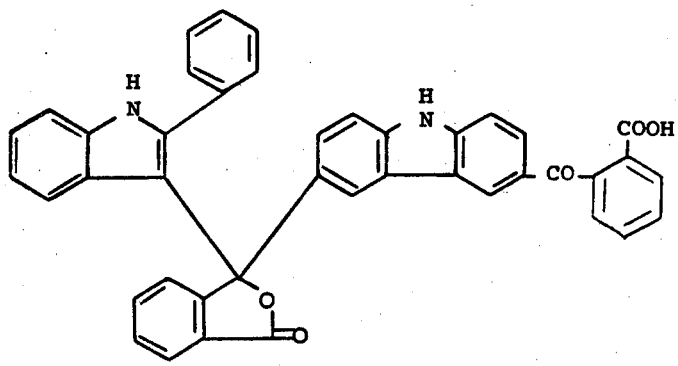
(50) 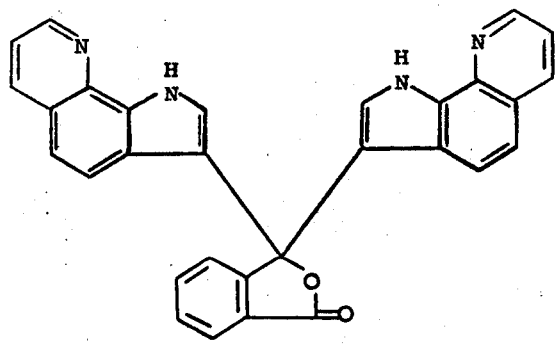
(51) 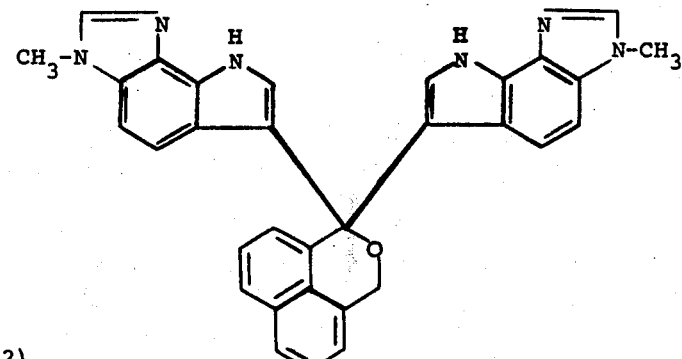
(52) 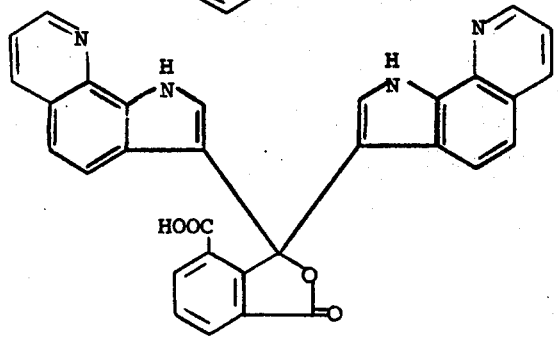

(53) 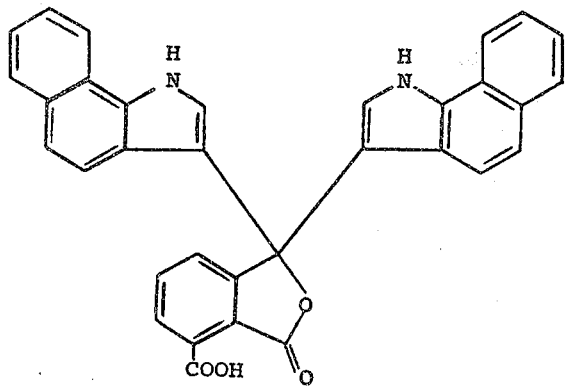
(54) 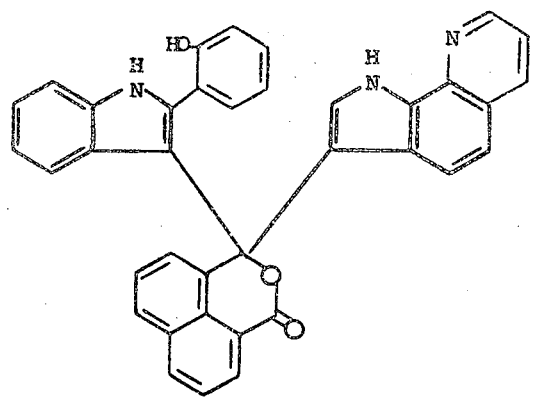
(55) 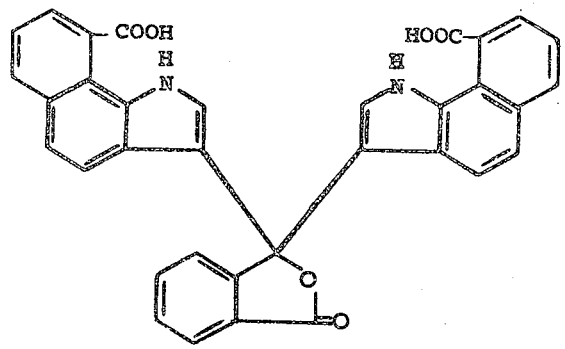
(56) 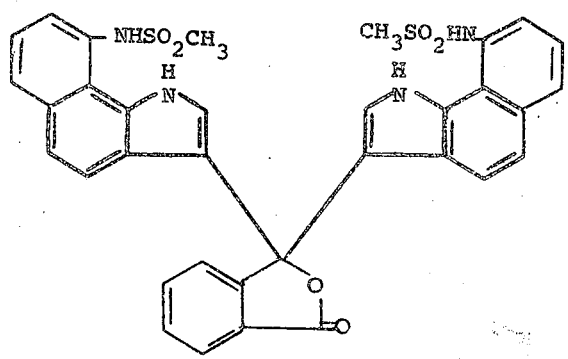
(57) 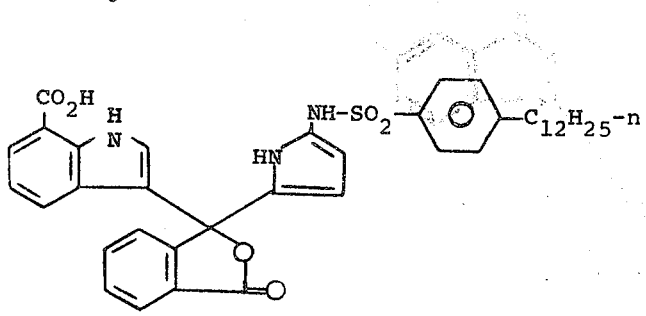

(58)
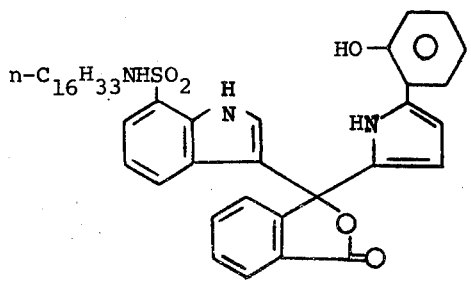
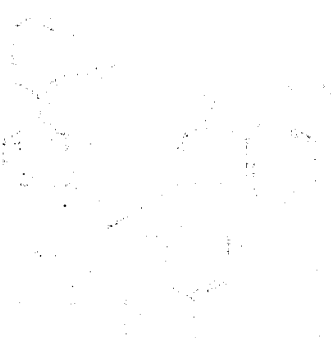
(59)
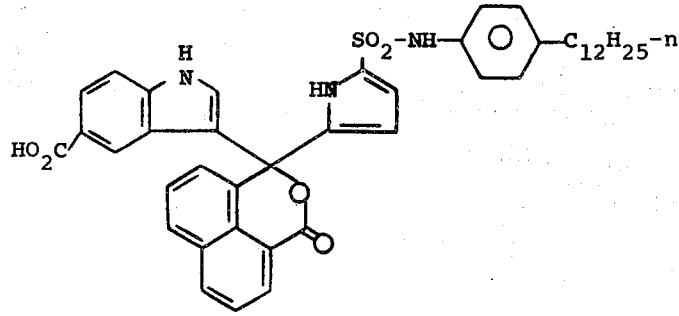
(60)
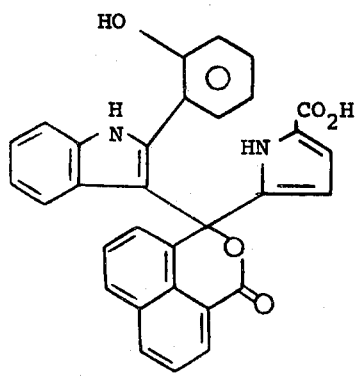
(61)
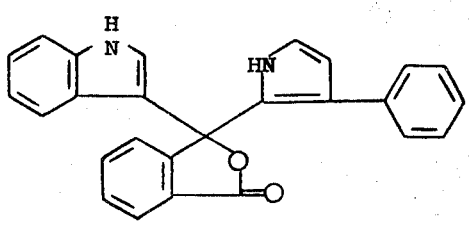
(62)
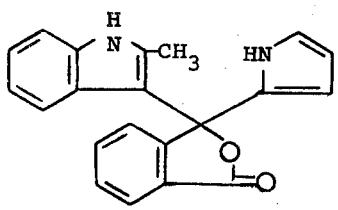

(63) 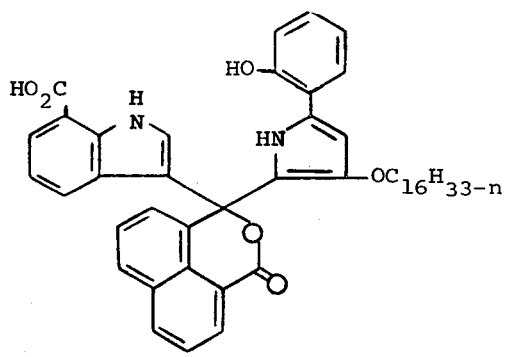
(64) 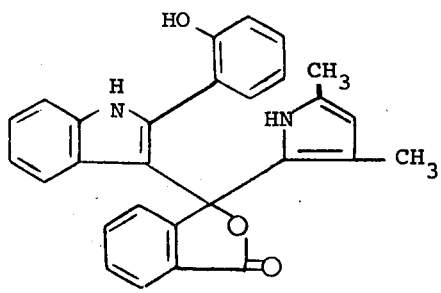
(65) 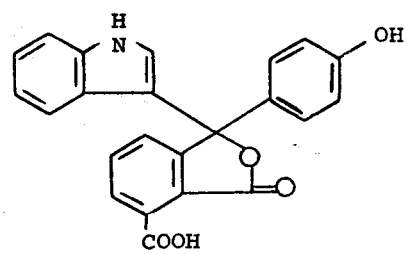
(66) 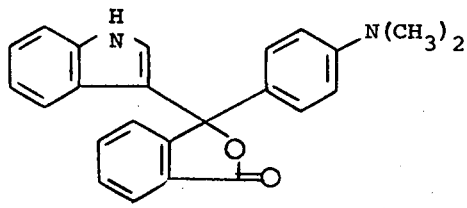
(67) 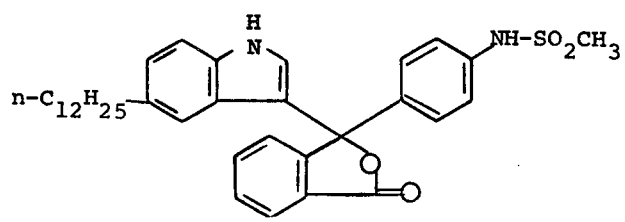

(68) 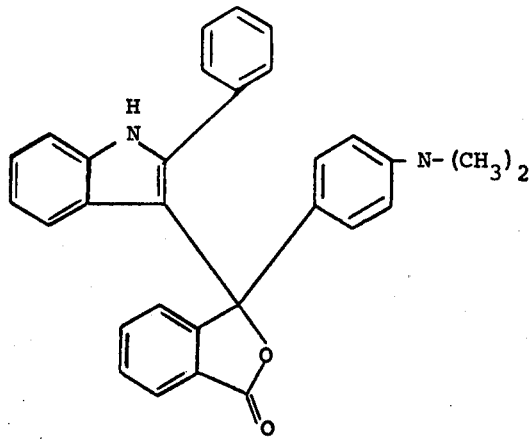
(69) 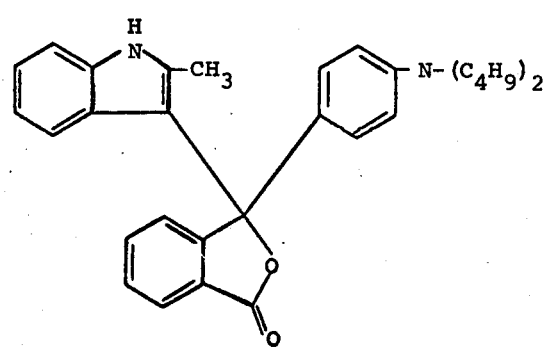
(70) 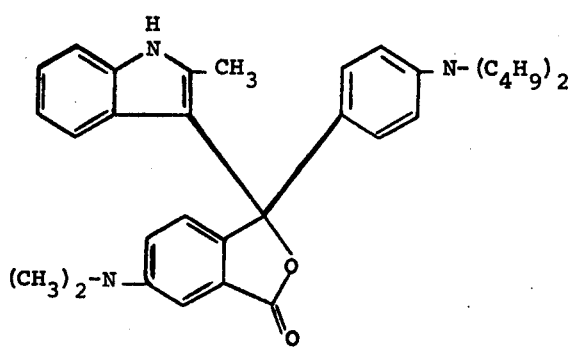
(71) 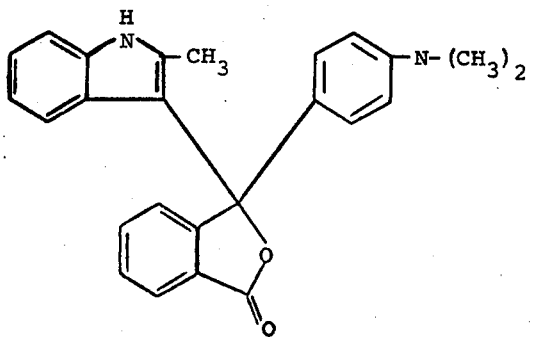
(72) 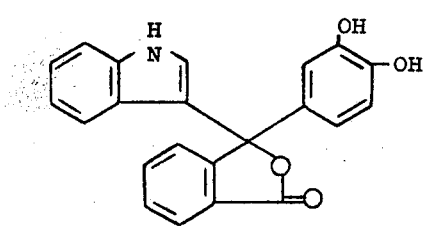

(73) 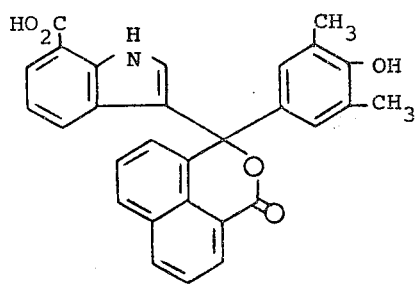
(74) 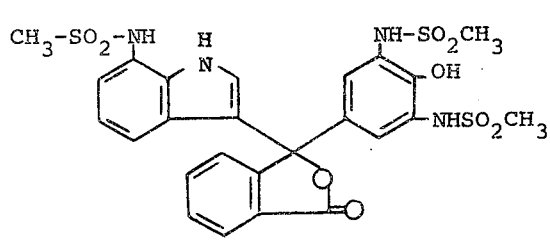
(75) 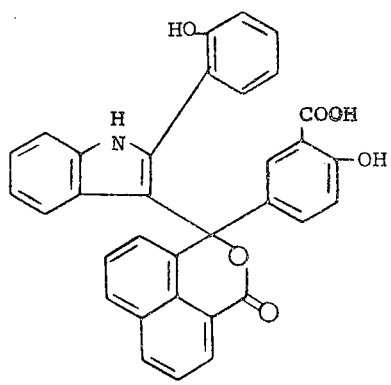
(76) 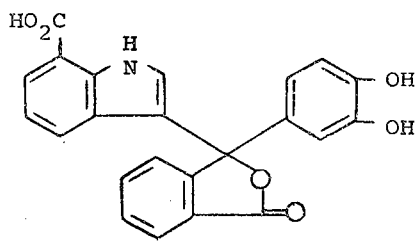
(77) 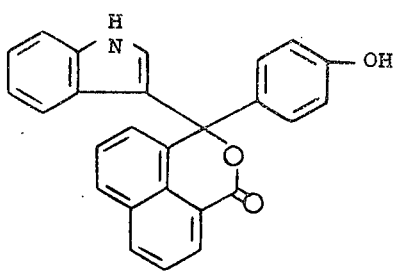

(78)
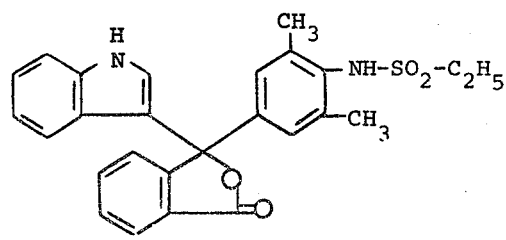
(79)
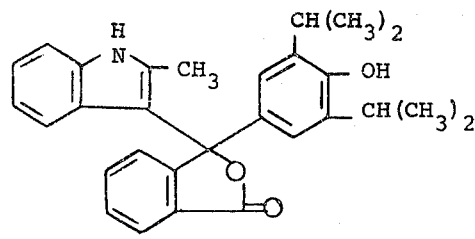
(80)
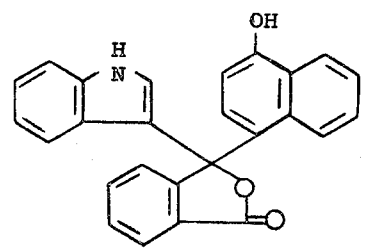
(81)
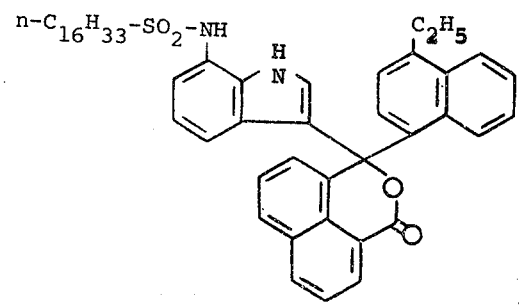
(82)
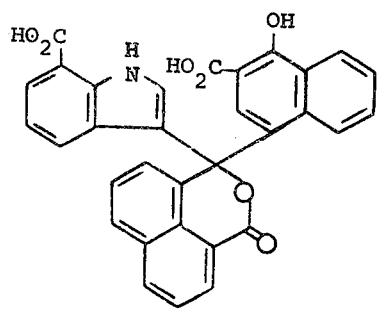

(83) 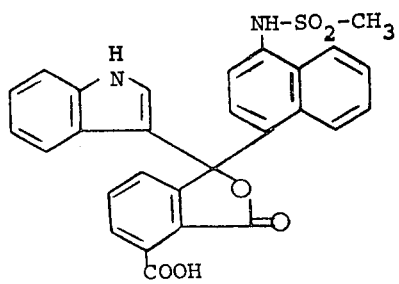
(84) 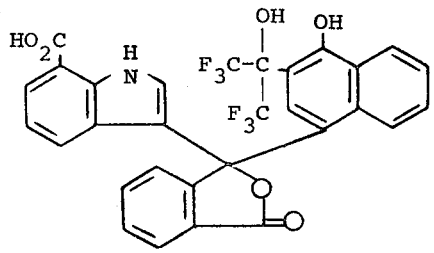
(85) 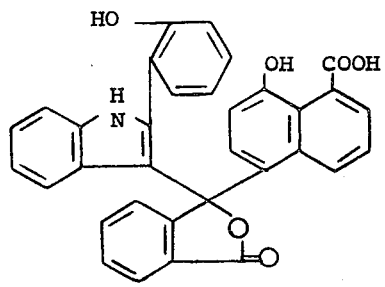
(86) 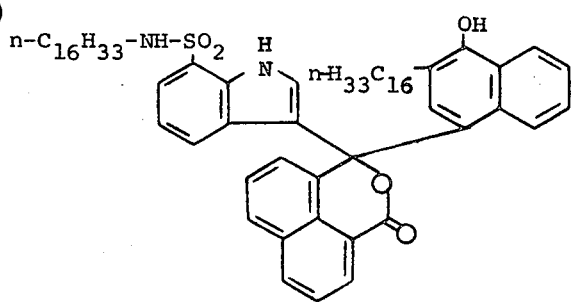
(87) 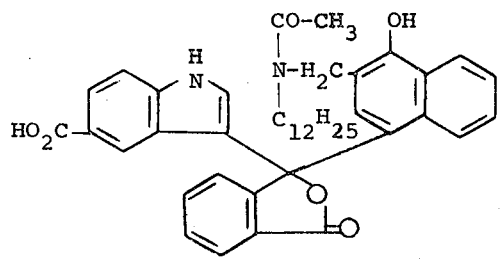
(88) 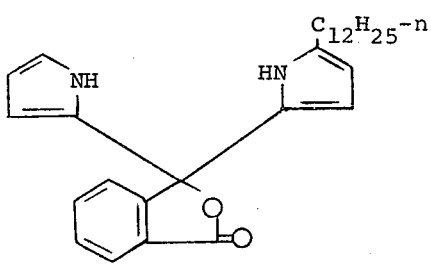

(89)
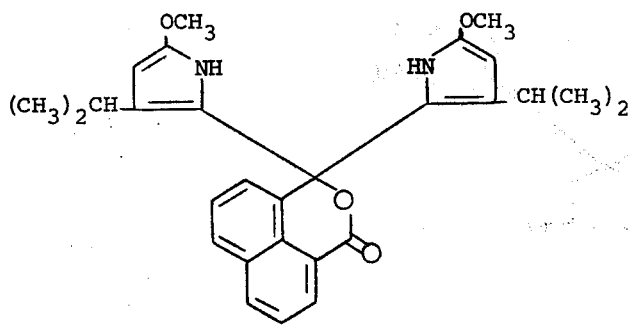
(90)
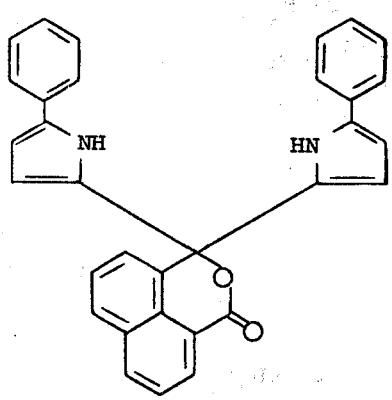
(91)
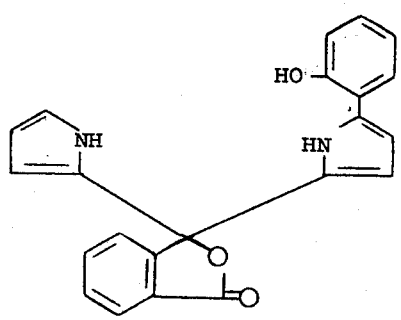
(92)
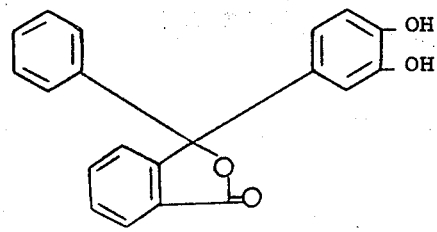
(93)
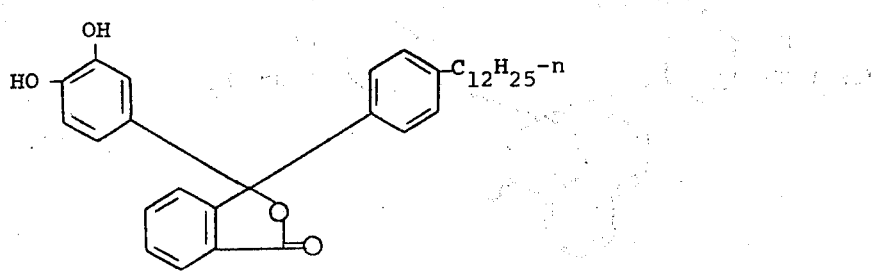

(94)
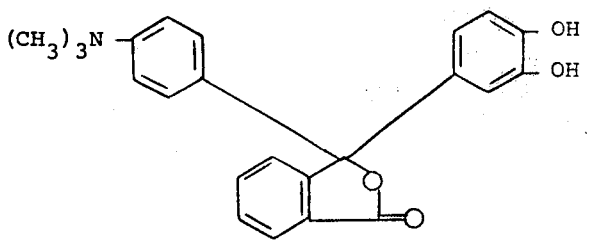
(95)
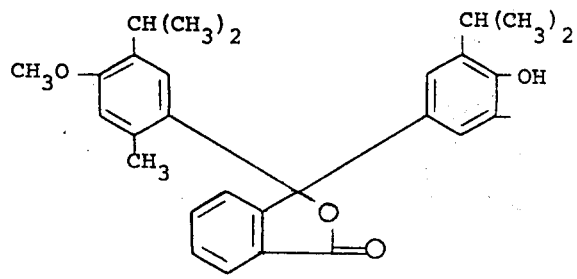
(96)
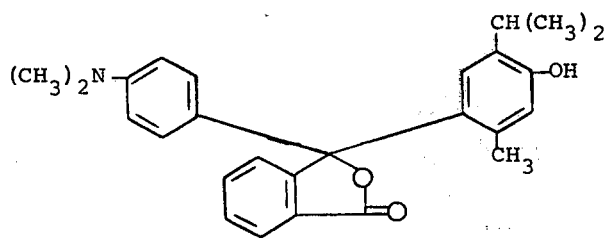
(97)
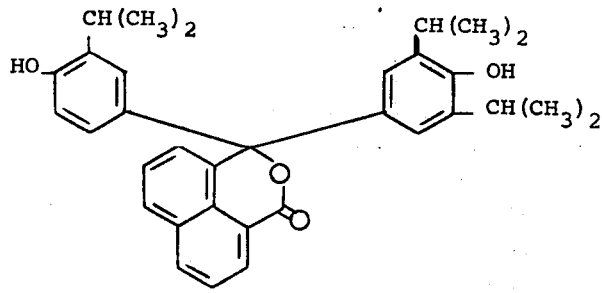
(98)
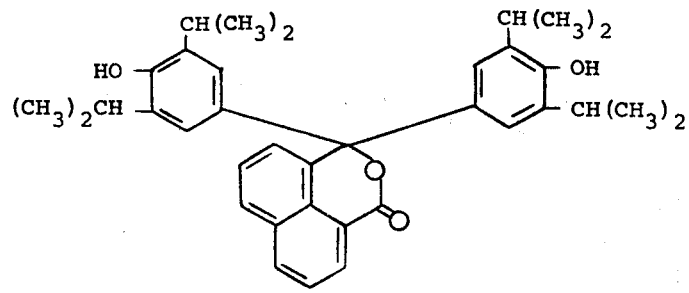

(99) 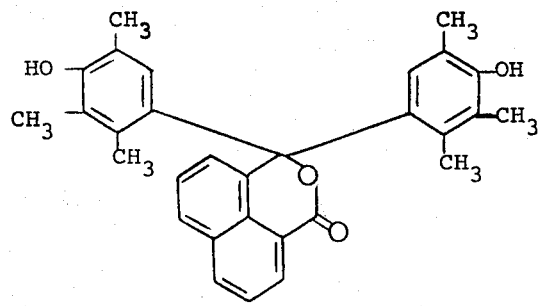
(100) 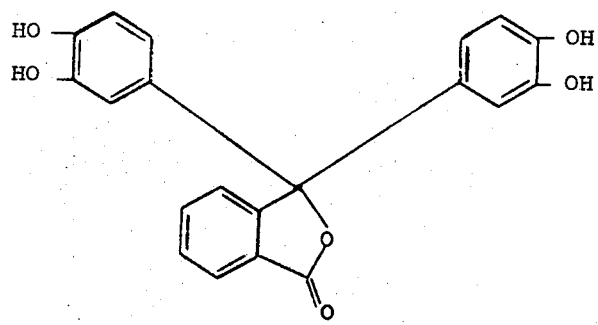
(101) 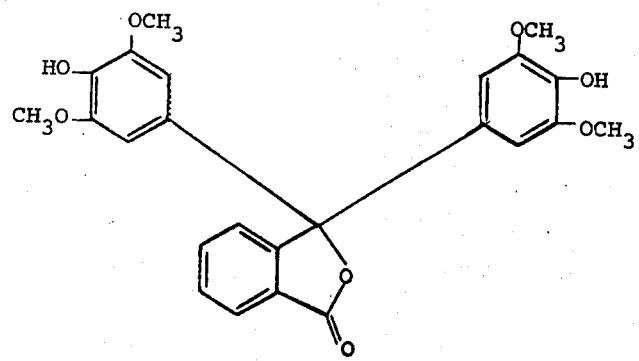
(102) 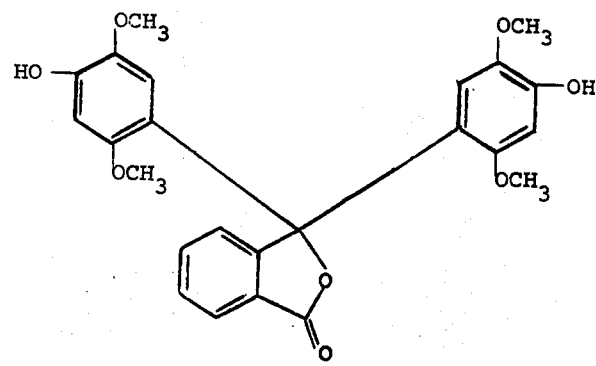
(103) 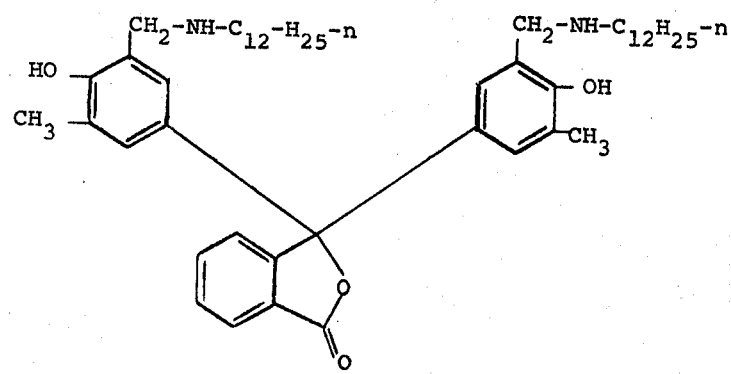

(104) 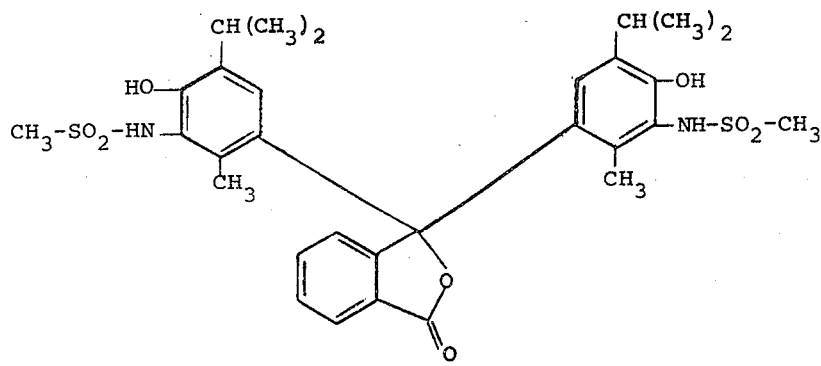
(105) 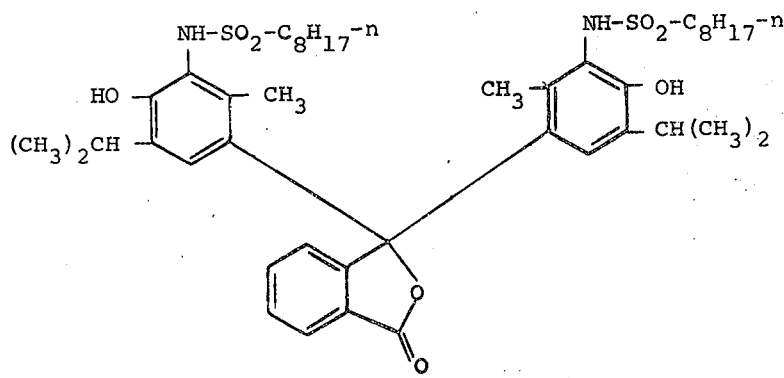
(106) 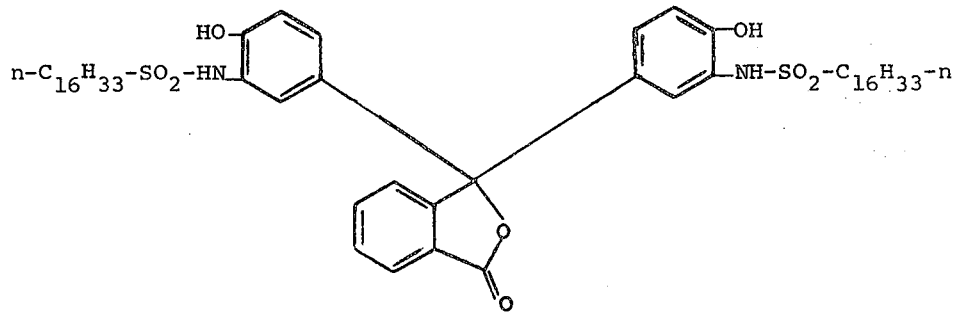
(107) 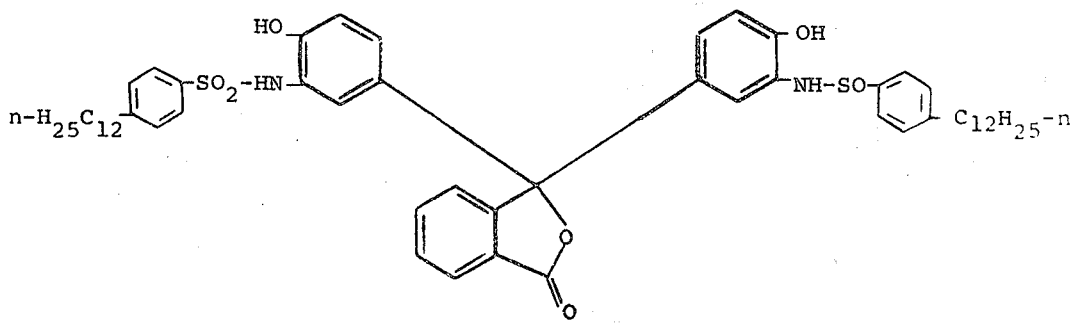
(108) 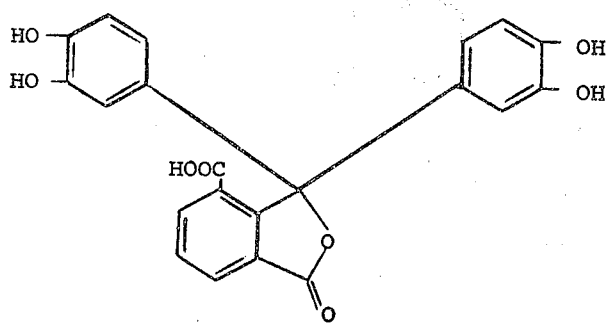

(109) 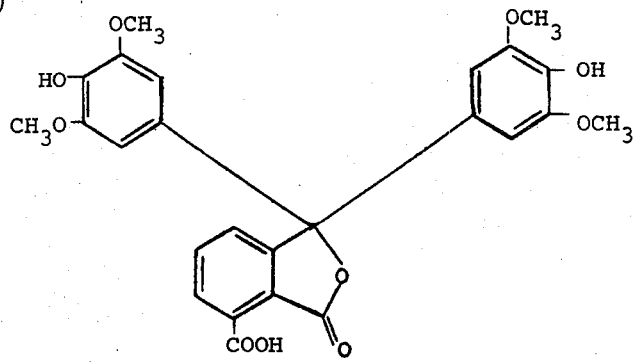
(110) 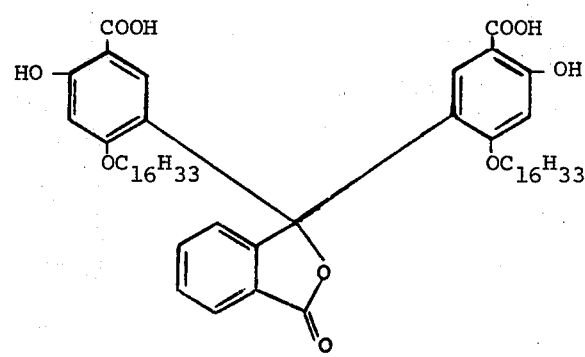
(111) 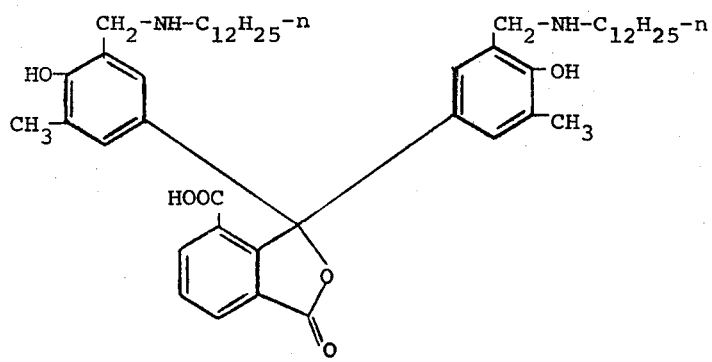
(112) 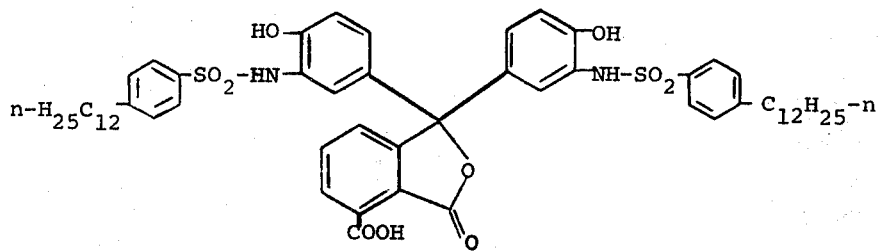
(113) 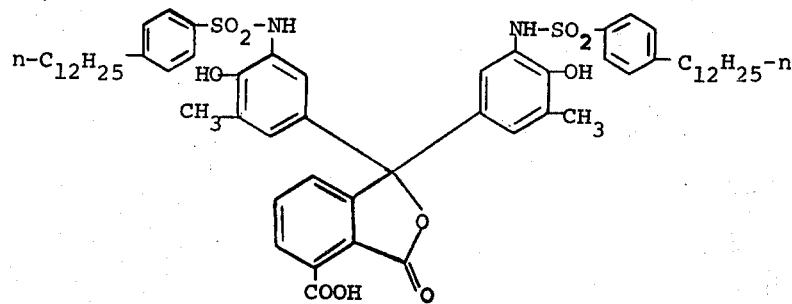

(114)
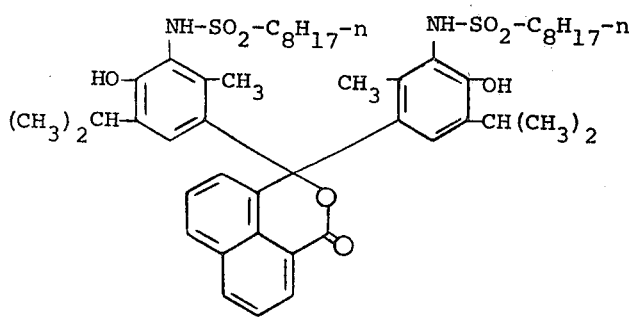
(115)
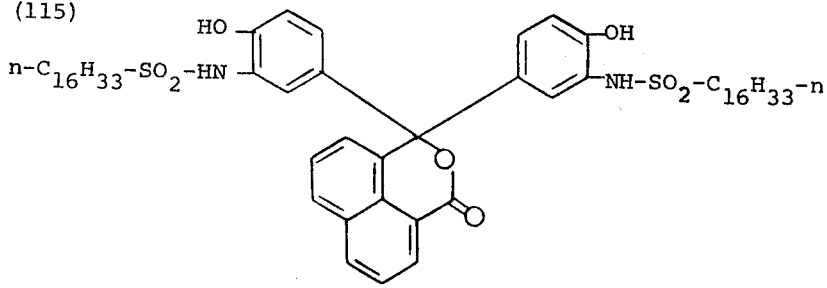
(116)
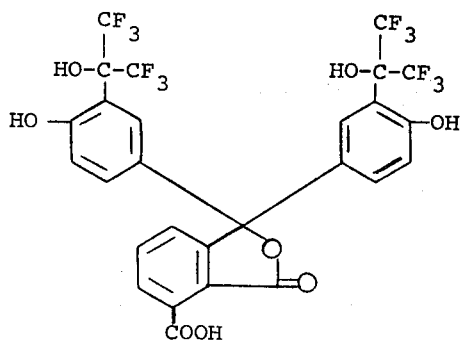
(117)
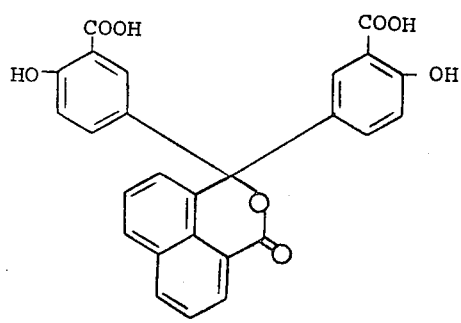
(118)
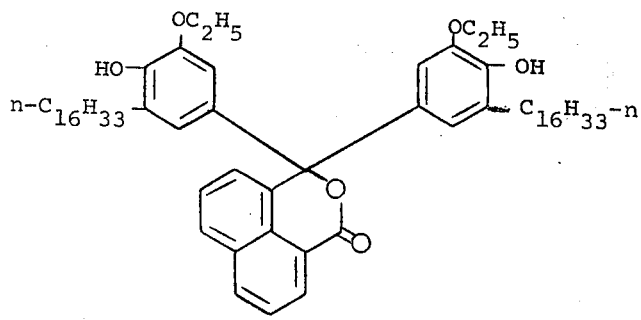

(119) 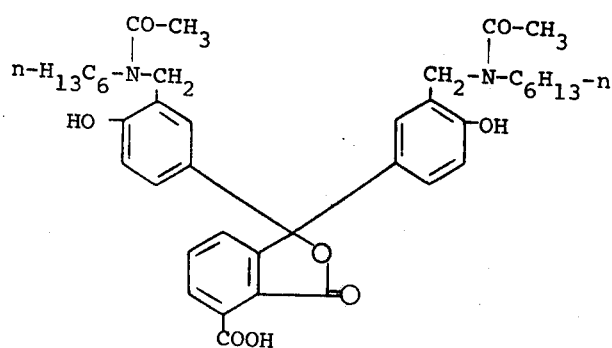
(120) 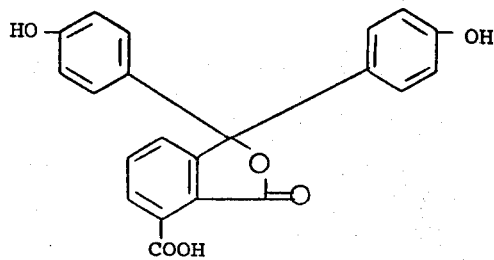
(121) 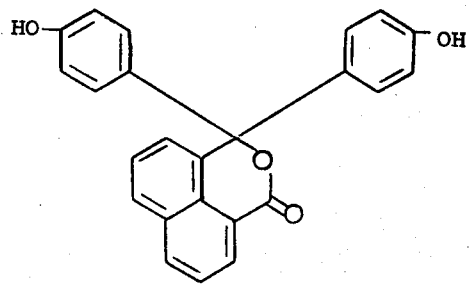
(122) 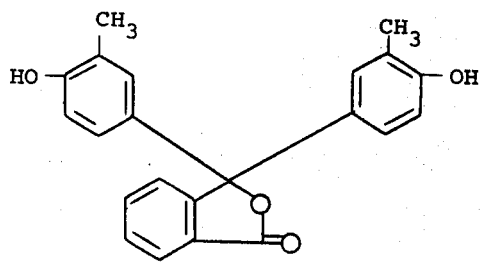
(123) 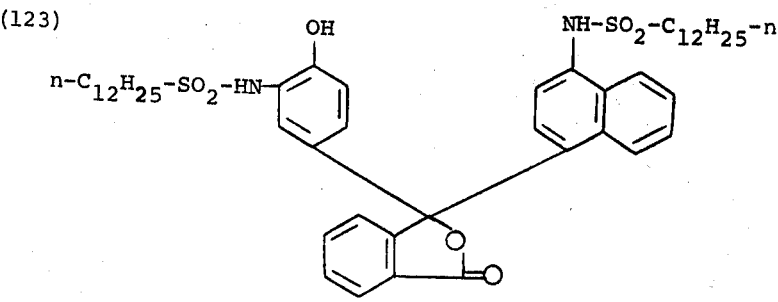

(124) 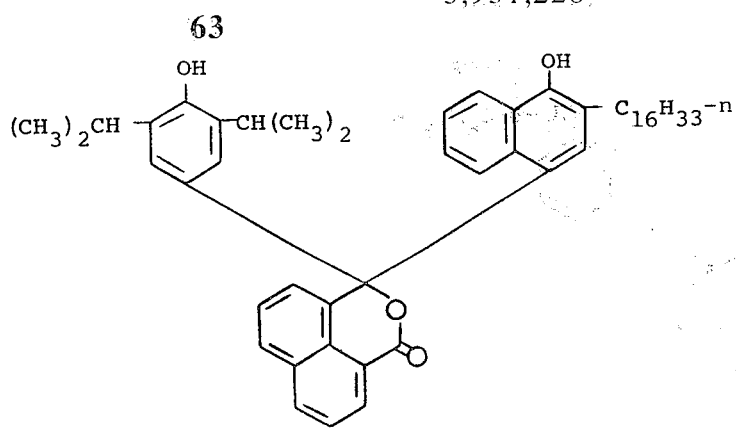
(125) 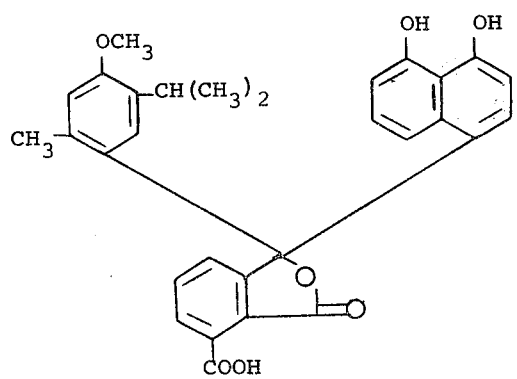
(126) 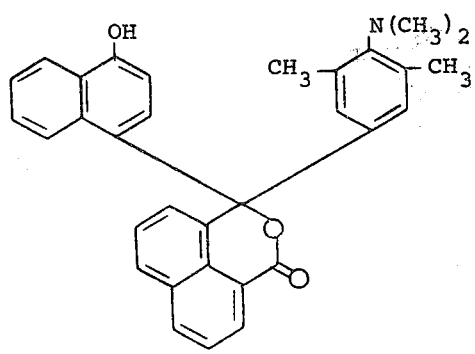
(127) 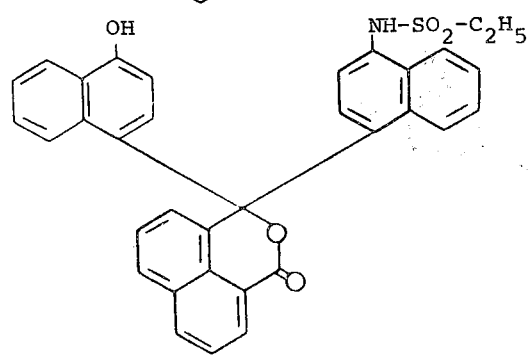
(128) 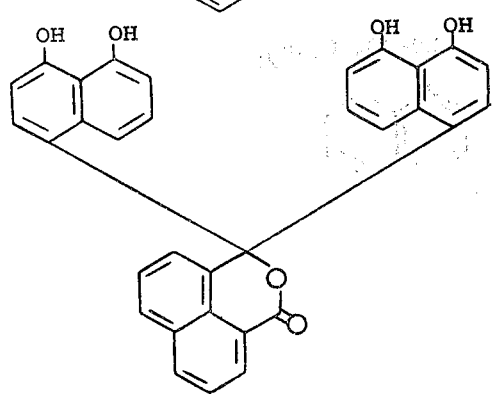

(129) 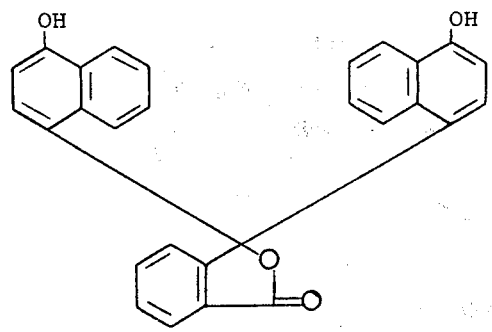
(130) 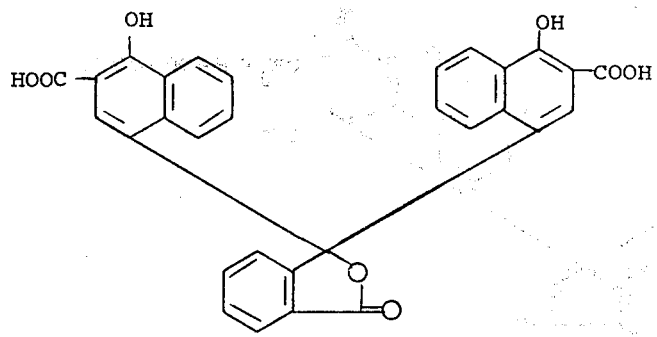
(131) 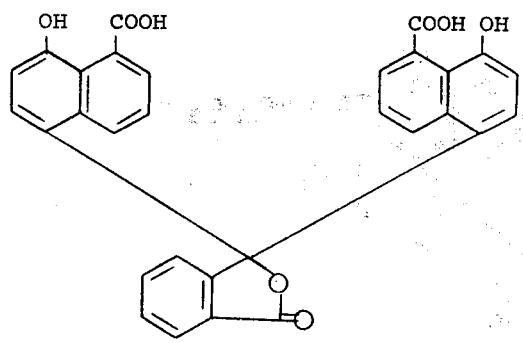
(132) 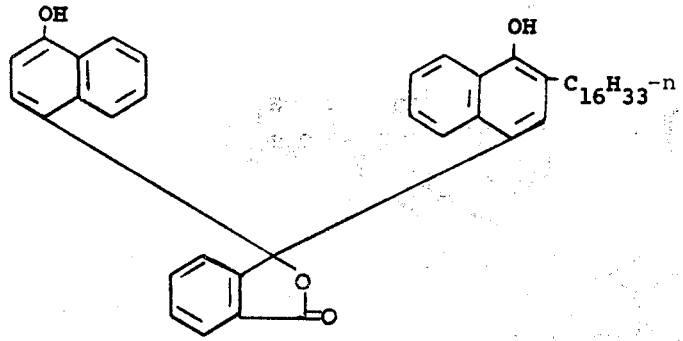
(133) 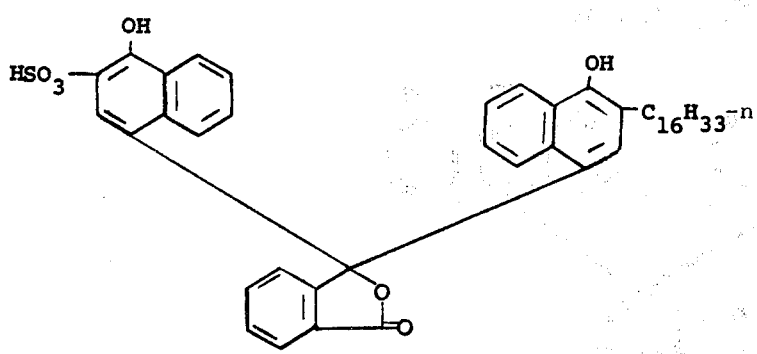

(134) 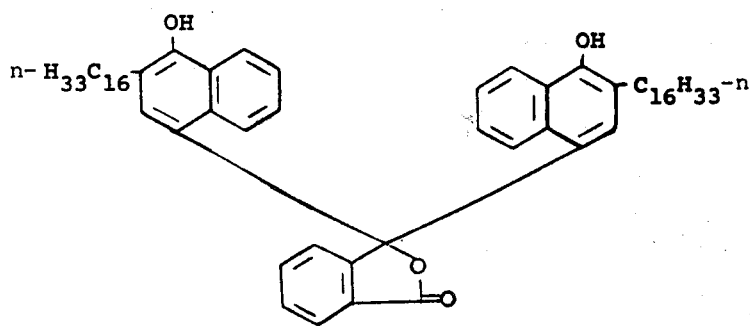
(135) 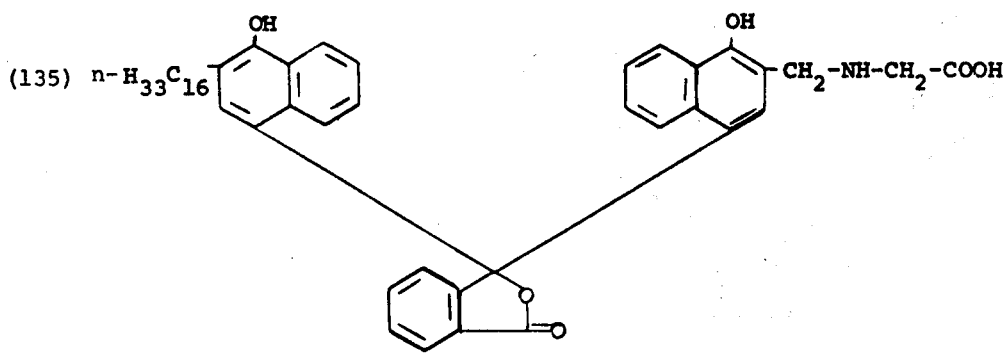
(136) 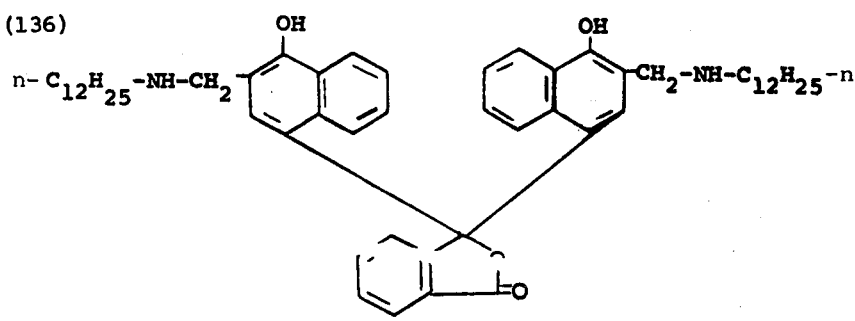
(137) 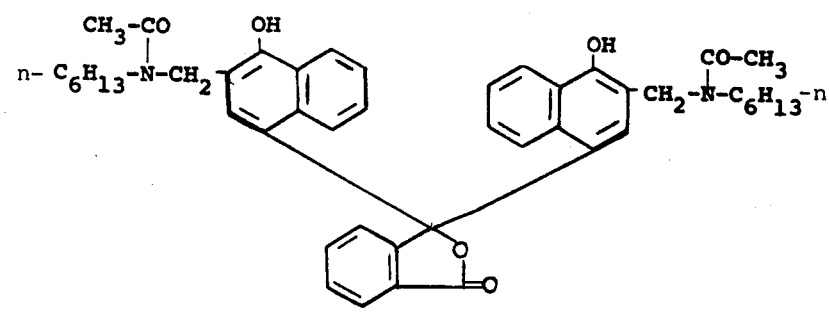
(138) 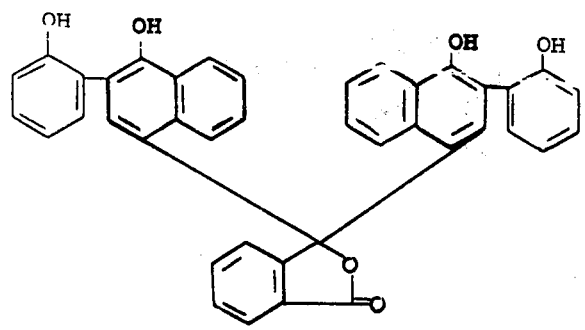

(139)
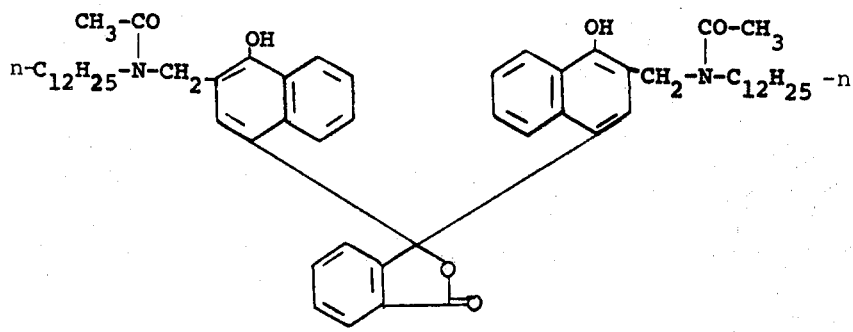
(140)
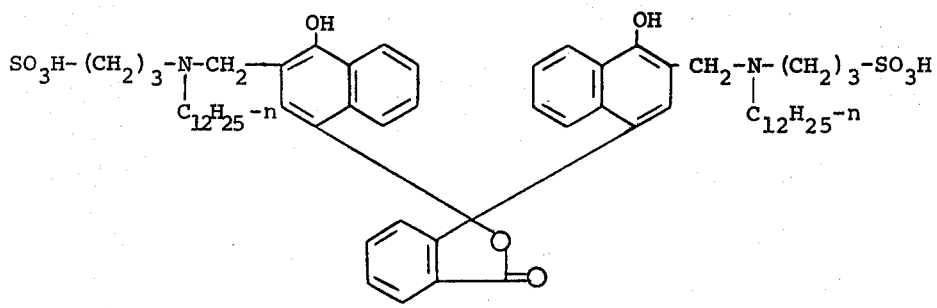
(141)
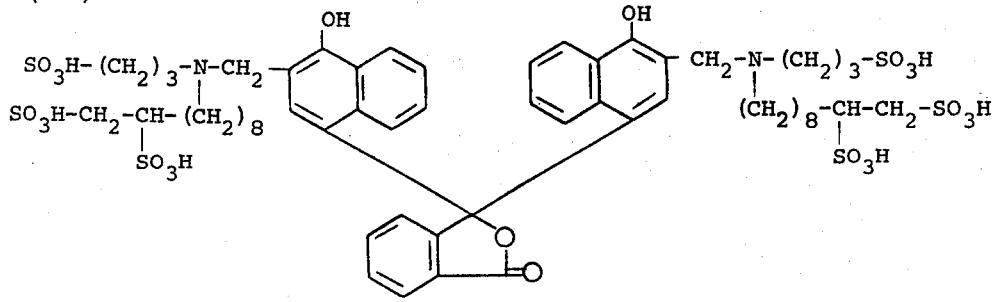
(142)
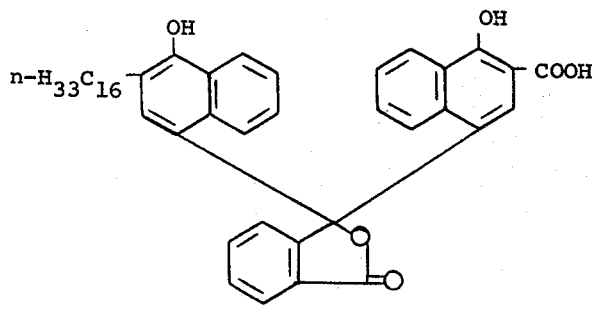
(143)
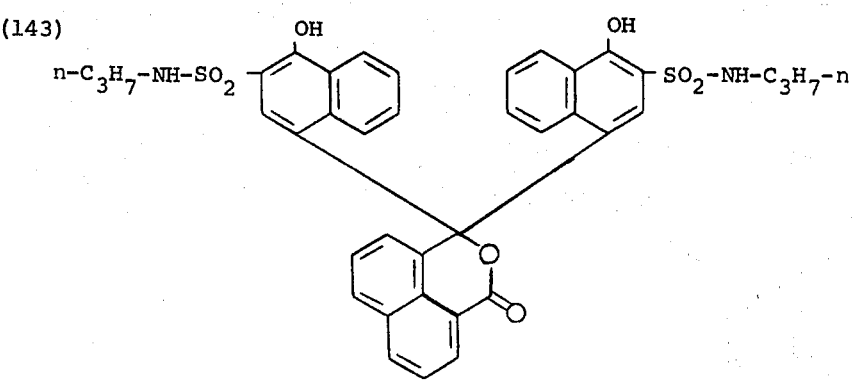

(144) 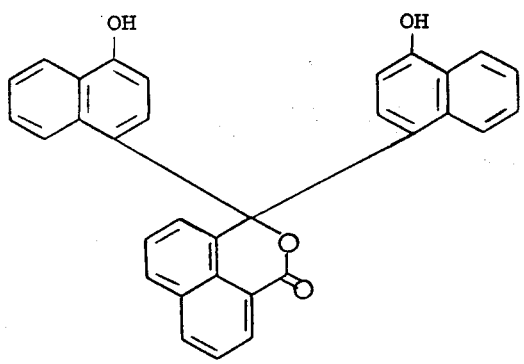
(145) 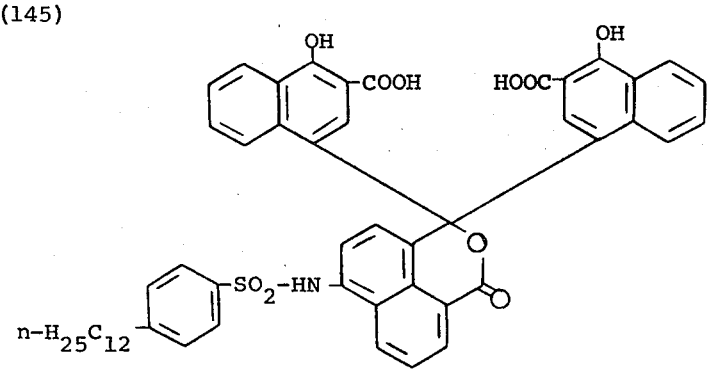
(146) 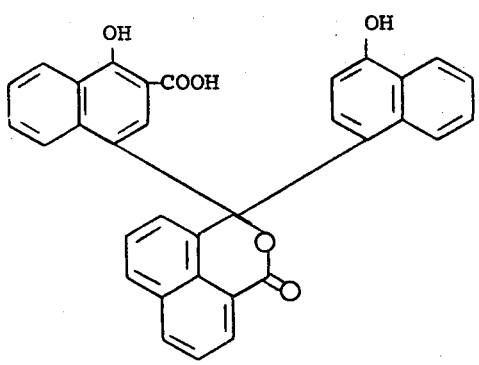
(147) 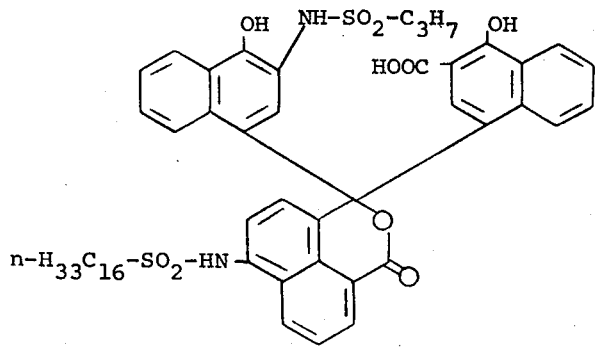
(148) 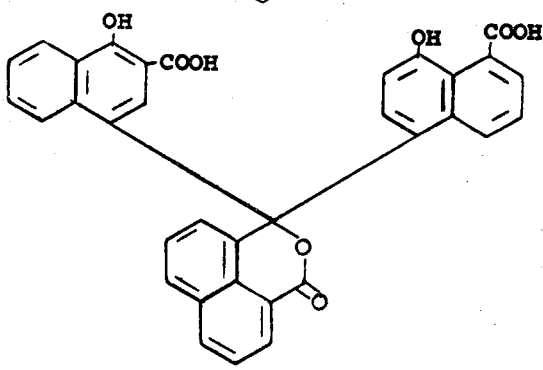

(149) 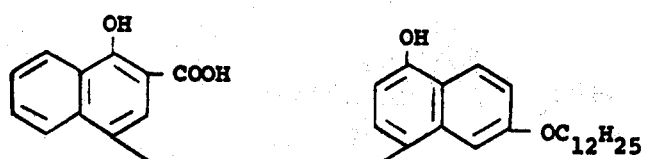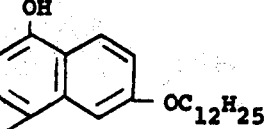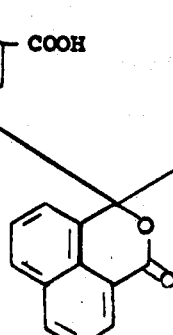
(150) 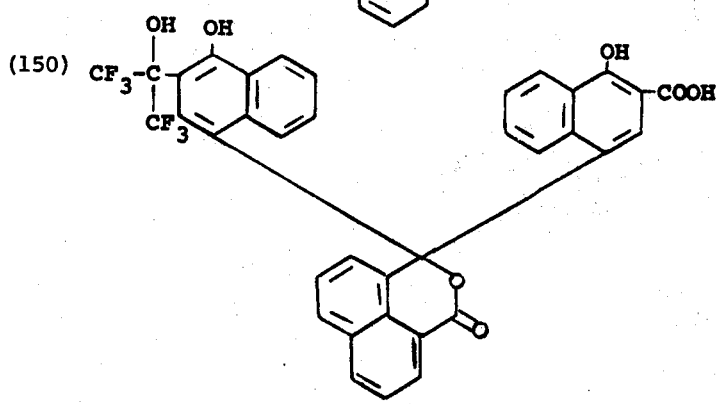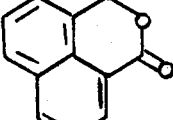
(151) 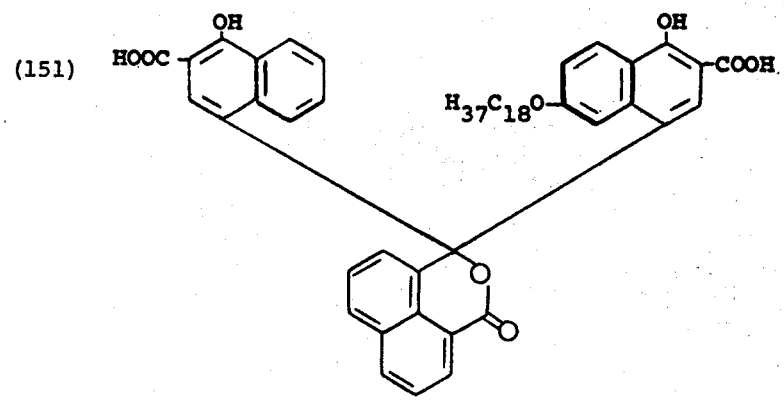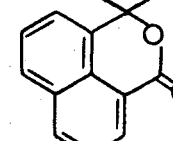
(152) 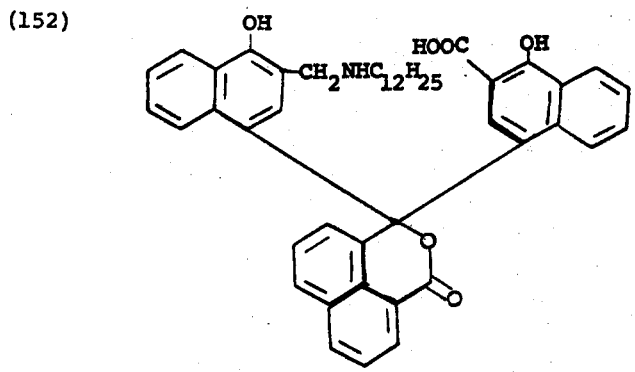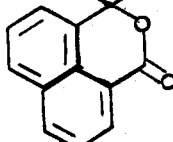
(153) 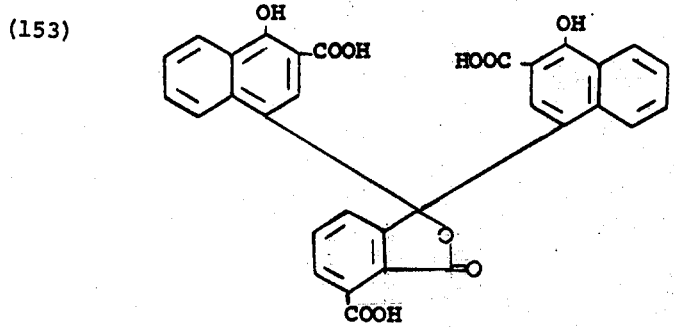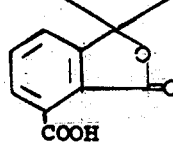

(154)
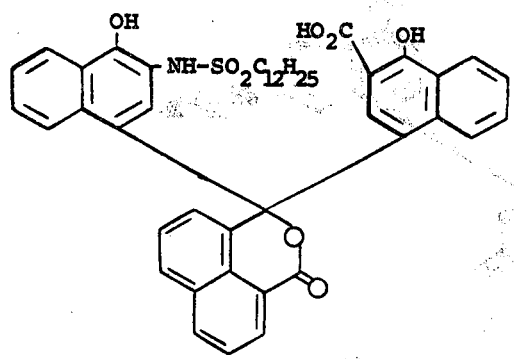
(155)
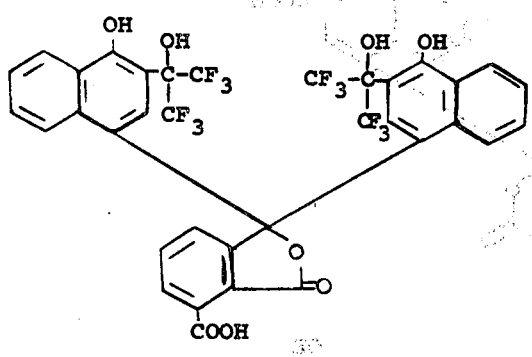
(156)
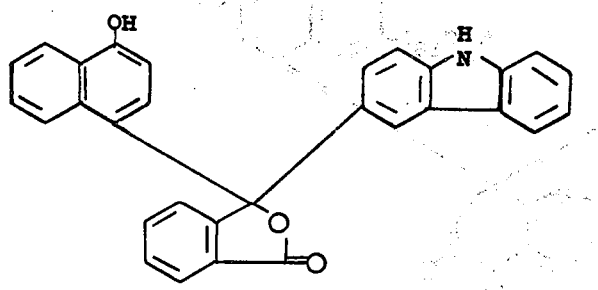
(157)
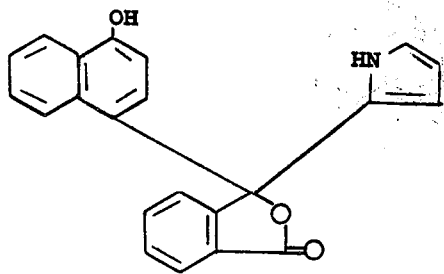
(158)
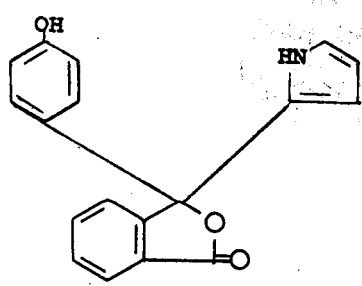

(159) 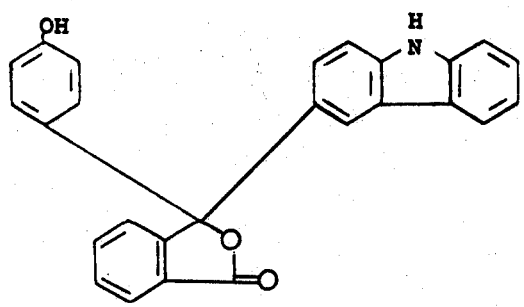
(160) 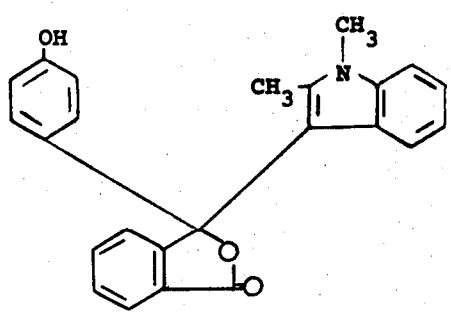
(161) 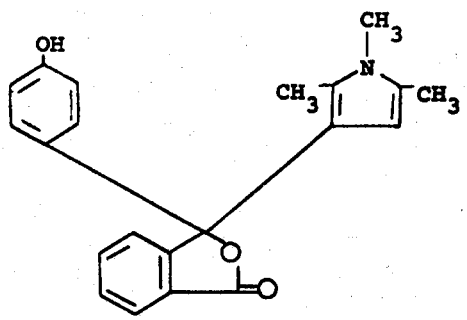
(162) 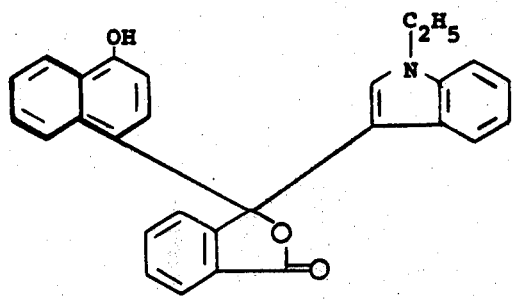
(163) 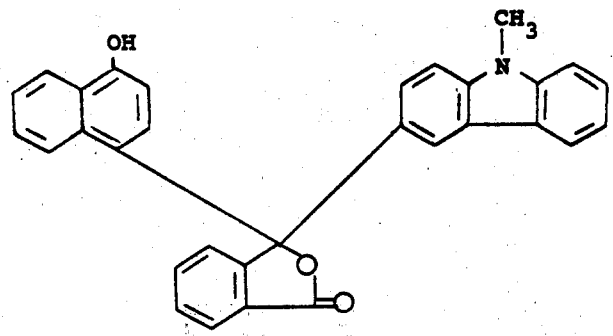

(164)
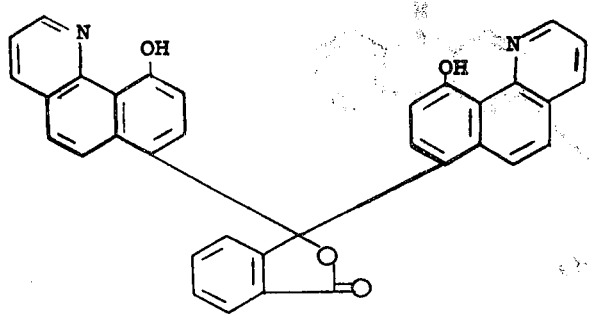
(165)
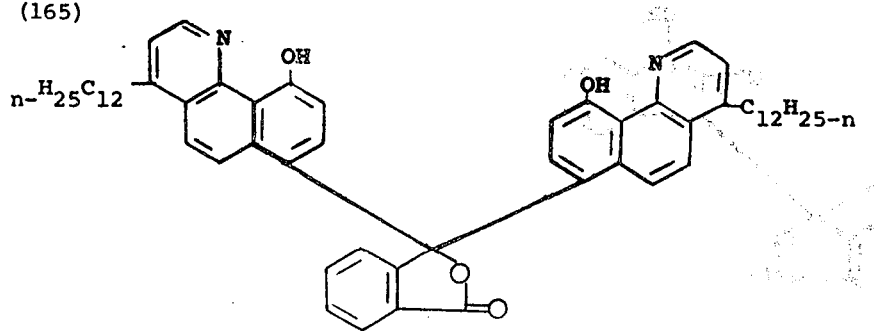
(166)
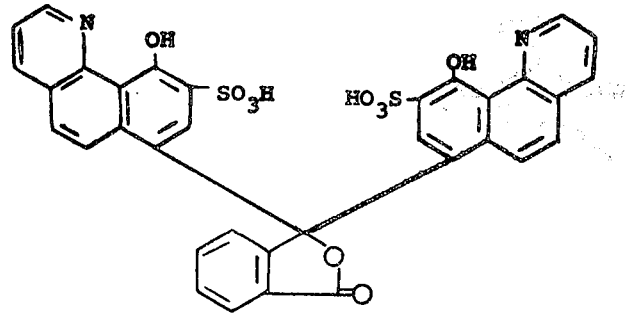
(167)
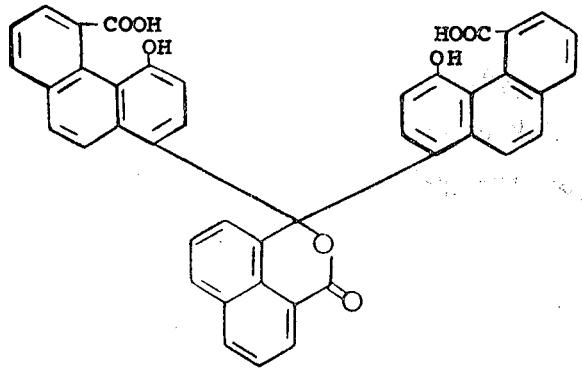
(168)
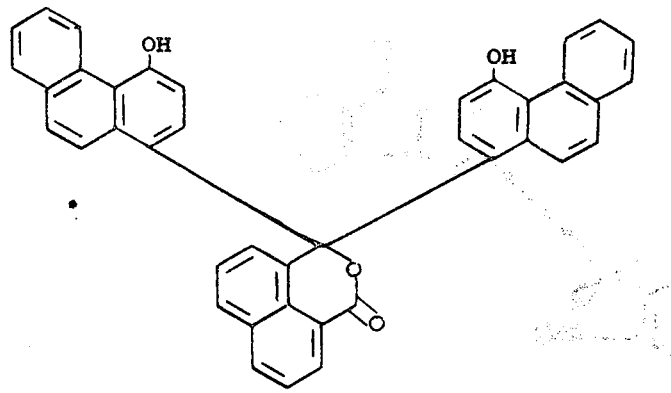

(169) 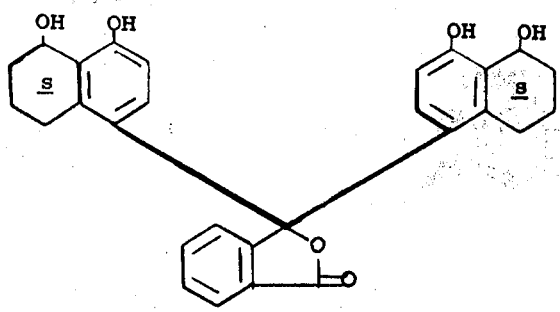
(170) 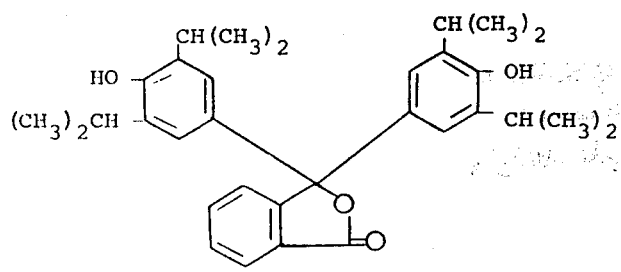
(171) 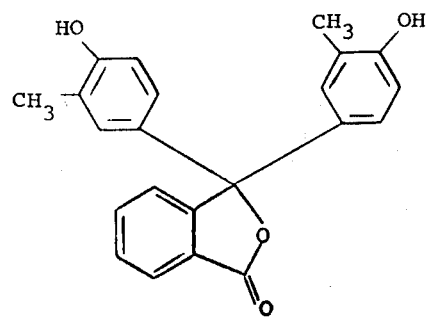
(172) 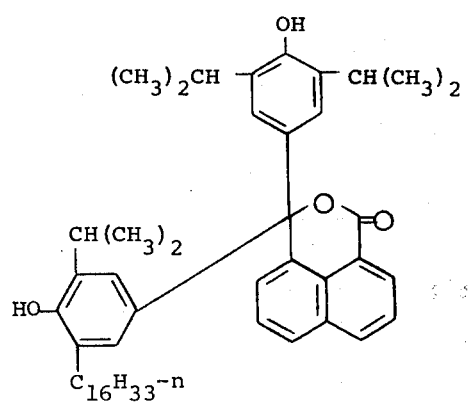
(173) 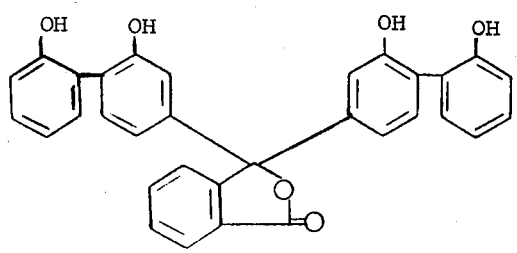

(174) 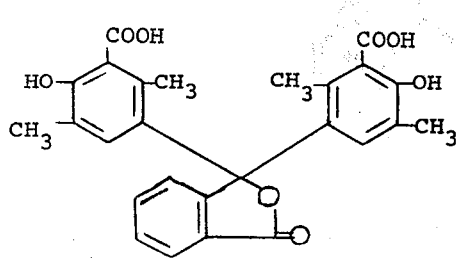
(175) 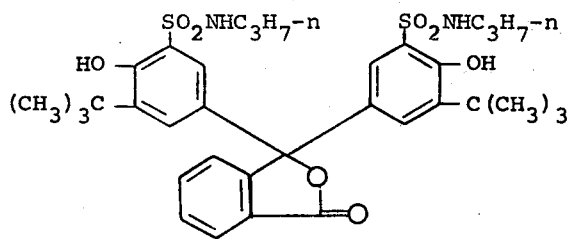
(176) 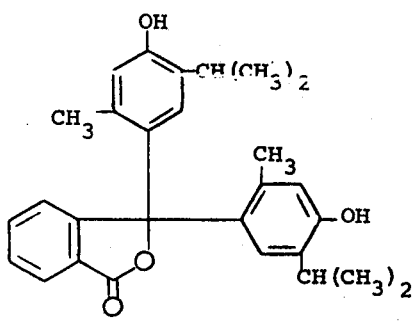
(177) 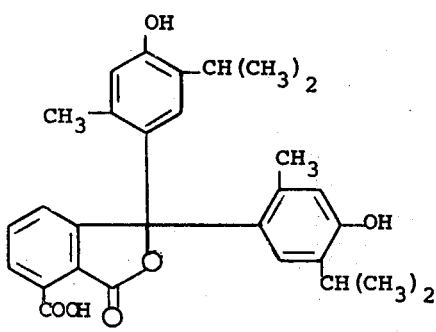
(178) 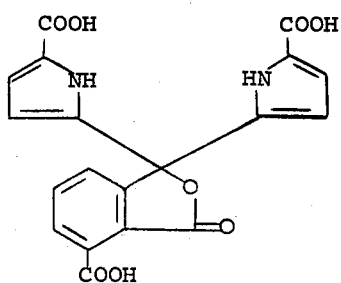

(179) 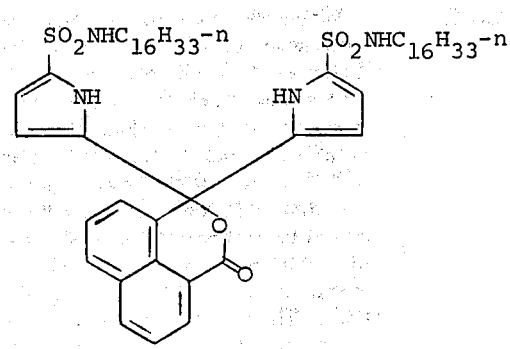

(180) 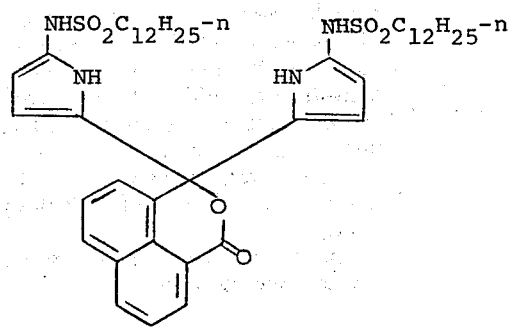

(181) 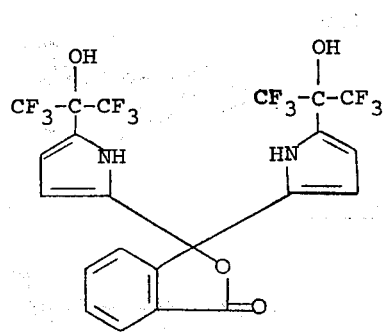

The novel intermediates of the present invention are obtained as the product(s) of step 2 of the present method as shown in the foregoing general reaction scheme and may be represented by the formulae:

(II) 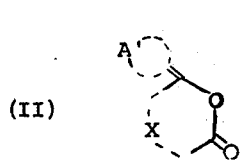 and (III) 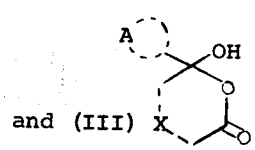

wherein A' is selected from

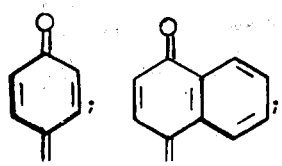

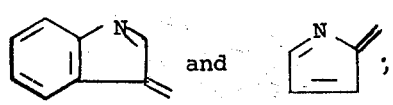

A is selected from

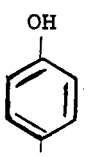 , 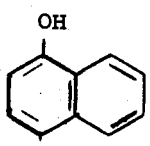 , 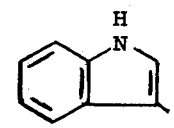

and

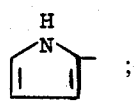 ;

and X represents the atoms necessary to complete a ring-closing moiety selected from phthalide and naphthalide. It will be appreciated that the above intermediates may contain one or more substituents as ultimately desired in the complete dye, such as those enumerated above.

Preferred intermediates are those of formulas (IIa) and (IIIa).

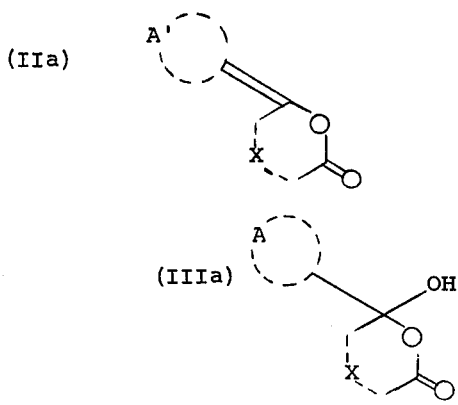

where A' is selected from

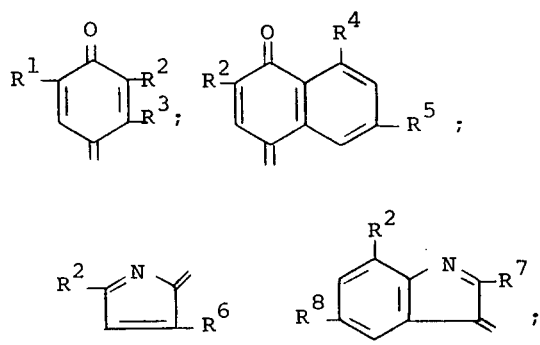

A is selected from

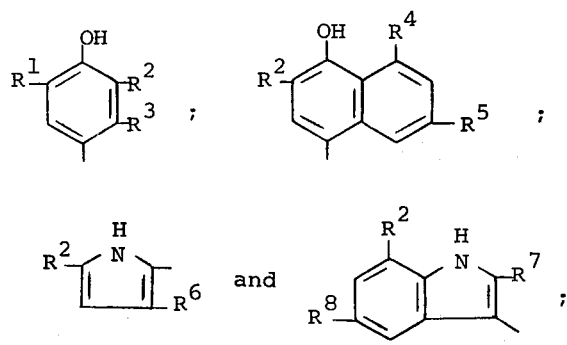

wherein $R^1$, $R^2$, $R^3$, $R^4$, $R^5$, $R^6$, $R^7$ and $R^8$ and X have the same meaning given above. As discussed above, in a particularly preferred embodiment, $R^2$ in the above formulas is a hydrogen-bonding group and $R^3$, $R^5$, $R^6$ and $R^8$ are hydrogen or a group for controlling diffusibility of the dye product, preferably, an alkoxy group containing 1 to 18 carbon atoms. $R^4$ and $R^7$ are hydrogen and $R^1$ is hydrogen, alkoxy or alkyl. In the indole intermediates another particularly preferred embodiment comprises compounds wherein $R^8$ is an electron-withdrawing group, as discussed above, $R^2$ is hydrogen or a hydrogen-bonding group and $R^7$ is hydrogen or $R^2$ is hydrogen and $R^7$ is o-hydroxyphenyl. In these intermediates, the hydroxy and carboxy substituents adjacent the —OH or —NH— may be blocked with alkyl, e.g., having 1 to 6 carbon atoms, such as —COOCH$_3$.

When the oxidation reaction is carried out under anhydrous conditions, the dehydro intermediate of Formula (II) is obtained and may be isolated, if desired, and reacted with the second aromatic compound to form the complete dye. This intermediate may be readily hydrated to yield the intermediate of Formula (III). Mixtures of the two compounds as represented by Formulae (II) and (III) may be obtained when trace amounts of water are present during oxidation or when the compound of Formula (II) is exposed to atomspheric moisture upon standing. The compound of Formula (III) also may be isolated, if desired, before further reaction. Both intermediates react readily with the aromatic compound, and the product of step 2 may be reacted further without isolating the individual compounds even though the product may be a mixture of the dehydro and hydrated intermediates. Preferably, however, the oxidation reaction is conducted under anhydrous conditions to yield the dehydro intermediate. If it is desired to use the hydrated intermediate for further reaction, it is preferred to hydrate the dehydro compound rather than carrying out the oxidation in the presence of water to yield hydrated intermediate directly.

Specific examples of novel intermediates of the present invention include:

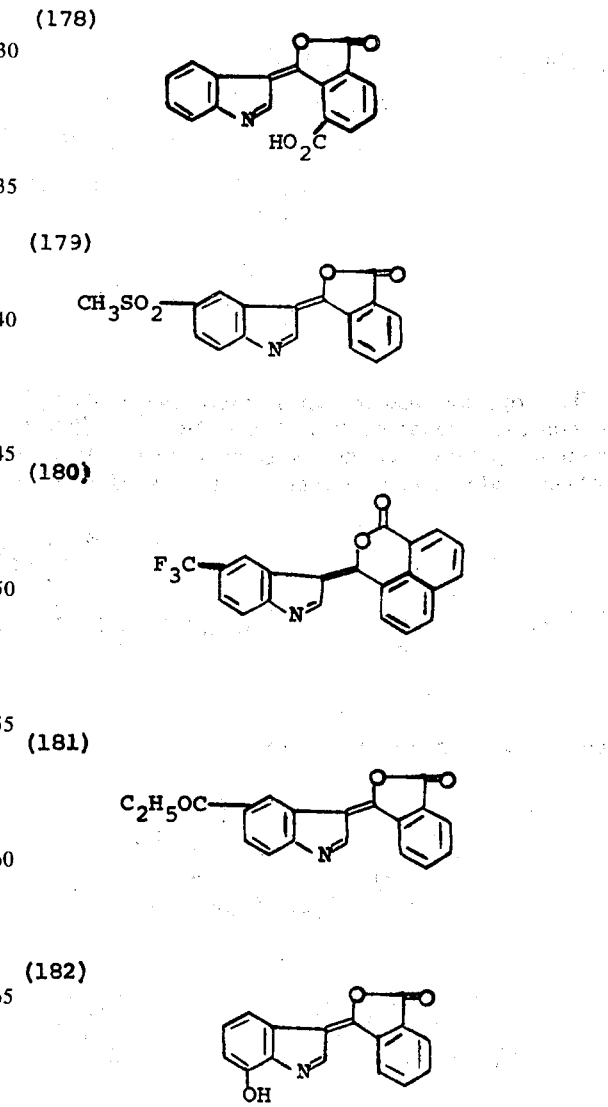

(183)
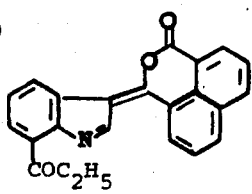
(184)
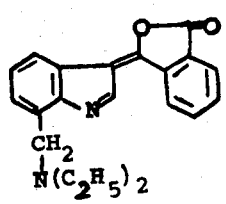
(185)
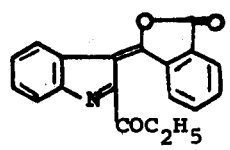
(186)
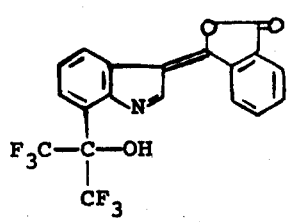
(187)
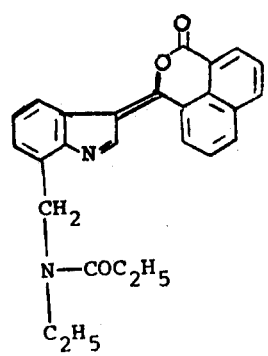
(188)
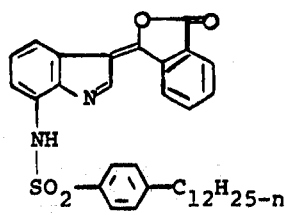
(189)
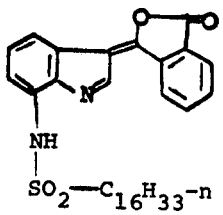
(190)
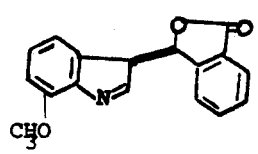
(191)
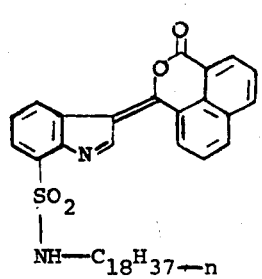
(192)
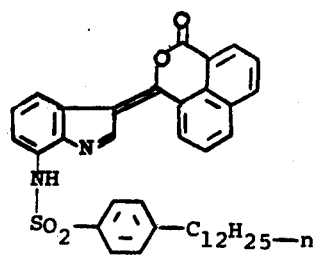
(193)
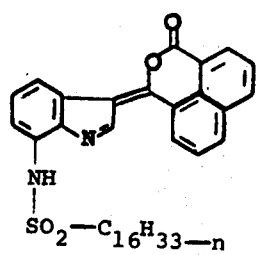
(194)
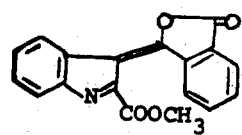

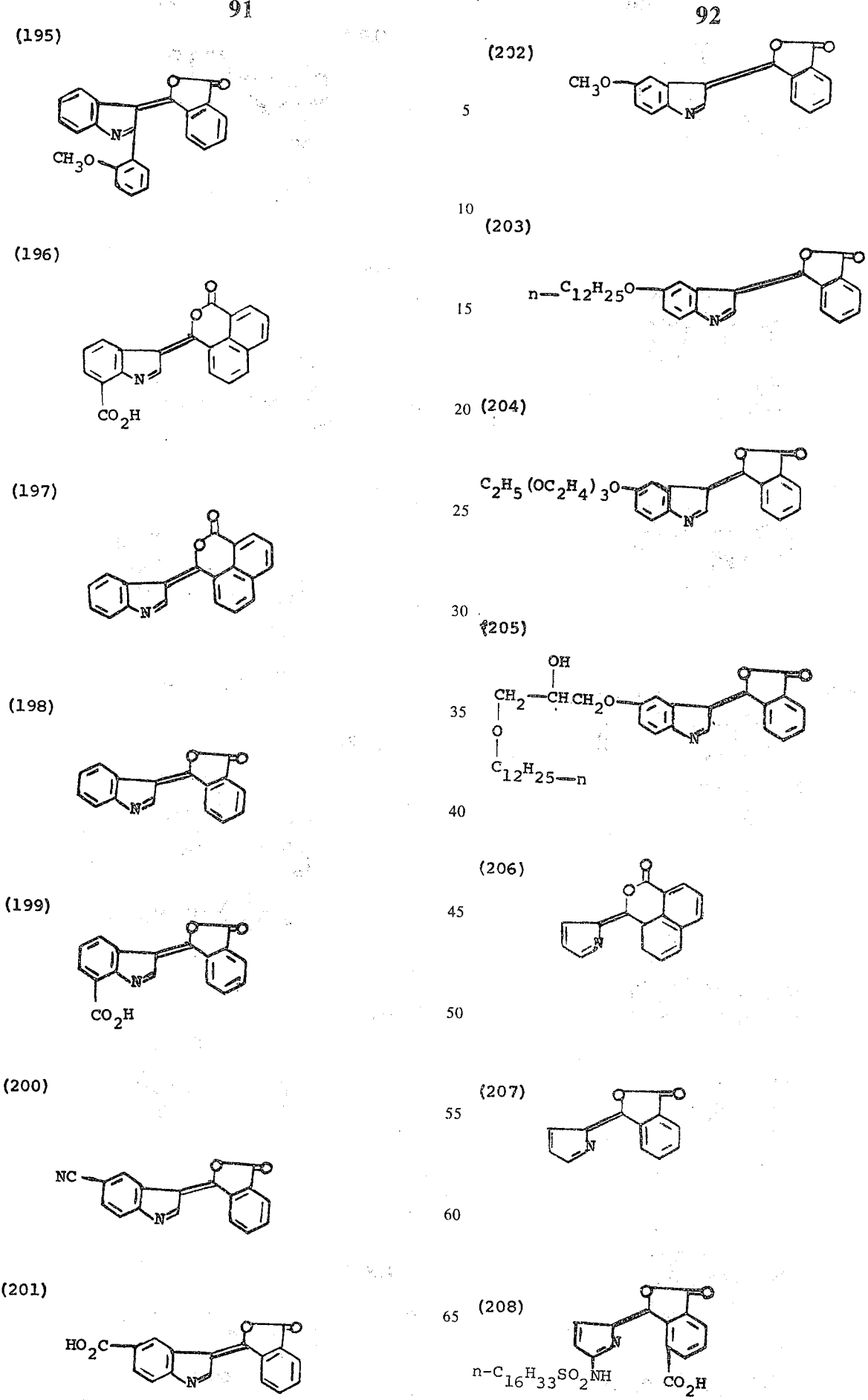

(209) 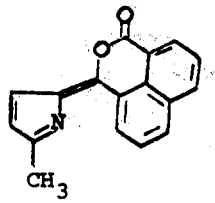
(210) 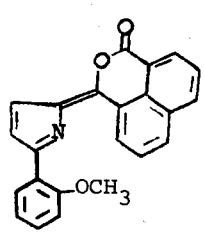
(211) 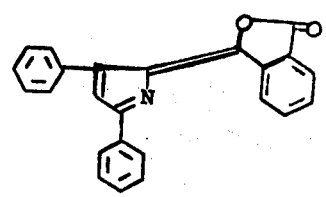
(212) 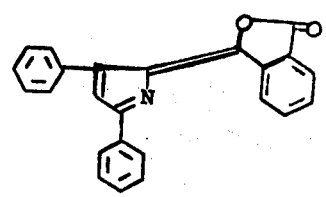
(213) 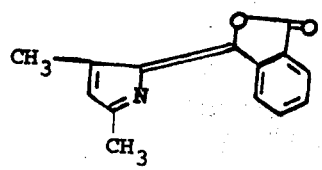
(214) 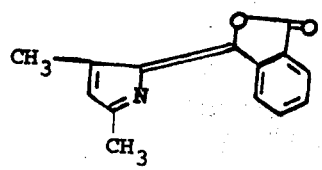
(215) 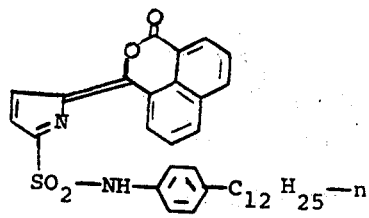
(216) 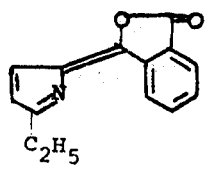
(217) 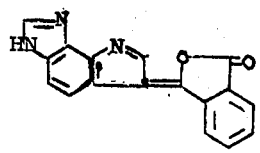
(218) 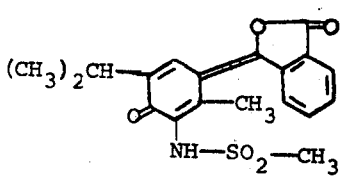
(219) 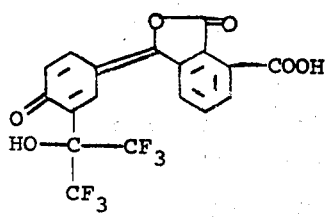
(220) 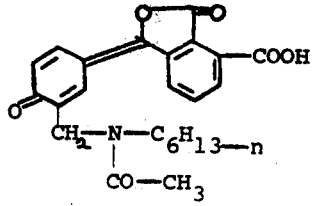
(221) 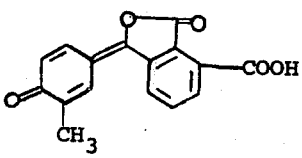
(222) 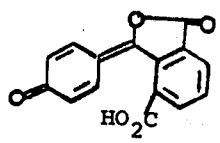

(223)
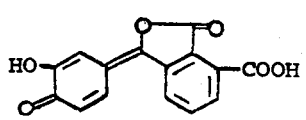
(224)
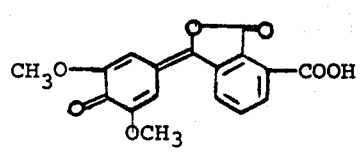
(225)
(226)
(227)
(228)
(229)
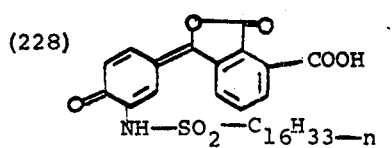
(230)
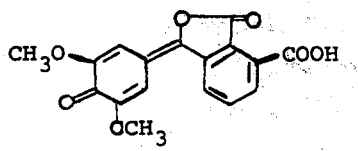
(231)
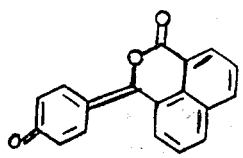
(232)
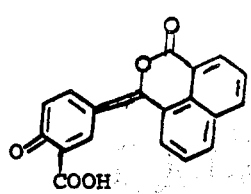
(233)
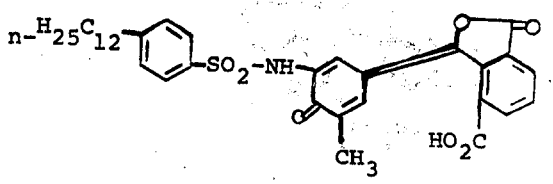
(234)
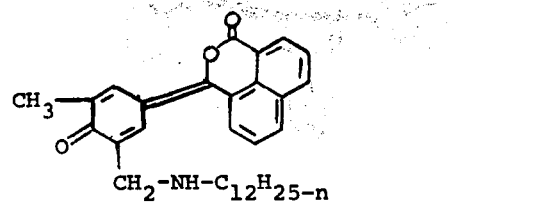
(235)
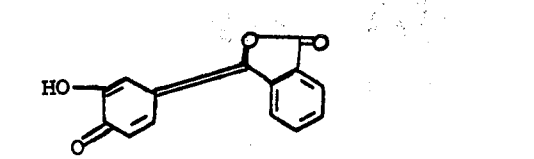
(236)
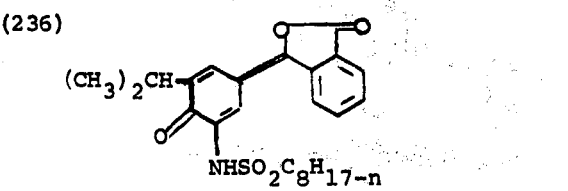

(237) 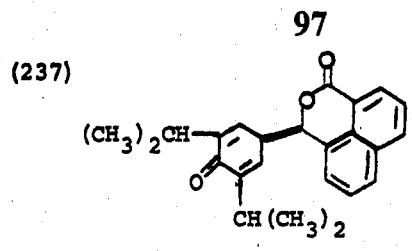
(244) 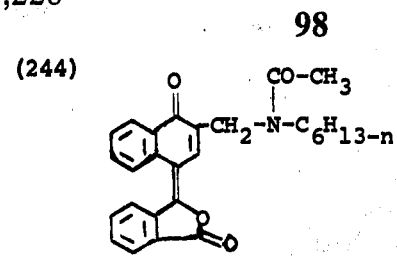
(238) 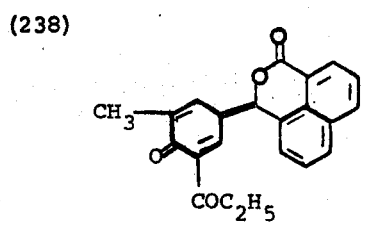
(245) 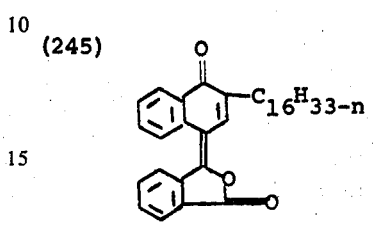
(239) 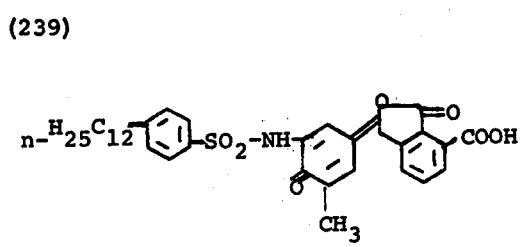
(246) 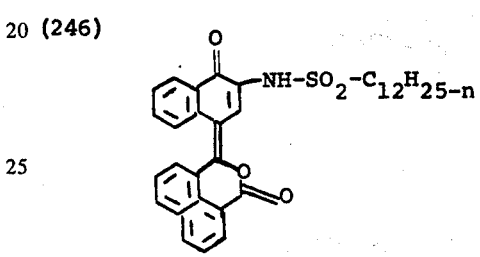
(240) 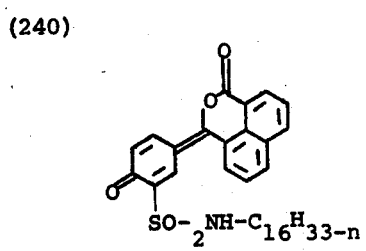
(247) 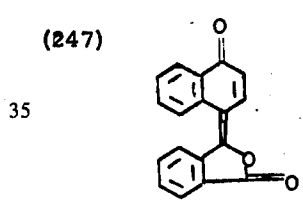
(241) 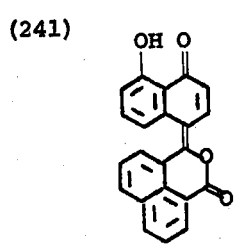
(248) 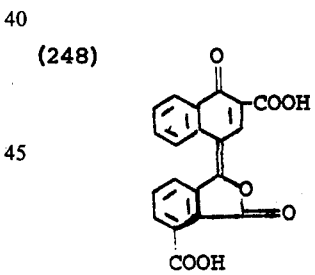
(242) 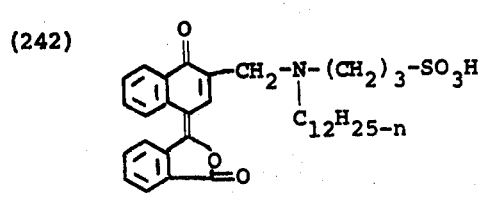
(249) 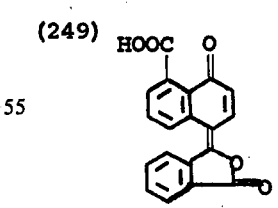
(243) 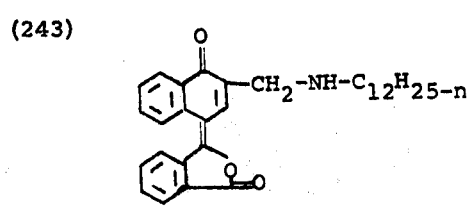
(250) 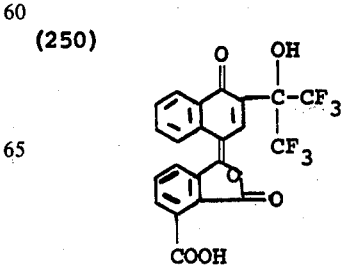

(251) 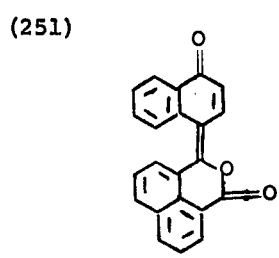
(252) 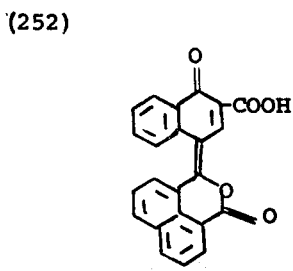
(253) 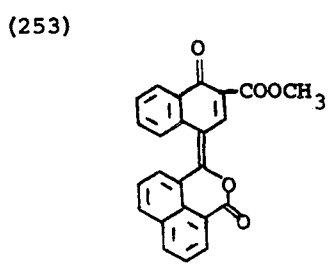
(254) 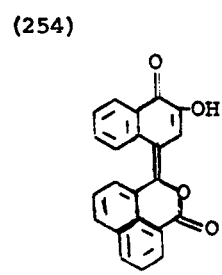
(255) 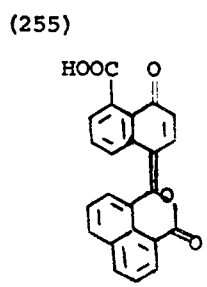
(256) 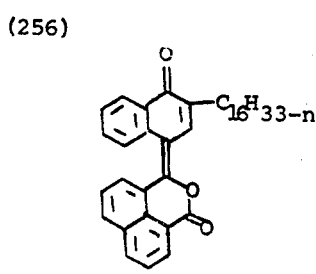
(257) 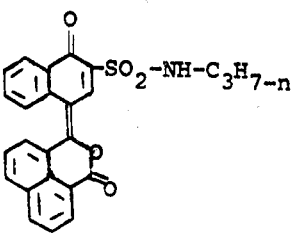
(258) 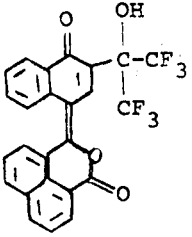
(259) 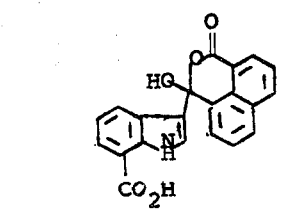
(260) 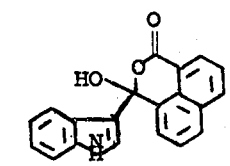
(261) 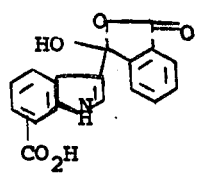
(262) 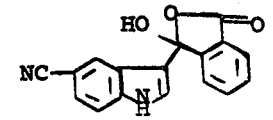
(263) 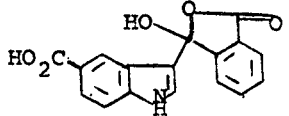

(264) 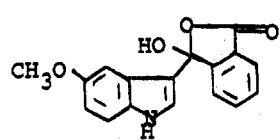
(265) 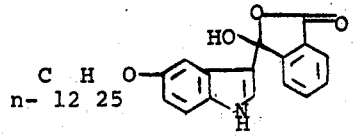
(266) 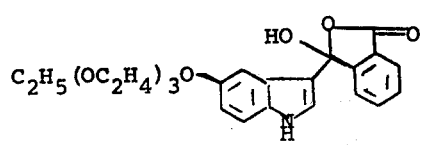
(267) 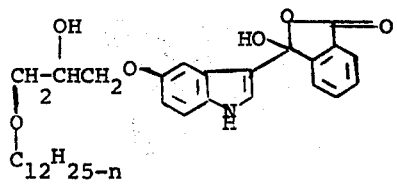
(268) 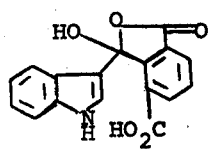
(269) 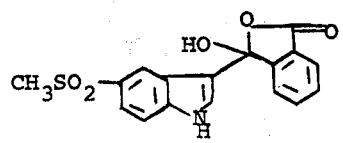
(270) 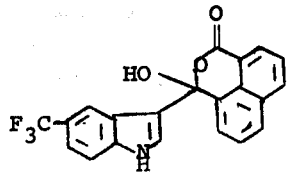
(271) 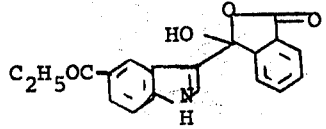
(272) 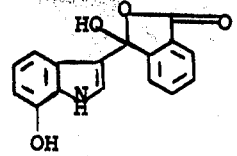
(273) 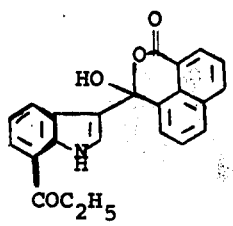
(274) 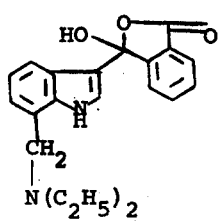
(275) 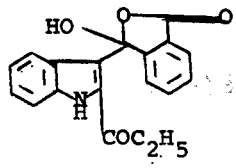
(276) 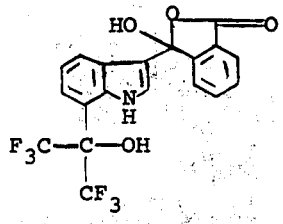
(277) 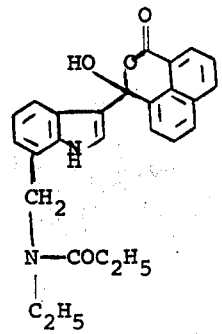
(278) 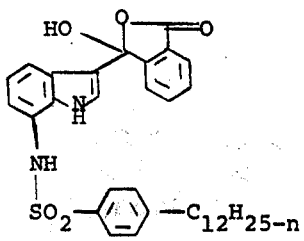

(279) 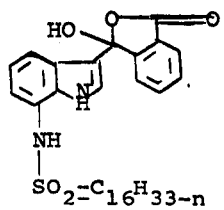
(285) 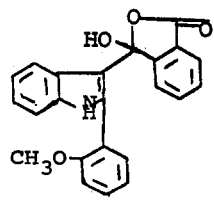
(280) 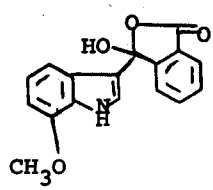
(286) 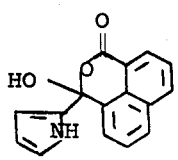
(287) 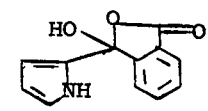
(281) 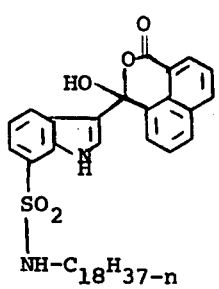
(288) 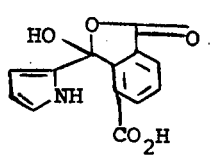
(282) 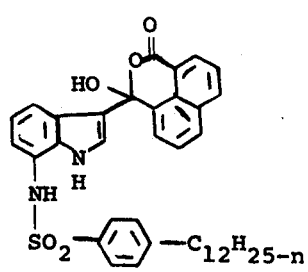
(289) 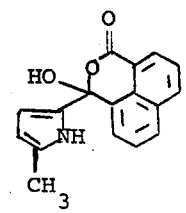
(290) 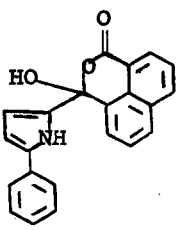
(283) 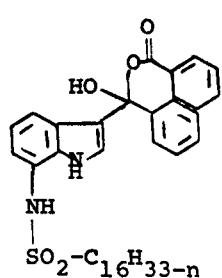
(291) 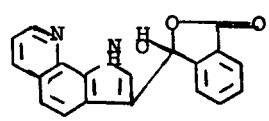
(284) 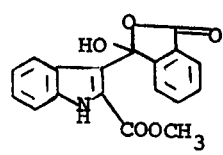
(292) 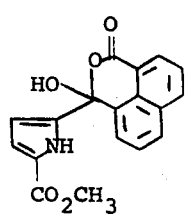

(293) 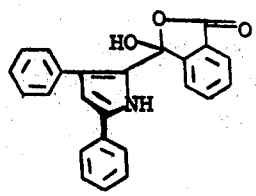
(294) 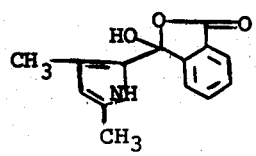
(295) 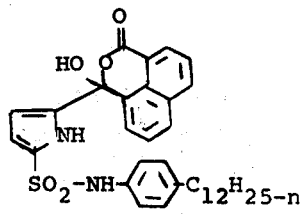
(296) 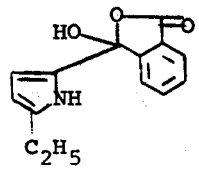
(297) 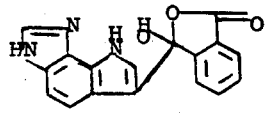
(298) 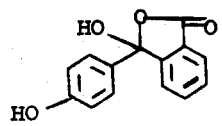
(299) 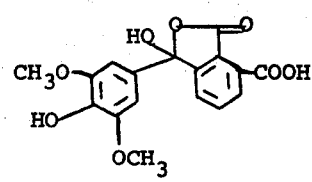
(300) 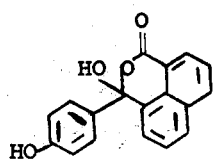
(301) 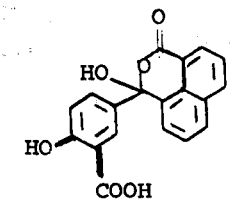
(302) 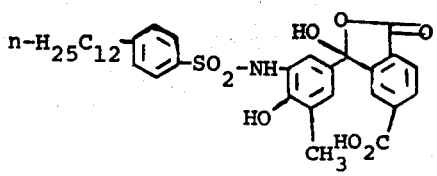
(303) 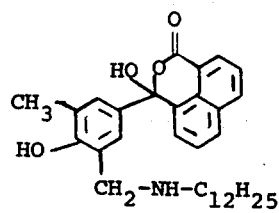
(304) 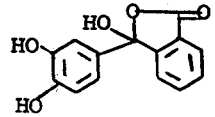
(305) 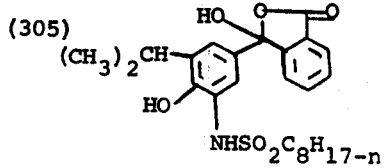
(306) 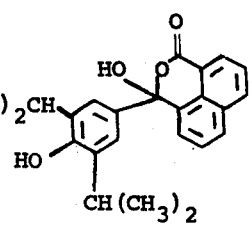
(307) 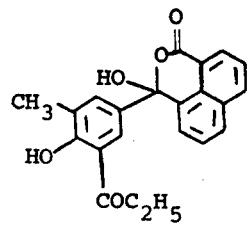

(308) 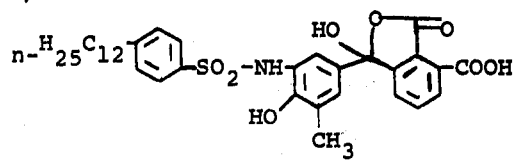
(315) 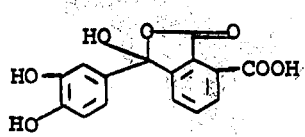
(309) 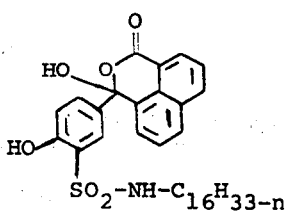
(316) 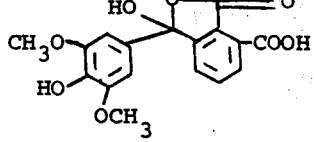
(310) 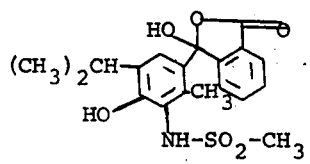
(317) 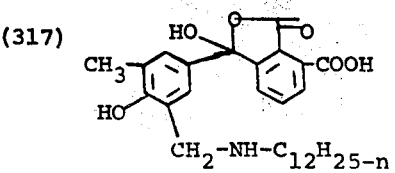
(311) 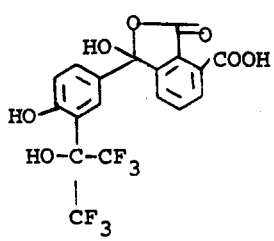
(318) 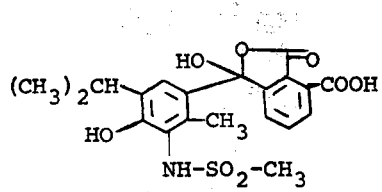
(312) 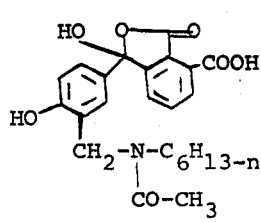
(319) 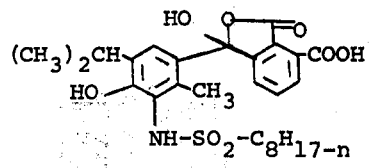
(313) 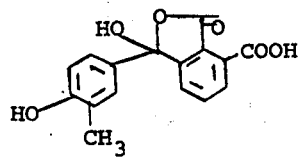
(320) 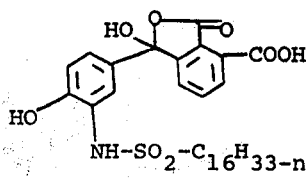
(314) 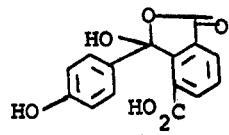
(321) 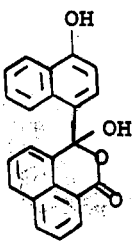

(322) 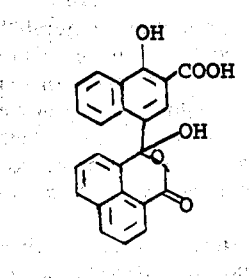
(323) 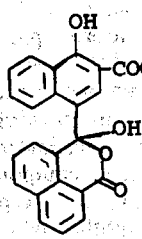
(324) 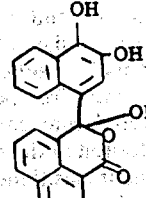
(325) 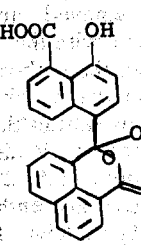
(326) 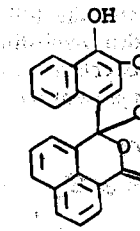
(327) 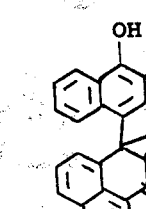
(328) 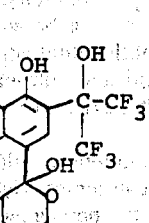
(329) 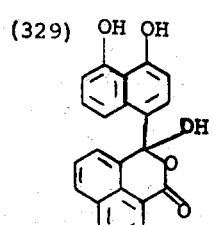
(330) 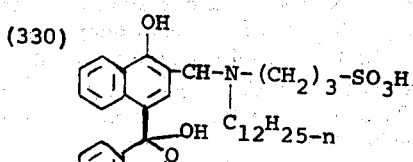
(331) 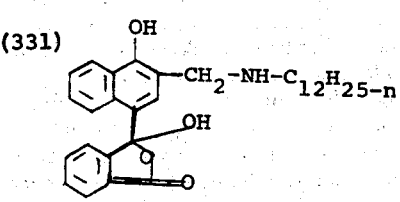
(332) 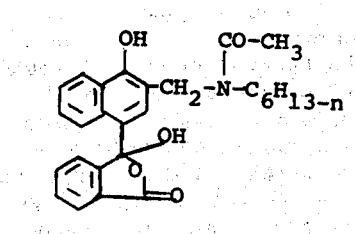
(333) 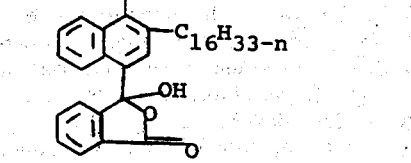
(334) 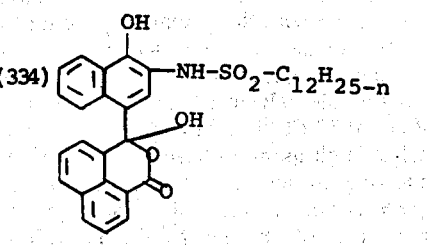
(335) 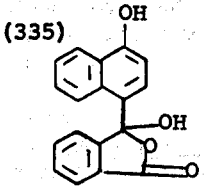

In carrying out the present method, the starting materials, i.e., the hydroxy substituted carbocyclic compound or N-heterocyclic compound and the (na)phthalaldehydic acid may be reacted in a solvent at room temperature or elevated temperature as described in the aforementioned reference of Rees et. al. In the present invention, it is sometimes preferred to react the starting materials in the presence of an external acid catalyst, for example, an organic acid catalyst, such as toluene-p-sulfonic acid, trifluoroacetic acid and trichloroacetic acid. The reaction temperature may vary over a relatively wide range from room temperature, i.e., about 20° C. up to elevated temperatures of about 120°C. which may be readily determined for the particular reactants. To achieve practical reaction rates, it is preferred to conduct the reaction at elevated temperatures but below temperatures where decomposition of starting material and/or side reactions and by-products tend to occur. The solvent used may be any of the inert organic liquids commonly employed for this purpose, such as, glacial acetic acid, ethanol, propanol, petroleum ether, hexane, heptane, cyclohexane, toluene, methylene chloride, and benzene. Ordinarily, a polar solvent is selected when an external acid catalyst is employed and a non-polar solvent when the reaction is conducted in the absence of an external acid catalyst.

The (na)phthalidyl intermediate of the phenol, naphthol, indole or pyrrole thus produced is oxidized by dehydrogenation to selectively remove the hydrogen from the 3-position of the (na)phthalidyl portion and to remove the hydrogen from the hydroxy group of the phenol (or naphthol) or from the 1-position, i.e., N atom of the indole (or pyrrole) thereby converting the single bond connecting the two portions of the molecule to a double bond. Quinones have been found particularly useful for this purpose including, for example, ortho- and para-quinones, such as dicyanodichloroquinone, chloranil, and ortho-chloranil. It has been found that these materials will selectively remove the hydrogens as desired and without oxidizing the compound further. The solvent used in the oxidation step may be any inert organic liquid that does not react with the oxidizing agent, such as dioxane, toluene, benzene, dichloromethane and hexane. The temperature employed may vary widely and generally ranges between about 20°C. and 200°C. As in the initial condensation step, the oxidation step is preferably conducted at elevated temperatures that may be readily selected to achieve a practical reaction rate without by-product formation.

Subsequent to the oxidation step, a second aromatic compound is condensed with the oxidation product to yield the complete indicator dye. The second condensation reaction, like the initial condensation may be carried out in a suitable solvent at room or elevated temperature of 20° to 120°C preferably in the presence of an acid catalyst such as phosphorous oxychloride, boron trifluoride (e.g. in benzene or ether) and other Lewis acids, such as zinc chloride and the catalysts enumerated above, i.e., toluene-p-sulfonic acid, trifluoroacetic acid and trichloroacetic acid. The inert organic solvent used may be any of those commonly employed in condensation reactions such as the particular solvents mentioned above for use in the initial condensation.

The starting materials preferably are used in equimolar quantities and in the oxidation step, the oxidizing agent and (na)phthalidyl intermediate may be used in equimolar quantities but preferably, the oxidizing agent is used in excess to ensure completion of the reaction. A ratio of 1.1 to 1.5 moles of oxidizing agent to 1.0 mole of intermediate has been found satisfactory. In the second or final condensation, the oxidized intermediate and the second aromatic compound selected to form the complete dye preferably are used in equimolar proportions.

As the starting materials, any phenol or 1-naphthol may be employed provided it has a free 4-position, i.e., it is unsubstituted on the carbon atom para to the phenolic hydroxy group, so that the hydrogen will be displaced to yield the corresponding 4-(na)phthalidyl intermediate in the initial condensation with the acid. Likewise, any indole or pyrrole starting material may be employed provided that these compounds have a free 3-position and a free 2-position, respectively, so that the corresponding 3-(na)phthalidylindole and 2-(na)phthalidylpyrrole will be produced in the initial condensation reaction. The indoles and pyrroles each should also have a free 1-position, i.e., the nitrogen atoms of these compounds should be substituted with hydrogen. Other than the necessary free positions discussed above, the starting materials may contain one or more substituents as may be desired in the final indicator dye provided any substituent positioned adjacent the condensation site and tending to bond internally with the dehydro intermediate is protected with a blocking group that may be removed subsequent to condensation of the intermediate with the second aromatic compound. For example, the carboxy group of 2-carboxyindole may be protected as an alkyl ester and the alkyl blocking portion removed after the complete dye is formed by alkaline hydrolysis. Similarly, a hydroxysubstituted aryl or alkyl group in the 2-position of an indole may be protected as an alkyl ether and the alkyl blocking portion removed by catalytic hydrogenation.

For purposes of nomenclature, the following illustrates the numbering of the hydroxy-substituted carbocyclic compounds and N-heterocyclic compounds used as the starting materials in the present method.

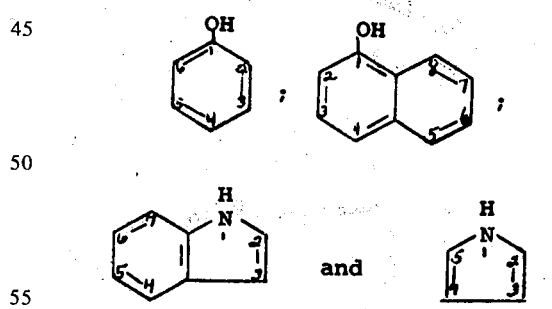

Likewise, the aldehydic acid reacted with the hydroxy-substutited carbocyclic or N-heterocyclic compound may be a substituted phthalaldehydic acid or naphthaldehydic acid, such as, carboxy-substituted compounds, e.g., 4-carboxy-phthalaldehydic acid and 7-carboxy-phthalaldehydic acid and sulfonamido-substituted compounds, e.g., 6-hexadecylsulfonamido-naphthalaldehydic acid.

The aromatic compound condensed with the oxidized intermediate to form the complete dye may be a carbocyclic aryl compound of the benzene or naphthalene series, or it may be a heterocyclic aryl compound containing O, N, S, or P or combinations thereof. The heterocyclic compound is preferably N-heterocyclic derived from, e.g., indole, pyrrole or carbazole, though it may be derived from, e.g., N-benzylindoline. In a preferred embodiment, the starting materials employed in the synthesis of the oxidized intermediates of the present invention and the aromatic compound condensed with the intermediate are the phenols, 1-naphthols, pyrroles and indoles designated above as i, ii, iii and iv, respectively.

The following Examples are given to further illustrate the present invention and are not intended to limit the scope thereof.

EXAMPLE 1

Preparation of the compound of formula (21)

A mixture of 6.0 g. (0.0372 mole) of 7-carboxyindole and 7.5 g. (0.0372 mole) of naphthaldehydic acid in 38 ml. of glacial acetic acid was heated to reflux and stirred mechanically. To the solution was added dropwise, 38 ml. of 12% toluene-p-sulfonic acid-acetic acid. An immediate precipitation of product began and the mixture was refluxed for five minutes. The mixture was cooled to room temperature, filtered, and the 3-naphthalidylindole intermediate washed with 50 ml. of acetic acid. The solid was then stirred in 100 ml. of acetone, filtered and dried to give 12.8 g. (86% by weight yield) of a white crystalline solid, 239°–240° C. melting range.

A mixture of 11.0 g. (0.028 mole) of the intermediate prepared above and 140 ml. of dioxane was refluxed with stirring under nitrogen. To the solution was added 7.3 g. (0.032 mole) of 2,3-dichloro-5,6-dicyano-1,4-benzoquinone and the refluxing continued for 3.5 hours. The mixture was cooled to room temperature and the pink solid comprising oxidized intermediate was collected by suction filtration. The solid was extracted twice by boiling in 125 ml. of acetone for 5 to 10 minutes. The solid was then heated in 125 ml. of ethanol and the white solid collected. Weight 7.2 g. (78% by weight yield).

A mixture of 0.40 g. (1.2 m mole) of oxidized intermediate and 0.51 g. (1.2 m mole) of 7-hexadecylsulfonamidoindole in 5 ml. of glacial acetic acid was heated to 65° C. with stirring. To the mixture was added 5 ml. of 12% toluene-p-sulfonic acid-acetic acid over a five-minute period. The solution turned an intense purple color. The heating was continued for 15 minutes at 65° C. and cooled to room temperature. The solution was poured into 20 ml. of water containing 3 ml. of concentrated $NH_4OH$. The precipitate was collected and dried. Recrystallization of 0.8 g. of this material from methanol-water gave 0.66 g. (77% by weight yield) of title compound, melting range 216°–217° C.

Steps 1 and 2 of the foregoing procedure were repeated using 2-carboxy-benzaldehyde (o-formylbenzoic acid), the open-ring form of phthalaldehydic acid.

8.05 g. (0.05 mole) of 7-carboxyindole and 7.5 g. (0.05 mole) of 2-carboxybenzaldehyde were heated under reflux in 90 ml. of xylene in a 500 ml. roundbottom flask with stirring for 8 hours. The mixture was cooled to room temperature and allowed to stand overnight. The product was collected by suction filtration, washed with benzene and dried in vacuo at 60° C. Wgt. = 13.0 g. The product was recrystallized from ethanol (~300 ml.). After refrigeration, the product was collected by suction filtration. Wgt. = 8.2 g., melting range 250°–2°C. The ethanol was evaporated to ~50 ml. and a second crop of material collected. Wgt. = 2.0 g., melting range 248°–50°C. Overall yield 10.2 g., (67% by weight yield). The materials was thoroughly dried in vacuo (60° C.).

3.2 g. (0.011 mole) of the product obtained above and 2.7 g. (0.012 mole) of 2,3-dichloro-5,6-dicyano-1,4-benzoquinone were heated in 60 ml. of freshly opened analytical grade dioxane at 60° C. for 24 hours under nitrogen with stirring. The mixture was cooled to room temperature and the hydroquinone (2.05 g.) removed by filtration. The filtrate was concentrated to a volume of 10 ml. in vacuo and an additional 0.4 g. of hydroquinone collected. The product was precipitated by the addition of benzene (60 ml.) to the filtrate. Wgt. = 1.9 g. Concentration of the filtrate to a volume of 20 ml. followed by the addition of 50 ml. of benzene furnished an additional 1.0 g. of product.

The hydroquinone collected was compared to and found to be identical with a standard sample of 2,3-dichloro-5,6-dicyano-1,4-hydroquinone substantiating the removal of the two hydrogens from the phthalidyl-substituted carboxyindole to yield a dehydro product under anhydrous conditions. The dehydro product upon initial precipitation was yellow and was observed to become substantially colorless upon standing in the presence of atmospheric moisture. The colorless product formed upon standing on the basis of molecular weight determination was found to correspond to the hydrated form of the dehydro product as evidenced by a difference of 18 in molecular weight. Further studies revealed that a mixture of dehydro and hydrated products can be obtained in the oxidation step when moisture is present, for example, when trace amounts of water is present in the dioxane solvent. Upon further reaction with orthohydroxyphenylindole, the dehydro and hydrated intermediates showed substantially equivalent reactivity in the formation of the complete dye.

EXAMPLE 2

The product of Example 1 was prepared in the same manner described above except that o-chloranil (0.029 mole) was substituted for dichlorodicyanoquinone as the oxidizing agent.

EXAMPLE 3

Preparation of the compound of formula (97)

A solution of 10.0 g. (0.05 mole) of naphthaldehydic acid and 8.9 g. (0.05 mole) of 2,6-diisopropylphenol in 80 ml. of 12% p-toluene sulfonic acid in acetic acid was refluxed for 8 hours. The solution was cooled and the product began to precipitate out. The mixture was poured onto 200 g. of ice and stirred. The white solid was filtered and dissolved in 200 ml. of hot ethanol. Water was added slowly until the solution was turbid and cooled and the solid collected by filtration and dried to give 15.0 g. (83.5% by weight yield) of solid, melting range 185°–187° C. (decomposition).

5.0 g. (0.0139 mole) of the intermediate prepared above was dissolved in 100 ml. of methylene chloride. To this solution was added 3.4 g. (10% excess) of 2,3-dichloro-5,6-dicyano-1,4-benzoquinone. The reaction mixture was refluxed under a nitrogen atmosphere for 4 hours. The mixture was cooled and the 2,3-dichloro-5,6-dicyano-1,4-hydroquinone filtered off. The methylene chloride was evaporated under vacuum and the oil dissolved in ethanol with heating. The ethanol was evaporated under vacuum and the solid collected as an orange powder 4.5 g. (90% by weight yield), melting range 38°–30°C.

3.2 g. (0.0092 mole) of the oxidized intermediate prepared above was dissolved in 25 ml. of phosphorous oxychloride together with 2.0 g. of 2-isopropyl phenol. The resulting mixture was stirred for 6 hours at room temperature and then was added to a mixture of 100 g. of ice, 100 ml. of water and 2 ml. of conc. hydrochloric acid. The product was extracted with 200 ml. of ether, dried over anhydrous calcium chloride, and the ether evaporated. The resulting red oil was placed in hexane and a pink solid formed with recrystallization from 100 ml. of ethanol and 20 ml. of water to yield 3.1 g. (70% by weight yield) of the title compound, melting range, 225° – 227° C.

EXAMPLE 4

Preparation of the compound of formula (124)

Example 3 was repeated except that 2-hexadecyl-1-naphthol was reacted with the oxidized naphthalidyl-substituted 2,6-diisopropyl phenol intermediate by adding 15 ml. of phosphorous oxychloride to 0.5 g. (0.0014 mole) of oxidized intermediate and 0.51 g. (0.0014 mole) of 2-hexadecyl-1-naphthol. The resulting mixture was stirred at room temperature for 6 hours and then poured onto a mixture of 25 g. of ice, 25 ml. of water with stirring. The product was extracted with ether and dried over anhydrous calcium chloride. The ether was evaporated and hexane added to the residue. Upon refluxing a solution was obtained which upon cooling gave a precipitate, 0.5 g. (49% by weight yield) of the title compound.

EXAMPLE 5

Preparation of the compound of formula (98)

Example 3 was repeated except that 1.0 g. (0.0028 mole) of the oxidized naphthalidyl-2,6-diisopropyl phenol intermediate was reacted with 0.495 g. (0.0028 mole) of 2,6-diisopropyl phenol at room temperature for 6 hours in the presence of 15 ml. of phosphorous oxychloride. The resulting solution was added slowly to a mixture of 100 g. of ice, 50 ml. of water and 2 ml. of concentrated hydrochloric acid. The oily product was extracted with ether, dried over anhydrous caclium chloride and the ether evaporated. The oil was placed in 50 ml. of hexane and refluxed for 1 hour. The solution was filtered and the filtrate cooled. The precipitate formed upon cooling was collected by filtration and dried to give 0.6 g. (40% by weight yield of title compound, melting range 83° – 85° C.

EXAMPLE 6

Preparation of the compound of formula (171)

a. 7-carboxyphthalaldehydic acid (5.0 gms., 0.0258 mole) was added under nitrogen to 25 ml. of 85% sulfuric acid in a 100 ml. round bottom flask equipped with a stirring bar. Crystalline o-cresol (2.81 gms., 0.0260 mole) was added to the flask with stirring. The resulting orange-pink solution was stirred at room temperature for 6 hours. The solution was then poured onto ice (about 50 gms.) with stirring to give a greyish pink mass which was filtered and dried in a vacuum oven at 50°C. The dried solid was recrystallized from methanol with "Norit" to yield colorless needles (4.40 gms., melting point 146°C.).

b. The product of step a above (0.546 gm., 0.001 mole) was added under nitrogen to a solution of 2,3-dichloro-5,6-dicyano-1,4-benzoquinone (0.454 gms., 0.001 mole) in 10 ml. of dichloromethane contained in a 25 ml. round bottom flask. The resulting brownish orange solution was stirred for 4 hours at room temperature. The dichlorodicyanohydroquinone precipitate was removed from the solution by filtration, and the dichloromethane was evaporated from the filtrate to give a tan solid. The solid was recrystallized from dichloromethane and hexane and purified by column chromatography. Elution with dichloromethane and hexane removed a few impurities. Further elution yielded the dehydro intermediate which was recovered as a pink solid (0.440 mg., melting point 220° C. dec.).

c. The dehydro intermediate of step b (0.270 gm., 0.001 mole) was dissolved into 10 ml. of ethyl ether in a three neck flask with stirring under nitrogen. To this solution was added crystalline o-cresol (0.108 gm., 0.001 mole) and then 1 ml. of boron trifluoride etherate by dropper. The resulting dark magenta solution was allowed to stand 16 hours at room temperature. The ethyl ether was evaporated by a flow of nitrogen leaving a magenta gum. 10 ml. of ice water was added to the gum. A pink precipitate formed which was removed by filtration and dried. The precipitate was dissolved into 25 ml. of 5% aqueous sodium hydroxide, and after filtration of the solution, was reprecipitated by the addition of 5% hydrochloric acid. The off-white precipitate was filtered and dried and recrystallized from ethanol containing "Norit" to give the title compound as a white solid (0.220 gm., melting range 295° – 297° C.).

EXAMPLE 7

Preparation of the compound of formula (151)

Following the first two steps of Example 2, 2-carboxy-1-naphthol (1-hydroxy-2-naphthoic acid) was reacted with naphthaldehydic acid to yield the corresponding p-naphthalidylnaphthol adduct which then was oxidized to the dehydro intermediate using o-chloranil. The dehydro intermediate, 3-(3'-carboxy-4'-oxo-1'-naphthylidene)naphthalide, was converted to its hydrated form with water. The hydrated intermediate, 3-hydroxy-3-(3'-carboxy-4'-hydroxy-1'-naphthyl)naphthalide (about 528 mgs.), 1-hydroxy-6-octadecyloxy-2-naphthoic acid (about 480 mgs.) and boron-trifluoride etherate (about 185 mgs.) in glacial acetic acid (12 cc.) was refluxed 3 hours. The solution was cooled and evaporated to half-volume. On standing a solid formed which was filtered, dried and recrystalized to give the title compound in about 5% by weight yield.

The last step of Example 7 was repeated using 3-hydroxy-3-(3'-carbomethoxy-4'-hydroxy-1'-naththyl)naphthalide-1,8 as the hydrated intermediate. The solid formed in the concentrated reaction solution upon standing was recrystallized from ethanol, and then hydrolyzed with hot ethanolic sodium hydroxide solution. After cooling to room temperature, the basic solution was acidified with 20% hydrochloric acid. The gum that formed was scratched and triturated with water until solidification was complete. The solid was air dired and dissolved in boiling cyclohexane. A white solid precipitated from the hot solution almost immediately which was collected and dried to give the compound of formula 151 in a yield of about 30% by weight.

In addition to the above compounds, the specific indicator dyes of formulae (1) to (19) and (48) above also were prepared in accordance with the procedure of Example 1. The dye of formula (1) was prepared by reacting indole with the acid, oxidizing the intermediate thus formed and then reacting the oxidized intermediate with ortho-hydroxyphenyl indole. In preparing the dyes of formulae (2) to (9), the respective 5-substituted indoles were initially reacted with the acid and in preparing the dyes of formulae (16) to (19), the respective 7-substituted indoles were initially reacted with the acid. The dyes of formulae (10) to (15) and (48) were prepared by reacting 7-carboxyindole with the acid and subsequently reacting the intermediate after oxidation with the compound selected for the second aromatic nucleus.

It will be appreciated that other phenols, 1-naphthols, indoles and pyrroles substituted in the manner discussed above, for example, with hydrogen-bonding and electron-withdrawing groups and groups useful in controlling the mobility of the dye product in aqueous solution may be substituted for the starting materials used in the procedure set out in the foregoing examples to give the corresponding adduct with naphthaldehydic, phthaldehydic and carboxyphthaldehydic acid. Following the above procedures, the adduct thus obtained may be converted to the corresponding oxidation product comprising, for example, the compounds of formulas IIa and IIIa by reacting with a quinone, such as, the o-chloranil or dichlorodicyanobenzoquinone employed above. Also following the foregoing procedures, the oxidation product may be condensed with the selected aromatic compound, particularly a phenol, 1-naphthol, pyrrole or indole substituted as described in the preferred embodiment to yield the indicator dye, either a "mixed" dye or a symmetrical or unsymmetrical indicator.

As noted previously, solvents other than those specified may be used in the oxidation and the initial and final condensation steps and other acid condensation catalysts may be employed. Though it is not essential, any one or all of the steps of the process may be carried out in an inert atmosphere, for example, under nitrogen, and final indicator dyes may be purified by recrystallization from any appropriate solvent or in any other suitable and convenient manner.

Indicator dyes comprising phthaleins containing an indole radical and a second radical derived from a different N-heterocyclic aryl compound and phthaleins containing an indole radical and a second radical derived from a hydroxy-substituted carbocyclic aryl compound form the subject matter of copending U.S. patent applications Ser. No. 202,555 and Ser. No. 202,558, respectively, now U.S. Pat. Nos. 3,816,120 and 3,816,124, respectively. Indicator dyes containing a naphthalide ring-closing moiety substituted in the 6-position with certain groups, such as sulfonamido, form the subject matter of copending U.S. patent Application Ser. No. 193,746, now U.S. Pat. No. 3,811,881. Phthaleins derived from azaphenanthrol form the subject matter of copending U.S. patent application Ser. No. 177,513, now U.S. Pat. No. 3,779,754. Phthaleins containing one phenol radical and a second carbocyclic aryl radical, which is different, e.g., a phenyl radical with a different p-substituent form the subject matter of copending U.S. patent application Ser. No. 203,544, now U.S. Pat. No. 3,782,937.

The indicator dyes produced in accordance with the present invention may be employed in conventional analytical procedures where phthalein indicator dyes, such as, phenol phthalide and phenol naphthalide are commonly used, for example, to measure changes in pH value. The dyes produced according to the present invention also find other uses.

As discussed in copending U.S. patent applications, Ser. No. 108,260 and Ser. No. 103,392, now U.S. Pat. Nos. 3,702,244 and 3,702,245, respectively, it has been found that a selectively exposed photosensitive material having a latent image therein may be processed in the presence of extraneous incident radiation actinic thereto by reason of the protection afforded by suitably positioning with respect to the exposure surface of the photosensitive layer an effective concentration of a selected dye or dyes as optical filter agents. The use of certain indole dyes including indole phthalides and naphthalides as optical filter agents for protecting photosensitive materials from radiation in the shorter wavelength region of the visible spectrum forms the subject matter of aforementioned U.S. patent application Ser. No. 108,260. The use of certain dyes derived from phenols and naphthols including phenol and naphthol phthalides and naphthalides as optical filter agents for protecting photosensitive materials from radiation in the longer wavelength region of the visible spectrum forms the subject matter of aforementioned U.S. patent application Ser. No. 103,392.

Indicator dyes found particularly useful as optical filter agents prepared according to the preferred embodiment of the present invention are phthaleins derived from certain hydroxy-substituted carbocyclic and N-heterocyclic compounds which contain a hydrogen-bonding group, i.e., a substituent capable of forming a hydrogen-bonded ring with the respective phenolic —OH and —NH— portions of these compounds. Certain indole and phenolic phthaleins of this type form the subject matter of U.S. patent application Ser. No. 204,350, now U.S. Pat. No. 3,862,128. Other phthaleins of this type derived from phenols and 1-naphthols form the subject matter of copending U.S. patent applications Ser. Nos. 103,864 and 103,865, respectively, now U.S. Pat. Nos. 3,833,615 and 3,833,614, respectively. Still other phthaleins of this type derived from indoles form the subject matter of copending U.S. patent application Ser. No. 108,277, now abandoned. Indoles substituted with selected hydrogen-bonding groups useful in the synthesis of such indole phthalides and naphthalides form the subject matter of copending U.S. patent application Ser. No. 108,663, now U.S. Pat. No. 3,772,329.

Since certain changes may be made in the above processes and products without departing from the scope of the invention herein involved, it is intended that all matter contained in the above description shall be interpreted as illustrative and not in a limiting sense.

What is claimed is:
1. A process which comprises the steps of:
 1. reacting in substantially equimolar proportions in an inert organic liquid solvent at a temperature between about 20°C. and 120°C. in the presence of an acid catalyst selected from toluene-p-sulfonic acid, sulfuric acid, trifluoroacetic acid and trichloroacetic acid, (a) a compound selected from

(i) 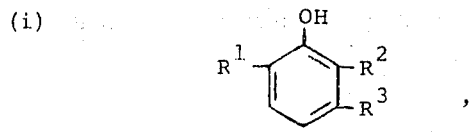

(ii) 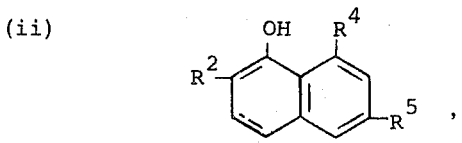

(iii) 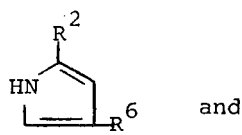  and (iv) 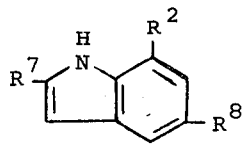

wherein R¹ is selected from hydrogen, alkoxy containing 1 to 3 carbon atoms and alkyl containing 1 to 3 carbon atoms; R² is selected from hydrogen, hydroxy, carboxy, sulfonamido, sulfamoyl, o-hydroxyphenyl, bis-trifluoromethylcarbinol, methoxy, alkyl containing 1 to 16 carbon atoms; R³ is selected from hydrogen, alkoxy containing 1 to 18 carbon atoms and alkyl containing 1 to 3 carbon atoms; R⁴ is selected from hydrogen, hydroxy and carboxy; R⁵ is selected from hydrogen and alkoxy containing 1 to 18 carbon atoms; R⁶ is selected from hydrogen, phenyl, alkyl containing 1 to 3 carbon atoms, and alkoxy containing 1 to 18 carbon atoms; R⁷ is selected from hydrogen, phenyl, o-hydroxyphenyl and alkyl containing 1 to 3 carbon atoms and R⁸ is selected from hydrogen, cyano, carboxy, halo, trifluoromethyl, sulfonyl and alkoxy containing 1 to 18 carbon atoms with (b) an aldehydic acid selected from phthalaldehydic acid, unsubstituted or substituted in one of the 4- or 7-positions with carboxy and naphthalaldehydic acid, unsubstituted, to form the corresponding adduct having the formula:

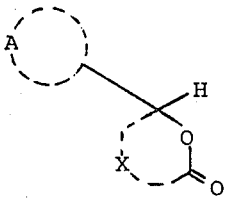

wherein A is a radical selected from p-hydroxyphenyl, p-hydroxynaphthyl, pyrr-2-yl and indol-3-yl corresponding to said (i), (ii) and (iii) and (iv), respectively, and X represents the carbon atoms necessary to complete a ring-closing moiety selected from phthalide, unsubstituted or substituted in the 4- or 7-position with carboxy, and naphthalide, unsubstituted; and 2. reacting said adduct with a quinone selected from chloranil, o-chloranil and 2,3-dichloro-5,6-dicyano-1,4-benzoquinone in a molar ratio of about 1.1 to 1.5 moles of quinone per 1.0 mole of adduct in an inert organic liquid solvent at a temperature between about 20°C. and 200°C. to form the corresponding oxidation product selected from (I) 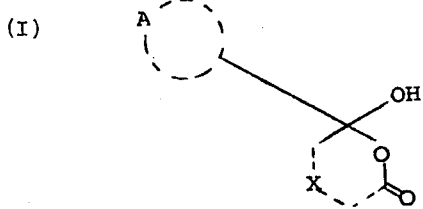

wherein A and X have the same meaning given above, and (II) 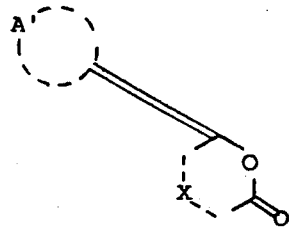

wherein A' is selected from

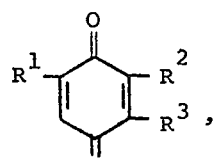 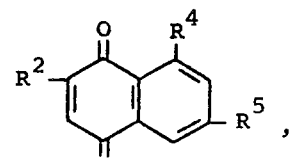

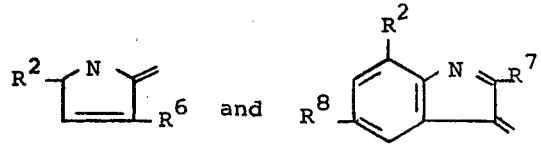

wherein R¹, R², R³, R⁴, R⁵, R⁶, R⁷ and R⁸ and X have the same meaning given above and mixtures of (I) and (II), said (I) being produced under anhydrous conditions and said (II) and said mixtures of (i) and (II) being produced in the presence of moisture.

2. A process as defined in claim 1 which includes the additional step of:

3. reacting said oxidation product with a compound (c) selected from (i), (ii), (iii) and (iv) as defined in (a) above in substantially equimolar proportions in an inert organic liquid solvent at a temperature between about 20°C. and 120°C. in the presence of an acid catalyst selected from toluene-p-sulfonic acid, sulfuric acid, trifluoroacetic acid, trichloroacetic acid and a Lewis acid to form the corresponding 3,3-disubstituted phthalide or naphthalide,

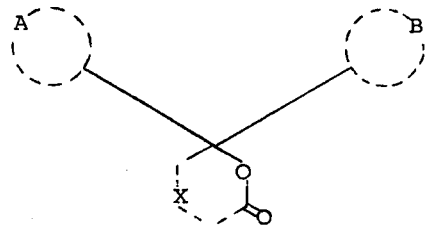

wherein A and B each is a radical selected from p-hydroxyphenyl, p-hydroxynaphthyl, pyrr-2-yl, and indol-3-yl corresponding to said (i), (ii), (iii) and (iv), respectively, and X represents the carbon atoms necessary to complete a ring-closing moiety selected from phthalide, unsubstituted or substituted in the 4- or 7-position with carboxy and naphthalide, unsubstituted.

3. A process as defined in claim 2 wherein said step (1) is conducted in the presence of toluene-p-sulfonic acid.

4. A process as defined in claim 2 wherein said step (2) is conducted under substantially anhydrous conditions.

5. A process as defined in claim 4 wherein said quinone is o-chloranil.

6. A process as defined in claim 2 wherein said compound (a) is (iv).

7. A process as defined in claim 6 wherein said indole compound (a) is 7-carboxyindole.

8. A process as defined in claim 7 wherein said aldehydic acid is naphthalaldehydic acid.

9. A process as defined in claim 8 wherein said compound (c) is (iv).

10. A process as defined in claim 9 wherein said indole compound (c) is 7-hexadecylsulfonamidoindole.

11. A process as defined in claim 9 wherein said indole compound (c) is 2-ortho-hydroxyphenyl indole.

12. A process as defined in claim 9 wherein said indole compound (c) is 7-carboxyindole.

13. A process as defined in claim 9 wherein said indole compound (c) is 5-bromo-7-octadecylsulfamoyl indole.

14. A process as defined in claim 2 wherein said compound (a) is (i).

15. A process as defined in claim 14 wherein said phenol compound (a) is 2,6-diisopropylphenol.

16. A process as defined in claim 15 wherein said compound (c) is (ii).

17. A process as defined in claim 16 wherein said 1-naphthol compound (c) is 2-hexadecyl-1-naphthol and said aldehydic acid is naphthalaldehydic acid.

18. A process as defined in claim 14 wherein said compound (c) is (i).

19. A process as defined in claim 18 wherein said phenol compound (a) is o-cresol, said phenol compound (c) is o-cresol and said aldehydic acid is 7-carboxy-phthalaldehydic acid.

20. A process as defined in claim 2 wherein said compound (a) is (ii).

21. A process as defined in claim 20 wherein said compound (c) is (ii).

22. A process as defined in claim 21 wherein said aldehydic acid is naphthalaldehydic acid.

23. A process as defined in claim 22 wherein said 1-naphthol compound (a) is 2-carboxy-1-naphthol and said 1-naphthol compound (c) is 2-carboxy-1-naphthol.

24. A process as defined in claim 1 wherein said oxidation product formed in step (2) is

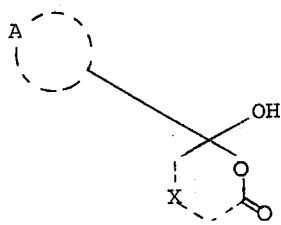

wherein A and X have the same meaning given above.

25. A process as defined in claim 1 wherein said oxidation product formed in step (2) is

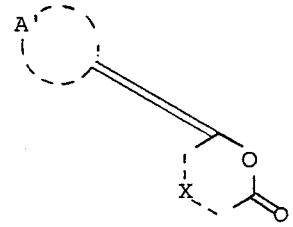

wherein A' is selected from

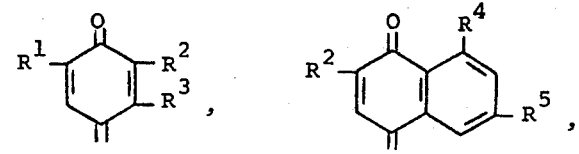

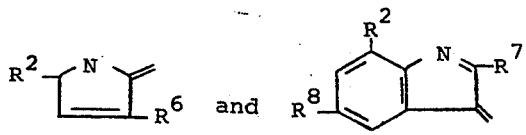

wherein $R^1$, $R^2$, $R^3$, $R^4$, $R^5$, $R^6$, $R^7$ and $R^8$ and X have the same meaning given above.

26. A process as defined in claim 1 wherein said quinone is 2,3-dichloro-5,6-dicyano-1,4-benzoquinone.

27. A process as defined in claim 1 wherein said quinone is o-chloranil.

28. A process as defined in claim 1 wherein said step (1) is conducted in the presence of toluene-p-sulfonic acid.

29. A process as defined in claim 1 wherein said compound (a) is (i).

30. A process as defined in claim 1 wherein said compound (a) is (ii).

31. A process as defined in claim 1 wherein said compound (a) is (iv).

* * * * *